(12) United States Patent
Maynard et al.

(10) Patent No.: US 9,901,648 B2
(45) Date of Patent: Feb. 27, 2018

(54) STABILIZATION OF BIOMOLECULES USING SUGAR POLYMERS

(71) Applicant: THE REGENTS OF THE UNIVERSITY OF CALIFORNIA, Oakland, CA (US)

(72) Inventors: Heather D. Maynard, Los Angeles, CA (US); Rock J. Mancini, Los Angeles, CA (US); Juneyoung Lee, Los Angeles, CA (US); En-Wei Lin, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 225 days.

(21) Appl. No.: 14/374,388

(22) PCT Filed: Jan. 25, 2013

(86) PCT No.: PCT/US2013/023235
§ 371 (c)(1),
(2) Date: Jul. 24, 2014

(87) PCT Pub. No.: WO2013/112897
PCT Pub. Date: Aug. 1, 2013

(65) Prior Publication Data
US 2014/0377838 A1 Dec. 25, 2014

Related U.S. Application Data

(60) Provisional application No. 61/591,729, filed on Jan. 27, 2012, provisional application No. 61/635,159, filed on Apr. 18, 2012.

(51) Int. Cl.
| | | |
|---|---|---|
| *A61K 47/58* | (2017.01) | |
| *C07H 3/04* | (2006.01) | |
| *C08F 110/00* | (2006.01) | |
| *C08F 10/00* | (2006.01) | |
| *C08F 210/00* | (2006.01) | |
| *C07H 17/04* | (2006.01) | |
| *A61K 31/713* | (2006.01) | |
| *A61K 38/47* | (2006.01) | |

(52) U.S. Cl.
CPC ............ *A61K 47/58* (2017.08); *A61K 31/713* (2013.01); *A61K 38/47* (2013.01); *C07H 3/04* (2013.01); *C07H 17/04* (2013.01); *C08F 10/00* (2013.01); *C08F 110/00* (2013.01); *C08F 210/00* (2013.01); *C12Y 302/01017* (2013.01)

(58) Field of Classification Search
None
See application file for complete search history.

(56) References Cited

U.S. PATENT DOCUMENTS

| | | |
|---|---|---|
| 5,789,469 A | 8/1998 | Sachinvala et al. |
| 8,268,801 B2 | 9/2012 | Puzo et al. |
| 2006/0172928 A1 | 8/2006 | Klaproth |
| 2007/0059828 A1 | 3/2007 | Yamaoka et al. |
| 2009/0124534 A1 | 5/2009 | Reineke et al. |
| 2011/0262991 A1* | 10/2011 | Raja .................. A61K 47/4813 435/188 |
| 2011/0286957 A1 | 11/2011 | Prieve et al. |

FOREIGN PATENT DOCUMENTS

| | | |
|---|---|---|
| EP | 0668294 A1 | 8/1995 |
| EP | 1095711 A2 | 5/2001 |
| JP | 200265289 A | 3/2002 |
| WO | 93-00807 A1 | 1/1993 |
| WO | 99-55310 A1 | 4/1999 |

OTHER PUBLICATIONS

Vázquez-Dorbatt, V., Tolstyka, Z. P., Chang, C. W., & Maynard, H. D. (2009). Synthesis of a pyridyl disulfide end-functionalized glycopolymer for conjugation to biomolecules and patterning on gold surfaces. Biomacromolecules, 10(8), 2207-2212.*
Vázquez-Dorbatt, V., & Maynard, H. D. (2006). Biotinylated glycopolymers synthesized by atom transfer radical polymerization. Biomacromolecules, 7(8), 2297-2302.*
Heredia, K. L., Nguyen, T. H., Chang, C. W., Bulmus, V., Davis, T. P., & Maynard, H. D. (2008). Reversible siRNA—polymer conjugates by RAFT polymerization. Chem. Commun., (28), 3245-3247.*
Dohi, H., Nishida, Y., Furuta, Y., Uzawa, H., Yokoyama, S. I., Ito, S., . . . & Kobayashi, K. (2002). Molecular design and biological potential of galacto-type trehalose as a nonnatural ligand of Shiga toxins. Organic letters, 4(3), 355-357.*
Potier, P., Bouchu, A., Gagnaire, J., & Queneau, Y. (2001). Proteinase N-catalysed regioselective esterification of sucrose and other mono-and disaccharides. Tetrahedron: Asymmetry, 12(17), 2409-2419.*
Srinivasachari, S., Liu, Y., Zhang, G., Prevette, L., & Reineke, T. M. (2006). Trehalose click polymers inhibit nanoparticle aggregation and promote pDNA delivery in serum. Journal of the American Chemical Society, 128(25), 8176-8184.*

(Continued)

*Primary Examiner* — Shaojia A Jiang
*Assistant Examiner* — Dale R Miller
(74) *Attorney, Agent, or Firm* — Quarles & Brady LLP

(57) ABSTRACT

Compositions and methods for stabilizing biomolecules are disclosed. Specifically, the compositions include novel homopolymers or copolymers containing trehalose side chains conjugated to biomolecules. When such homopolymers or copolymers are placed in close proximity to biomolecules, such as proteins, the homopolymers or copolymers protect and/or stabilize the biomolecule. The compositions and methods may be suitable for use in various industries such as healthcare (pharmaceuticals), molecular biology, biofuels, paper, personal care, detergent, photographic, rubber, brewing, dairy and food processing industries.

25 Claims, 45 Drawing Sheets

(56) References Cited

OTHER PUBLICATIONS

Queneau, Y., Jarosz, S., Lewandowski, B., & Fitremann, J. (2007). Sucrose chemistry and applications of sucrochemicals. Advances in carbohydrate chemistry and biochemistry, 61, 217-292.*

Kitagawa, et al., Chemoenzymatic Synthesis of Biodegradable Polymers Containing Glucobiose Branches, Macromol. Symp., 1999, 144:247-256.

Miura, et al., Chemoenzymatic Synthesis of Glycoconjugate Polymers Starting From Nonreducing Disaccharides, Journal of Polymer Science Part A: Polymer Chemistry, 2004, 42(18):4598-4606.

Park, et al., Enzyme-Catalyzed Synthesis of Sugar-Containing Monomers and Linear Polymers, Biotechnol. Bioeng., 2000, 70:208-216.

Spain, et al., Recent Advances in the Synthesis of Well-Defined Glycopolymers, Journal of Polymer Science: Part A: Polymer Chemistry, 2007, 45:2059-2072.

Teramoto, et al., Trehalose and Trehalose-Based Polymers for Environmentally Benign, Biocompatible and Bioactive Materials, Molecules, 2008, 13:1773-1816.

Wada, et al., A Specific Inhibitory Effect of Multivalent Trehalose Toward AB(1-40) Aggregation, Polymer Chemistry, 2011, 2:1822-1829.

Extended European Search Report dated May 11, 2015 in connection with PCT/US2013/023235.

Polonsky, Judith et al: "Cord factor, a toxic lipide from Mycobacterium tuberculosis. Synthesis of cord factor-active substances (esters of trehalose and synthetic branched chain acids)", retrived from STN Database accession No. 1957:16989, Database CAPLUS [Online] Chemical Abstracts Service, Columbus, Ohio, US.

Polonsky, Judith et al: "Cord factor, a toxic lipide from Mycobacterium tuberculosis. Synthesis of cord factor-active substances (esters of trehalose and synthetic branched chain acids)", Bulletin De La Societe Chimique De France 1471-8 Coden: BSCFAS; ISSN: 0037-8969, 1956.

Kitagawa, Suguru et al: "Manufacture of sugar esters by enzymic transesterification in hydrophilic organic solvents", retrieved from STN Database accession No. 2002:160179; & JP 200 265 289 A (Konan Kako K.K., Japan; Sangyo Gijutsu Sogo Kenkyusho; Toyobo Co., Lt) Mar. 5, 2002 (Mar. 5, 2002).

Laszlo, A. et al:, "Screening of synthetic trehalose 6,6'-diesters and trehalose 6-monoesters as potential immunoreactants for the serodiagnosis of tuberculosis", retrieved from STN Database accession No. 1995:211953.

Laszlo, A. et al: "Screening of synthetic trehalose 6,6'-diesters and trehalose 6-monoesters as potential immunoreactants for the serodiagnosis of tuberculosis", Research in Microbiology, 145(7), 563-72 CODEN: RMCREW; ISSN: 0923-2508, 1994, DOI: 10.1016/0923-2508(94) 90033-7 10.1016/0923-2508(94)90033-7.

Kitagawa, Masaru et al: "Chemoenzymatic synthesis of biodegradable polymers containing glucobiose branches", retrieved from STN Database accession No. 2000:107164.

Kitagawa, Masaru et al: Chemoenzymatic synthesis of biodegradable polymers containing glucobiose branches, Macromolecular Symposia, 144(Degradability, Renewability and Recycling—Key Functions for Future Materials), 247-256 CODEN: MSYMEC; ISSN: 1022-1360, 1999, DOI: 10.1002/MASY.19991440122 10.1002/MASY.19991440122.

Hoshino, Kazuhiro et al., "Temperature-sensitive sugar-containing copolymers, their manufacture, and purification of proteins using them", retrieved from STN Database accession No. 2002:672278; & JP200 2249 5223 A, Database CAPLUS [Online] Chemical Abstracts Service, Columbus, Ohio, US.

Miura, Yoshiko et al., "Chemoenzymatic synthesis of glycoconjugate polymers starting from nonreducing disaccharides", retrieved from STN Database accession No. 2004:751773, Database CAPLUS [Online] Chemical Abstracts Service, Columbus, Ohio, US.

Miura, Yoshiko et al., "Chemoenzymatic synthesis of glycoconjugate polymers starting from nonreducing disaccharides", Journal of Polymer Science, Part A: Polymer Chemistry (2004), 42(18), 4598-4606 CODEN: JPACEC; ISSN: 0887-624X, DOI: 10.1002/POLA.20385 10.1002/POLA.20385.

Miura, Yoshiko et al:, "Sugar-chain monomers and sugar-chain polymers having nonreducing disaccharide residues, and their manufacture", retrieved from STN Database accession No. 2004:903996; & JP 2004 300144A (Japan) Oct. 28, 2004 (Oct. 28, 2004).

Sun, Yue-E. et al: "Effects of fatty acid chain length and degree of unsaturation on the surface activities monoacyl trehaloses", retrieved from STN Database accession No. 2010:80315, Database CAPLUS [Online] Chemical Abstracts Service, Columbus, Ohio, US.

Sun, Yue-E. et al: "Effects of fatty acid chain length and degree of unsaturation on the surface activities of monoacyl trehaloses", Frontiers of Chemical Engineering in China, 3(4), 407-412 CODEN: FCECBU; ISSN: 1673-7369, 2009, DOI: 10.1007/11705-009-0255-9 10.1007/S11705-009-0255-9.

Ogata, Toshihiko et al:, "Ester processing stabilizers, resin compositions containing them, and improving method of processing stability of resins", retrieved from STN Database accession No. 2011:1337496; & JP 2011 207798 A (Sumitomo Chemical Co., Ltd., Japan) Oct. 20, 2011 (Oct. 20, 2011).

Hyun-Jong Cho et al:, "Evaluation of protein stability andpermeation of lyophilized polysaccharides-based microparticles for intranasal protein delivery", International Journal of Pharmaceutics, Elsevier BV, NL vol. 416, No. 1, Jun. 6, 2011 (Jun. 6, 2001), pp. 77-84, XP028264513, ISSN: 0378-5173, DOI: 10.1016/J.IJPHARM. 2011.06.009 [retrieved on Jun. 15, 2011].

International Search Report and Written Opinion under dated May 15, 2013 in connection with PCT/US2013/023235.

Mancini, R. J. et al., "Trehalose glycopolymers for stabilization of protein conjugates to environmental stressors", J. Am. Chem. Soc., Apr. 20, 2012, vol. 134, pp. 8474-8479.

Yoshiko, M. et al., "Chemoencymatic synthesis of glycojugate polymers starting from nonreducing disaccharidse", J. Polymer Science, 2004, vol. 24, pp. 4598-4606.

Kim, Y. et al., "Influenze immunization with trehalose-stablized virus-like particle vaccine using microneedles", NIH Public Access, PMC3082143, Apr. 26, 2011.

* cited by examiner

FIGURE 1 - a-b a)
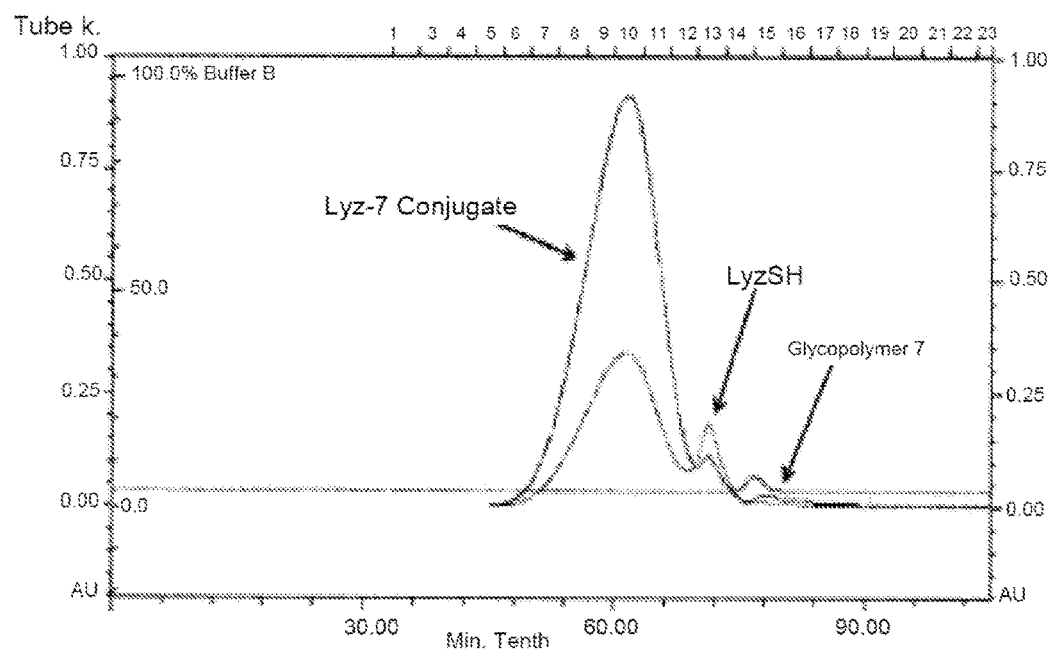
b)
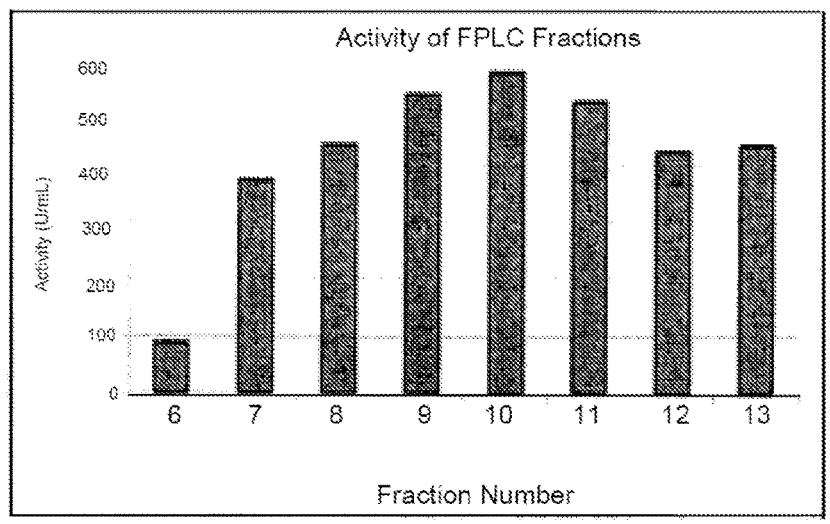
FIGURE 4 a-b

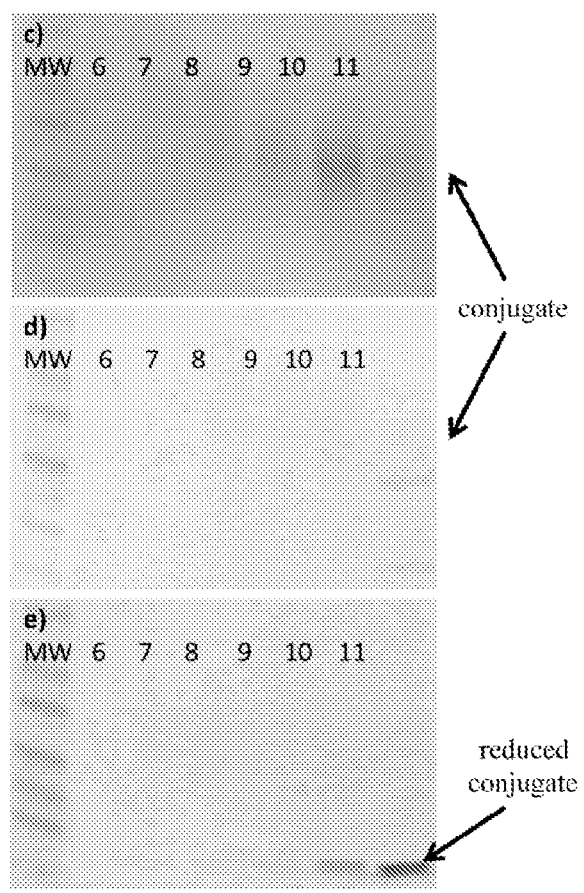
FIGURE 4 c-e

| Additive | – | – | P1 | P2 | P3 | T |
|---|---|---|---|---|---|---|
| Temp °C | 4 | 90 | 90 | 90 | 90 | 90 |
| Insulin | + | + | + | + | + | + |

FIGURE 31 a-b

Scheme 6 Illustrative conjugation reactions of thiolated lysozyme with polymer 4 and polymer 6 to form the respective conjugates.

Scheme 10. RAFT polymerization of 2 with CTA 5 to produce the thiol reactive glycopolymers Poly 5 through Poly 8. The glycopolymers were then conjugated to thiolated lysozyme.

Scheme 15. Conjugation of siRNA to Poly 5, Poly 6, and Poly 7.

STABILIZATION OF BIOMOLECULES USING SUGAR POLYMERS

CROSS-REFERENCE TO RELATED APPLICATION

This application represents the national stage entry of PCT International Application No. PCT/US2013/023235 filed Jan. 25, 2013, which claims the benefit from U.S. Provisional Application Ser. No. 61/591,729 filed Jan. 27, 2012, and U.S. Provisional Patent Application Ser. No. 61/635,159, filed Apr. 18, 2012, the disclosures of which are incorporated herein by reference in their entirety for all purposes.

STATEMENT REGARDING FEDERALLY SPONSORED RESEARCH OR DEVELOPMENT

This invention was made with Government support of Grant No. 1112550, awarded by the National Science Foundation, and of Grant No. EB136774, awarded by the National Institutes of Health. The government has certain rights in this invention.

FIELD OF THE INVENTION

Compositions and methods for stabilizing biomolecules are disclosed. Specifically, the compositions include novel trehalose-based homopolymers or copolymers conjugated to or added noncovalently to biomolecules, wherein the homopolymers or copolymers protect and/or stabilize the biomolecules.

BACKGROUND OF THE INVENTION

There is considerable interest in proteins, as therapeutics and as biochemical and chemical reagents. However, most proteins are inherently unstable and degrade upon storage, transport and use, necessitating regulated temperatures, controlled solvation, and the addition of carrier molecules that may need to be removed. Proteins are also known to denature due to physical or chemical stresses such as desiccation, heat, light, and pH change, further complicating application of certain biomolecules.

While attachment of poly(ethylene glycol) (PEG) to proteins has been widely used to increase in vitro and in vivo stability for therapeutic proteins by reducing access of proteolytic enzymes and screening through the renal filtration systems, PEGylation alone does not normally significantly increase protein stability with regard to temperature, desiccation, and storage.

In nature, many plants and animals endure complete dehydration stress by accumulating large amounts of sugar. For example, alpha, alpha-linked glucose disaccharides have been known to impart unusual stability to organisms tolerating anhydrobiosis (desiccation) and cryobiosis (low temperature) by protecting cells and proteins. However, there is a need in the art for agents that are more effective at stabilizing and protecting biomolecules against degradation upon exposure to environmental stresses over extended periods of time.

Trehalose has been described as an excipient in therapeutic protein formulations. US Patent (U.S. Pat. No. 6,991,790) describes use of trehalose and other disaccharides along with surfactants to stabilize antibody formulations for up to two years. In particular anti-CD20 was targeted for use in treatment of B cell lymphoma. U.S. Pat. No. 6,821,515 summarizes trehalose used at a high ratio (100-600:1) to stabilize proteins or antibodies to lyophilization. In particular anti-HER2 may be reconstituted with minimal loss of activity for the treatment of breast cancer. Trehalose has also been described to increase the solubility of polypeptides in aqueous solutions including aqueous solutions that contain organic solvents.

Trehalose has been employed in solid dosage/tablet applications. US Patents U.S. Pat. No. 6,589,554, U.S. Pat. No. 7,074,428 and U.S. Pat. No. 7,575,762 describe use of trehalose as a binder for solid quick disintegrating tablets, as well as for sustained release, for use in the buccal cavity fabricating solid formulations of varying release times and hardness. US Patents U.S. Pat. No. 7,425,341, U.S. Pat. No. 6,740,339, U.S. Pat. No. 6,455,053, and U.S. Pat. No. 5,762,961 disclose trehalose used as a binder or diluent in the composition of a solid quick-dissolve tablet sometimes along with other polyols such as cellulose derivatives. US Patents U.S. Pat. No. 5,958,455 and U.S. Pat. No. 6,194,001 summarize general solid tablet formulation with trehalose and the formulation for an amoxicillin tablet.

Trehalose was used as an excipient in a spray freezing process for the production of solid tablets (U.S. Pat. No. 4,762,857) and was also used in a powder that is administered by inhalation (U.S. Pat. No. 7,785,631). Trehalose changes the taste of a bitter-tasting active ingredient (U.S. Pat. No. 6,998,139).

Trehalose has been used to preserve whole cells, tissues, or organisms in the following patents: Trehalose was described to stabilize eukaryotic cells that have been specially immobilized on a support matrix for cryopreservation (U.S. Pat. No. 7,314,755). US Patents U.S. Pat. No. 7,169,606 and U.S. Pat. No. 6,528,309 summarize blood platelets that are stabilized to cryopreservation via trehalose that is introduced with various methods, temperatures and pressures. US Patents U.S. Pat. No. 6,770,478 and U.S. Pat. No. 4,806,343 summarize red blood cells and proteins in artificial blood preserved by addition of trehalose with or without metal ions prior to lyophilization. US Patents U.S. Pat. No. 7,270,946, U.S. Pat. No. 6,528,309, and U.S. Pat. No. 5,827,741 disclose methods for stabilizing mammalian cells to lyophilization and cryopreservation respectively by using trehalose as an excipient. Bacteria have been preserved using trehalose in the medium (U.S. Pat. No. 6,610,531). US Patents U.S. Pat. No. 6,475,716 and U.S. Pat. No. 6,653,062 describe preservation of whole organs with trehalose and a trehalose preservation solution generally applicable to biologics, respectively. Trehalose combined with biologically safe acids or ethanol was used to prolong the shelf life of various products including pharmaceuticals (U.S. Pat. No. 6,005,100).

Trehalose has also been described in various administrations and deliveries. Examples are in the treatment of osteoporosis (U.S. Pat. No. 6,440,446), in the treatment of articular failure or to improve blood circulation (U.S. Pat. No. 7,214,667 and U.S. Pat. No. 5,981,498), in ophthalmic use (U.S. Pat. No. 6,555,526), in peptide or protein controlled release from glassy trehalose (U.S. Pat. No. 6,187,330), and in delivery of trehalose particles to cells (U.S. Pat. No. 5,840,878).

Previously, trehalose-based materials have been produced as cross-linked polymer networks including poly-substituted trehalose vinylbenzyl ether thermo-set resins (Teramoto and Shibata, 2004). Achieving trehalose linear polymers are challenging as the anomeric centers are relatively unreactive due to the 1,1-glycosidic linkage (Wolfenden and Yuan, 2008). Therefore, typical synthetic routes to produce trehalose-based monomers contain several protecting and deprotecting steps either by using bifunctional monomers targeting the 6,6'-positions, or by producing mixtures of regioisomers that are not well defined. For example, a simple strategy for synthesizing trehalose linear polymers was first reported in 1979, but selectivity to form linear polymer versus the branched one was unclear at that time (Kurita, Hirakawa, et al., 1979).

Polymerization of diamino-type trehalose was explored to overcome the issue of branching, but the overall process was more complicated (Kurita, Masuda, et al., 1994). Acetalization (Teramoto, Arai, et al., 2004), enzymes (Park, Kim, et al., 2000), Diels-Alder reactions (Teramoto, Arai, et al., 2006), and click chemistry (Srinivaschari, Liu, et al., 2006 and 2007) have been exploited to synthesize trehalose-based linear polymers, with the later study being extended to biological systems. However, previous research and patents described reactions of incorporating trehalose into the polymer backbone rather than as a side chain. Polymers with trehalose in the backbone cannot be prepared in such a way to have end groups for attachment to biomolecules. Moreover, polymers with trehalose in the backbone cannot be prepared with narrow molecular weight distributions. Further, because the alcohols are important for hydration and protective properties, they may not protect biomolecules as well as a linear side chain polymer.

Although Kitagawa and his co-workers described a trehalose side chain polymer (Kitagawa, Chalermisrachai, et al., 1999), the polymers were synthesized by enzymatic synthesis. Enzymatic synthesis is extremely difficult to scale up. The polymers were prepared by free radical polymerization, and the reaction did not allow for the synthesis of one reactive end group for conjugation to biomolecules and the reaction did not prepare polymers with narrow molecular weight distributions. Moreover, the monomers were synthesized with excess divinyl adipates and any as-formed bisfunctionalized trehaloses were not removed. Therefore, the as-prepared polymers were likely to be a mixture of products, containing cross-linked materials. Finally, the polymers were not used to stabilize biomolecules nor were they conjugated to proteins or other biomolecules.

A monomer was described in US patent of U.S. Pat. No. 5,856,416 with a the goal of obtaining cross-linked networks for use in contact lenses. Further, in U.S. Ser. No. 12/134, 556 trehalose condensation polymers were claimed to stabilize biologically active ingredients, in particular nucleic acids in mixtures. The polymers contain trehalose as part of the backbone. Moreover, condensation polymers described in the patent application could not be prepared with end groups to conjugate to proteins and they can not be prepared with narrow molecular weight distributions.

PEGylation or attachment of polyethylene glycol (PEG) or PEG side chain polymers is known to enhance the pharmacological properties, e.g., protecting biomolecules from enzymatic degradation (Lyczak and Morrison, 1994; Syed, Schuyler, et al., 1997; Cohen, Yoshioka, et al., 1991). PEGylation alone does not typically significantly increase protein stability to temperature, desiccation, and storage. It has been recently reported that poly(carboxybetaine), a polyzwitterion, can be attached to proteins to enhance protein thermal stability (Keefe and Jiang, 2012; Yang, Zhang, et al., 2009). Recently, Applicants disclosed poly(styrene sulfonate)-based polymers that stabilize heparin binding proteins to environmental stressors (PCT/US12/66905; Nguyen, Kim, et al., 2013).

Needed in the art is a homopolymer or copolymer with side chain trehalose having desirable protection capabilities.

SUMMARY OF THE INVENTION

In one aspect, the present invention relates to a monomer for use in making a homopolymer or a copolymer for stabilizing a biomolecule. The monomer has the general structure of $R_1R_2C=CR_3R_4$, wherein $R_1$-$R_4$ are independently selected from hydrogen or a side chain comprising at least one carbon atom, and at least one of $R_1$-$R_4$ is a side chain comprising -L-trehalose, wherein L is a linker molecule that links trehalose to the monomer through at least one of the trehalose hydroxyl groups (—OH). In one embodiment, L is selected from group consisting of -aryl-$(CH_2)_n$— (n=0-6), —(COO)—$(CH_2)_n$— (n=0-6), —(CON)—$(CH_2)_n$— (n=0-6), and —$(CH_2)_n$— (n=0-6).

In another aspect, the present invention relates to a homopolymer or co-polymer made from one or more of the monomer as shown above. The homopolymer or copolymer comprises the general structure of $R_5$—[$R_1R_2C$—$CR_3R_4$]$_n$—$R_6$, wherein $R_1$-$R_4$ are independently selected from hydrogen or a side chain comprising at least one carbon atom, and wherein at least one of $R_1$-$R_4$ is a side chain comprising -L-trehalose, wherein L is a linker molecule that links trehalose to the monomer through at least one of the trehalose hydroxyl groups (—OH), and wherein $R_5$ and $R_6$ are independently selected from the group consisting of -Alkyl, -Alkenyl, -Alkynyl, -aryl, —C(CN)(Alkyl)$_2$, —S$_2$C—S-Alkyl, —C(CO)(Alkyl)-(OCH$_2$CH$_2$)$_n$— COO— CH$_2$CH$_2$—CO-Alkyl (n=1-10), and biomolecules. In one embodiment, L is selected from group consisting of -aryl-$(CH_2)_n$— (n=0-6), —(COO)—$(CH_2)_n$— (n=0-6), —(CON)—$(CH_2)_n$— (n=0-6), and —$(CH_2)_n$— (n=0-6).

In one specific embodiment of the monomer and polymer, the biomolecule is selected from the group consisting of proteins, enzymes, antibodies, DNAs, RNAs, siRNAs, and pharmaceutical compositions.

In one specific embodiment of the monomer and polymer, the side chain -L-trehalose has a specific structure as shown below.

In one specific embodiment of the monomer and polymer, any of $R_1$-$R_4$ that is not-L-trehalose is either hydrogen or an alkyl group. In another specific embodiment, the alkyl group is preferably a methyl group. In another specific embodiment, the polymers have the specific structures as shown below.

In one specific embodiment of the monomer and polymer, one of $R_1$-$R_4$ is an alkyl group and two of $R_1$-$R_4$ are hydrogens. In another specific embodiment, the alkyl group is preferably a methyl group. In another specific embodiment, the polymers have the specific structures as shown below.

In one specific embodiment of the monomer and polymer, three of $R_1$-$R_4$ are hydrogens. In another specific embodiment, the polymers have the structures as discussed as below.

In another aspect, the present invention relates to a method of synthesizing a homopolymer or copolymer for stabilizing a biomolecule, the method comprising the steps of (a) incorporating a side chain comprising a trehalose molecule into a polymerizable monomer and (b) polymerizing the resulting monomer to obtain a polymer following any above methods. In one specific embodiment, the homopolymer or copolymer is generated through chemical synthesis. In another specific embodiment, the polymerizable monomer is selected from the group consisting of a styrene monomer, an acrylate monomer, a methacrylate monomer, an acrylamide monomer, a methacrylamide monomer, a vinyl monomer, a norborenyl monomer, and a strained cycle alkene monomer.

In yet another specific embodiment of the method, the step of polymerizing the resulting monomer to obtain a homopolymer or copolymer is performed by any one of, but not limited to the following techniques; reversible addition-fragmentation (RAFT) polymerization, atom transfer radical polymerization (ATRP), nitroxide mediated polymerization (NMP), cyanoxyl-mediated free radical polymerization, conventional radical polymerization, or ring opening polymerization (ROMP).

In yet another specific embodiment of the method, one or more of the hydroxyl groups of the trehalose are protected by the formation of an acetal or an ether.

In another aspect, the present invention relates to a method of stabilizing a biomolecule comprising the step of conjugating the biomolecule with a homopolymer or copolymer from a monomer having the above structures or being produced using any of the above methods. In one specific embodiment, the biomolecule is covalently conjugated to the homopolymer or copolymer backbone.

In another aspect, the present invention relates to a composition comprising a biomolecule conjugated to a homopolymer or copolymer comprising the general structure of $-[R_1R_2C-CR_3R_4]_n-$, wherein $R_1$-$R_4$ are independently selected from hydrogen or a side chain comprising at least one carbon atom, and wherein at least one of $R_1$-$R_4$ is a side chain comprising a structure of -L-trehalose, wherein L is a linker molecule that links trehalose through at least one of the trehalose hydroxyl groups (—OH), and wherein the homopolymer or copolymer further comprises a biomolecule reactive chain transfer agent attached to one or both termini of the homopolymer or copolymer backbone.

These and other features of the present invention will become apparent to the skilled artisan from the following detailed description and incorporated Appendix materials considered in conjunction with the accompanying drawings.

BRIEF DESCRIPTION OF THE DRAWINGS

FIG. 4a, b, c, d, and e shows a) FPLC trace of the conjugation of thiolated lysozyme LyzSH to thiol-reactive glycopolymer 6 monitored by conductivity, and UV absorbance at 254 nm and 280 nm with b) corresponding activity of FPLC fractions collected in the region of Lyz-6 conjugate. SDS-PAGE of FPLC fractions 6-11 containing Lyz-6 under non-reducing conditions stained with c) Iodine or d) coomassie along with e) the same fractions run under reducing conditions.

DETAILED DESCRIPTION OF THE INVENTION

In General

Figure 1:
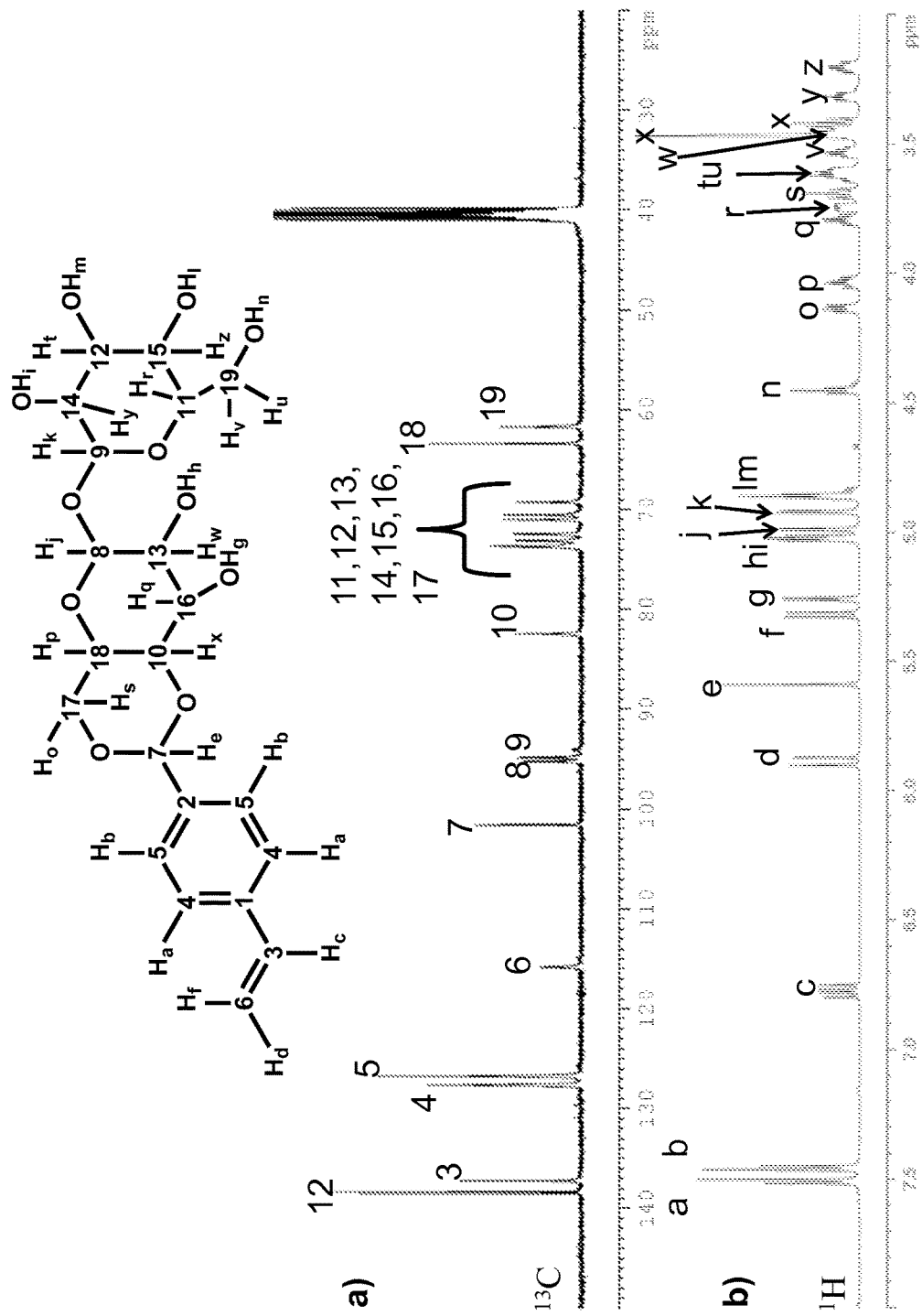
FIG. 1a, b is a series of NMR spectra obtained a)$^{13}$C NMR, b) $^1$H NMR, of glycomonomer 2 (D6-DMSO).

Before the present materials and methods are described, it is understood that this invention is not limited to the particular methodology, protocols, materials, and reagents described, as these may vary. It is also to be understood that the terminology used herein is for the purpose of describing particular embodiments only and is not intended to limit the scope of the present invention which will be limited only by any later-filed nonprovisional applications.

As used herein and in the appended claims, the singular forms "a", "an", and "the" include plural reference unless the context clearly dictates otherwise. As well, the terms "a" (or "an"), "one or more" and "at least one" can be used interchangeably herein. The terms "comprising", "including", and "having" can be used interchangeably.

Unless defined otherwise, all technical and scientific terms used herein have the same meanings as commonly understood by one of ordinary skill in the art. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

THE INVENTION

In one aspect, the present invention relates to a homopolymer or copolymer that remarkably stabilizes biomolecules, preferably to environmental stressors, either when added to biomolecules to form a mixture or when covalently conjugated to biomolecules. The term "homopolymer" refers to a polymer produced from the polymerization of only one monomer containing at least one trehalose side chain. The term "copolymer" refers to a polymer derived from at least two monomers and at least one of the monomers contains at least one trehalose side chain. Although only homopolymers are discussed in the Examples, a person having ordinary skill in the art would understand that the present invention extends to copolymers.

To make copolymer, one would polymerize a monomer mixture of at least two different monomers, at least one of the monomer includes at least one trehalose side chain. The methods for producing homopolymers would be suitable for making copolymers.

The polymer or co-polymer includes one or more side chains that comprise a trehalose moiety. Compared to the same concentration of trehalose, the homopolymer or copolymer is substantially and surprisingly more effective than trehalose alone at stabilizing biomolecules. Furthermore, conjugating the homopolymer or copolymer to the biomolecule significantly enhances the biomolecule's stability. In one example below, stabilization of a protein to desiccation and heat are demonstrated.

In one embodiment of the present invention, the homopolymer or copolymer may be produced from one or more of the monomers having a general structure of (1)

$$R_1R_2C=CR_3R_4 \tag{1}$$

wherein $R_1$-$R_4$ are independently selected from hydrogen, an alkyl, alkenyl, alkynl, or aryl group or a side chain, preferably comprising at least one carbon atom, and wherein at least one of $R_1$-$R_4$ is a side chain comprising -L-trehalose, wherein L is a linker that links trehalose to the monomer through at least one of the trehalose hydroxyl groups (—OH).

L may be any groups having chemical structures suitable for linking monomer and trahalose. In one embodiment, L may include at least one methylene group (—CH$_2$—)$_n$ (n=0-6). In another embodiment, L may include at least one aromatic group (-aryl-).

In one specific embodiment, in the monomer with the general structure of (1), L may be either -aryl-(CH$_2$)$_n$— (n=0-6), or —(COO)—(CH$_2$)$_n$— (n=0-6), or —(CON)—(CH$_2$)$_n$— (n=0-6). In one embodiment, L may be —(CH$_2$)$_n$— (n=0-6) wherein trehalose is directly linked to monomers.

In one specific embodiment, the side chain -L-trehalose has a structure selected from the group consisting of:

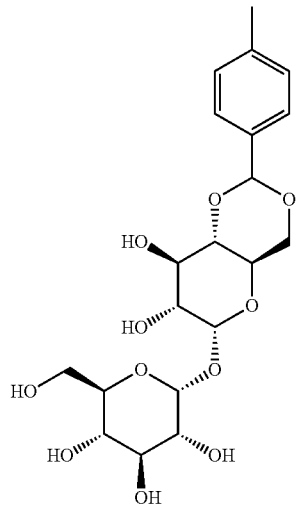

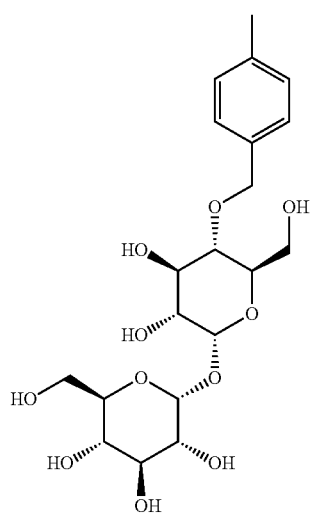

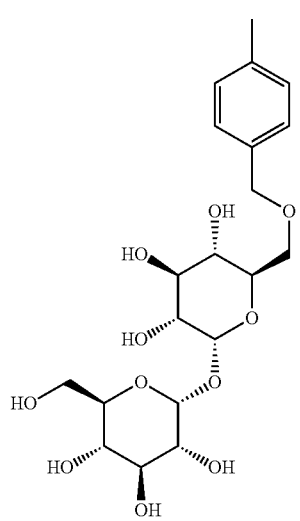

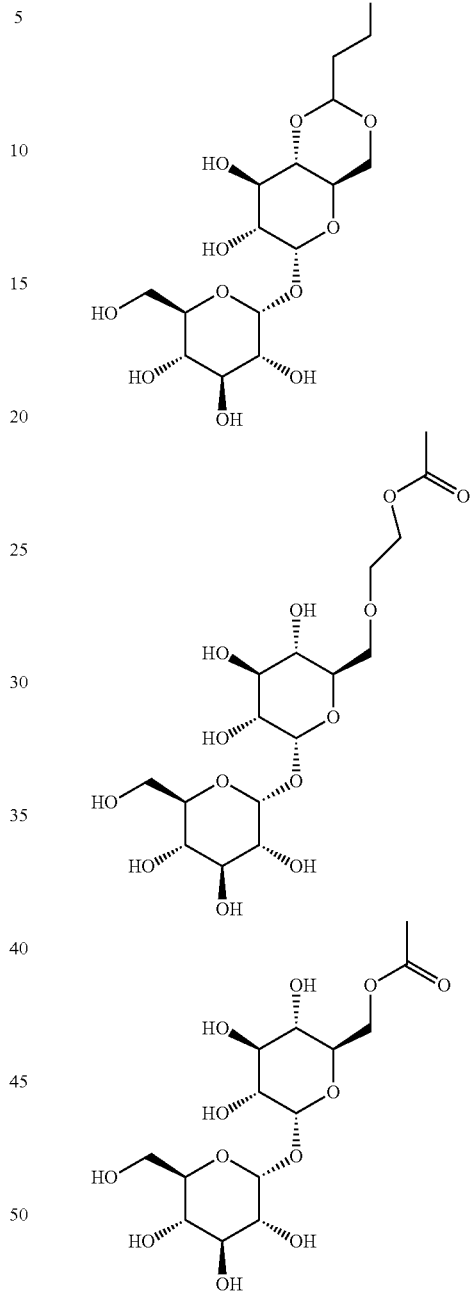

In one embodiment, the monomer having a general structure of (1) may be produced through chemical reactions between trehalose and another monomer having any suitable functional groups. In one specific embodiment of the present invention, the suitable functional groups may include —OH, —COOH, —COOR, —OR, —CONH$_2$, CONHR, and —COX, where R is an alkyl, alkenyl, alkynyl, or an aryl group, and X is a halogen group.

In one specific embodiment of the present invention, the monomer which may be used to produce the monomer with the general structure of (1) may be selected from the group consisting of a styrene monomer, an acrylate monomer, a methacrylate monomer, an acrylamide monomer, a methacrylamide monomer, a vinyl monomer, a norborenyl monomer, and a strained cycle alkene monomer.

In one embodiment, the present invention relates to a homopolymer or copolymer made from one or more of the monomer having the general structure of (1), the homopolymer or copolymer comprises the general structure of (2):

$$R_5—[R_1R_2C—CR_3R_4]_n—R_6 \quad (2)$$

wherein $R_1$-$R_4$ are independently selected from hydrogen or a side chain comprising at least one carbon atom, and wherein at least one of $R_1$-$R_4$ is a side chain comprising -L-trehalose, wherein L is a linker molecule that links trehalose to the monomer through at least one of the trehalose —OH groups, and wherein $R_5$ and $R_6$, the end groups, are independently selected from the group consisting of -Alkyl, -Alkenyl, -Alkynyl, -Aryl, —C(CN)(Alkyl)$_2$, —S$_2$C—S-Alkyl, —C(CO)(Alkyl)-(OCH$_2$CH$_2$)$_n$— COO— CH$_2$CH$_2$—CO-Alkyl (n=1-10), and biomolecules.

In one embodiment, any of $R_1$-$R_4$ that is not-L-trehalose is either hydrogen or an alkyl group. In one specific embodiment, the alkyl group is preferably a methyl group.

In one embodiment, one of $R_1$-$R_4$ is an alkyl group and two of $R_1$-$R_4$ are hydrogens. In one specific embodiment, the alkyl group is preferably a methyl group. In another specific embodiment, the homopolymer or copolymer has the structure:

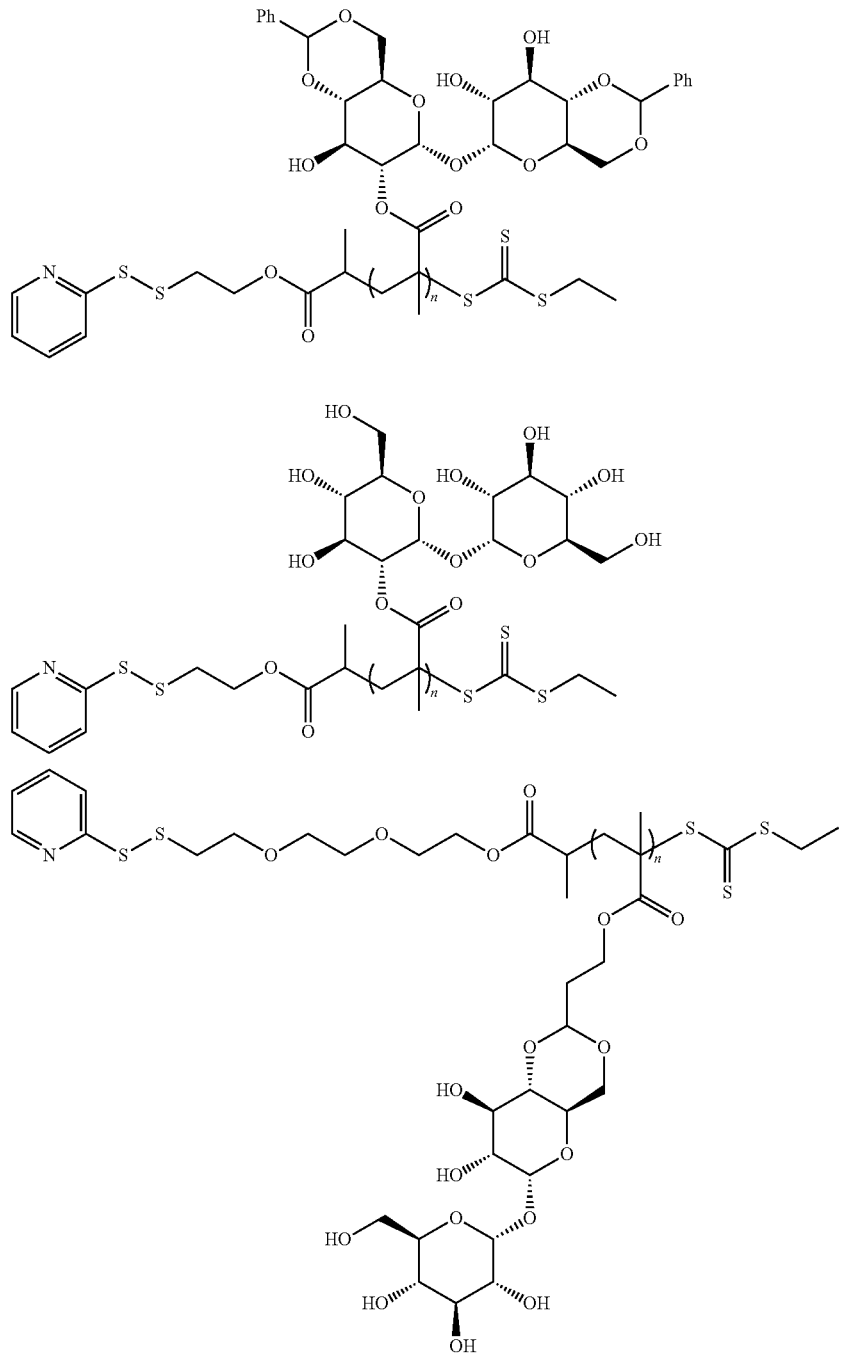

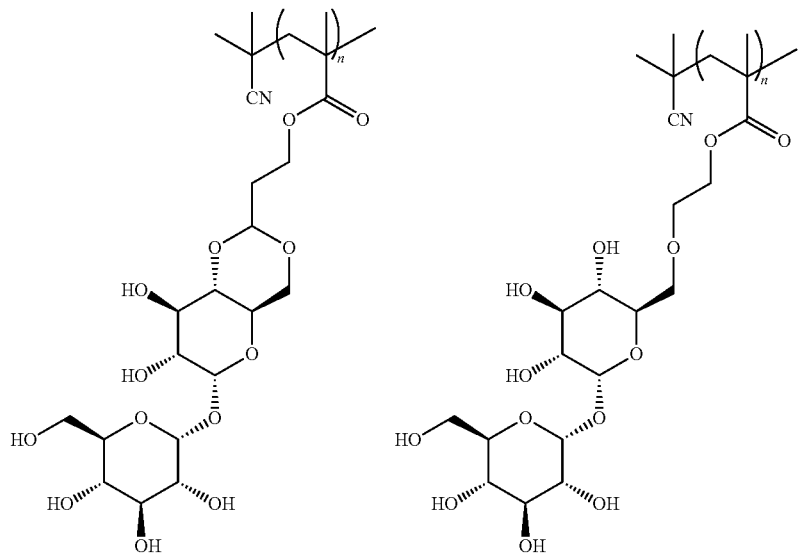
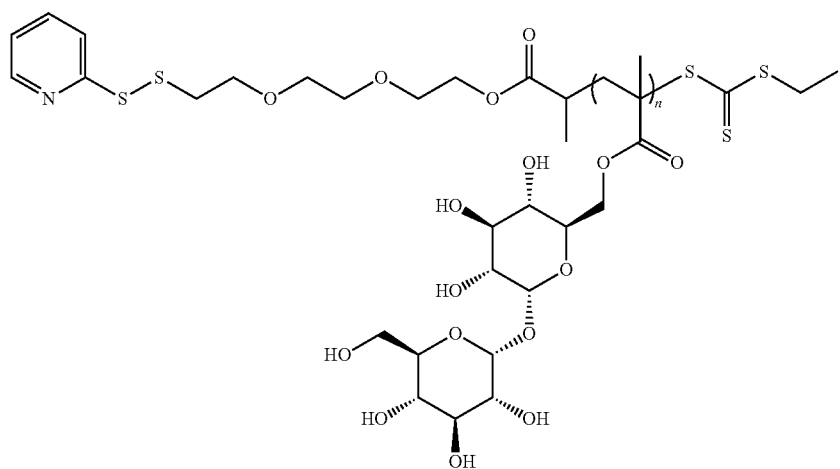
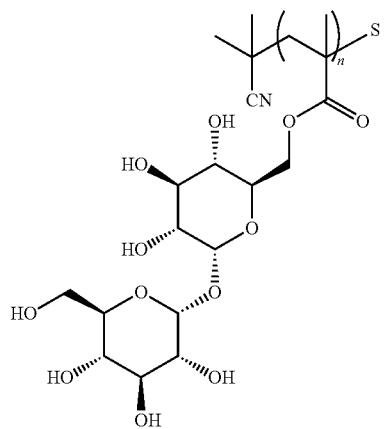

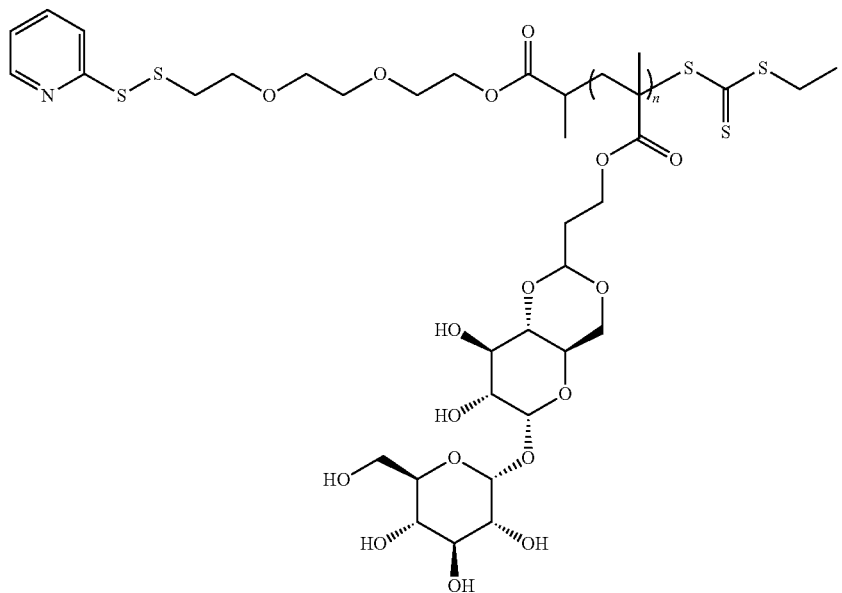
In one embodiment, three of $R_1$-$R_4$ are hydrogens. In one specific embodiment, the homopolymer or copolymer has the structure:
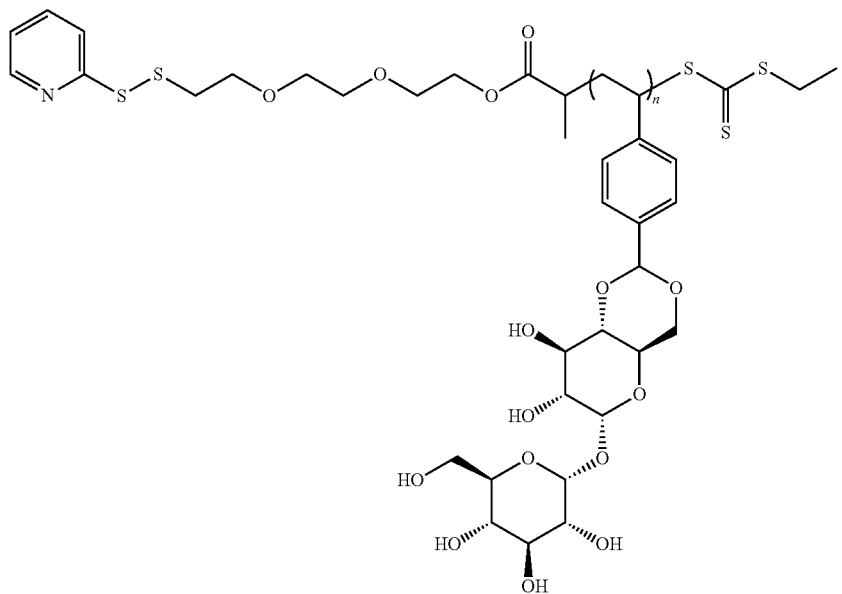

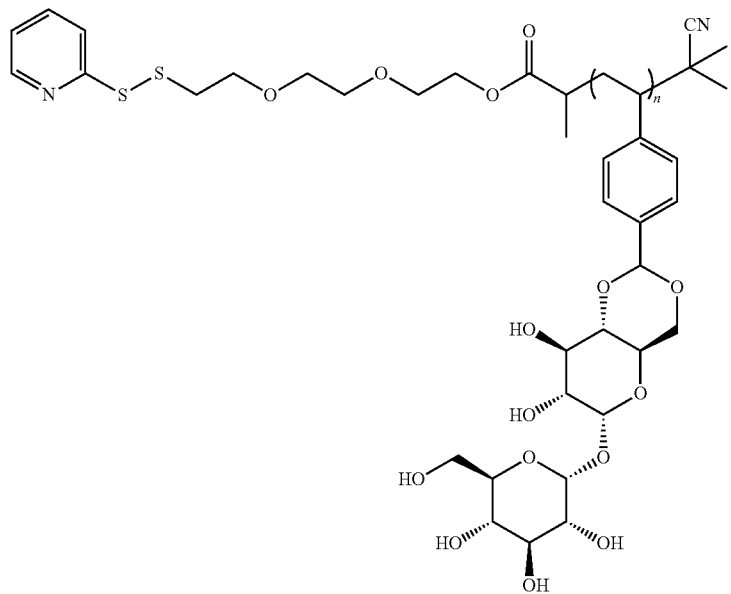
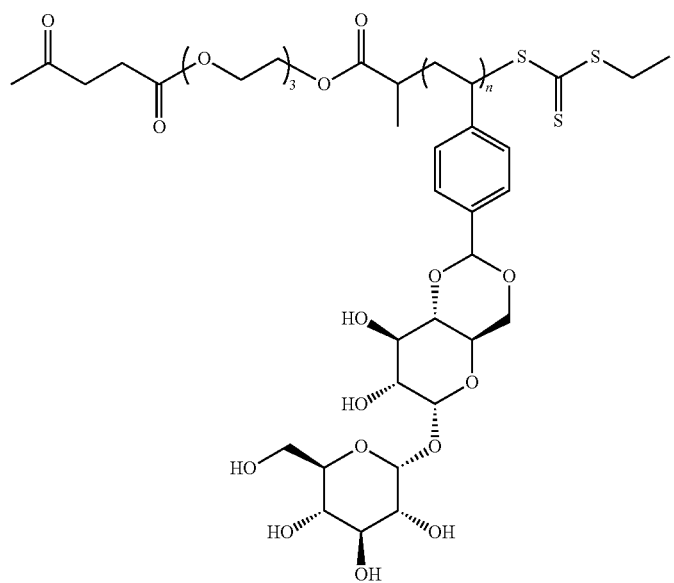

-continued

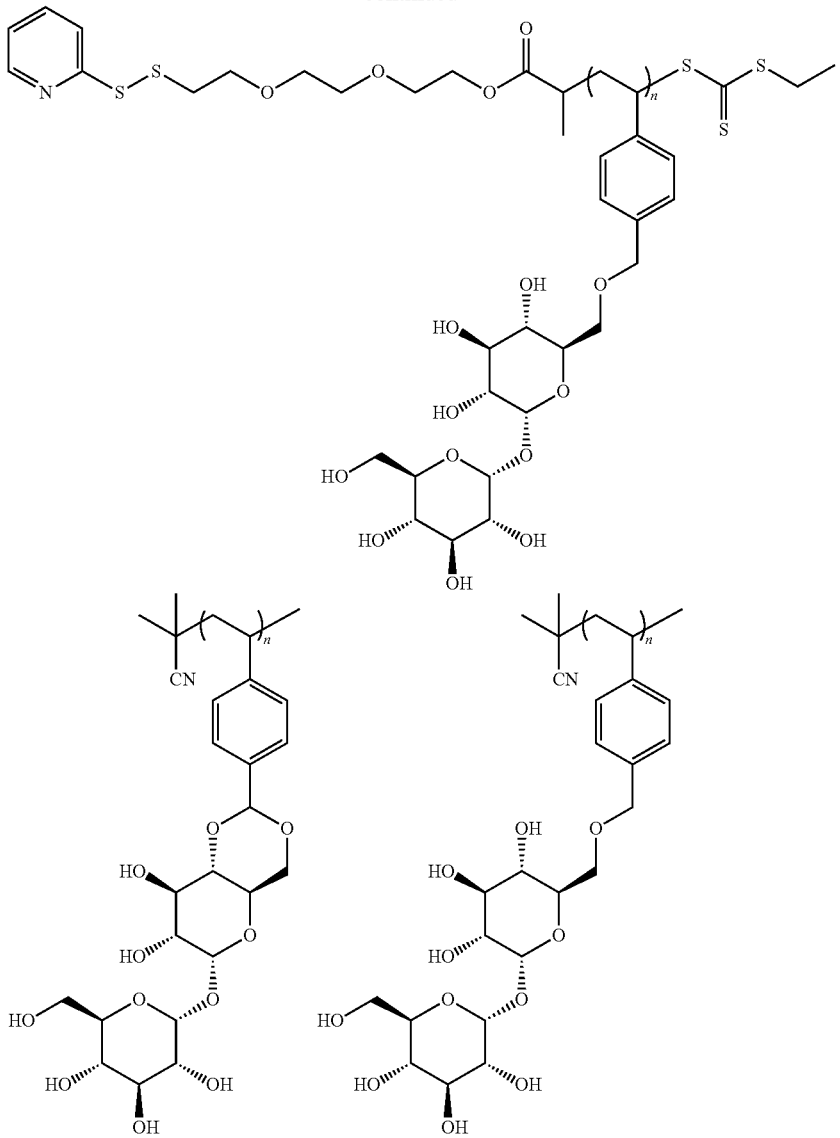

In one embodiment, the homopolymer or copolymer with the general structure of (2) may be produced from the monomer with the general structure of (1) by using any suitable polymerization reactions. In another embodiment, the polymerization reactions may include reversible addition-fragmentation (RAFT) polymerization, atom transfer radical polymerization (ATRP), nitroxide mediated polymerization (NMP), cyanoxyl-mediated free radical polymerization, conventional radical polymerization, or ring opening polymerization (ROMP).

In one specific embodiment, the homopolymer or copolymer with the general structure of (2) may be produced from the monomer with the general structure of (1) by using reversible addition-fragmentation (RAFT) polymerization. In another specific embodiment, the homopolymer or copolymer with the general structure of (2) may be produced from the monomer with the general structure of (1) by using atom transfer radical polymerization (ATRP). Detailed descriptions of similar polymerization reactions were included in U.S. Pat. No. 5,789,487 and WO98/01478.

In another embodiment, one would create the polymer through production of polymers having some linking groups, which would later be used to link trehalose to make the desired trehalose-containing polymers.

In some embodiments, the end groups of $R_5$ and $R_6$ are independently selected from the group consisting of activated disulfides, pyridyl disulfide, 5-thio-2-nitrobenzoic acid, disulfide reductants, Michael acceptors, maleimides, maleimide derivatives, dihalomaleimides, vinyl groups, vinyl sulfones, acryloyl derivatives, haloacetyl, alkyl halide derivatives, aziridines, arylating agents, isothiocyanates, isocyanates, acryl azides, activated esters, N-hydroxysuccinimide esters, para-nitrophenyl esters, sulfonyl chlorides, aldehydes and glyoxals (with or without reductive amination), epoxides (also called oxiranes), carbonates, arylating agents, imidoesters, carbodiimides, anhydrides, primary amines, secondary amines, tertiary amines, diazoalkanes, diazoacetyls, carbonyldiimidazoles, carbonates, chloroformates, alkyl halogens, isocyanates, aminooxy (hydroxylamines), hydrazines, alkynes, derivatives thereof, and a combination thereof.

In one embodiment, the present invention relates to a method of application of a homopolymer or copolymer having a structure of (2) that remarkably stabilizes biomolecules to environmental stressors when added to biomolecules. In one specific embodiment of the present invention, the homopolymer or copolymer may be covalently linked to biomolecules or biologic agents through chemical reactions between the end groups and the functional groups in the biomolecules or biologic agents. In one specific embodiment, the method comprising the steps of (a) incorporating a side chain comprising a trehalose molecule into a polymerizable monomer; and (b) polymerizing the resulting monomer to obtain a homopolymer or copolymer according to a suitable polymerization reaction. The suitable polymerization reactions may include reversible addition-fragmentation (RAFT) polymerization, atom transfer radical polymerization (ATRP), nitroxide mediated polymerization (NMP), cyanoxyl-mediated free radical polymerization, conventional radical polymerization, or ring opening polymerization (ROMP).

In some embodiments, the end groups may react with a free thiol in the biologic agent. Examples of such end groups may include, but are not limited to, activated disulfides (also called thiol-disulfide exchange reagents) such as pyridyl disulfide, 5-thio-2-nitrobenzoic acid, and disulfide reductants, Michael acceptors such as maleimides, maleimide derivatives including dihalomaleimides, and vinyl groups including vinyl sulfones and acryloyl derivatives, haloacetyl and other alkyl halide derivatives, aziridines, and arylating agents. In one preferred embodiment, the end group may link biologic agents with a disulfide bond (—S—S—).

In some embodiments, the end groups may react with a free amine in the biologic agent. Examples of such end groups may include, but are not limited to, isothiocyanates, isocyanates, acryl azides, activated esters such as N-hydroxysuccinimide and para-nitrophenyl, sulfonyl chlorides, aldehydes and glyoxals (with or without reductive amination), epoxides (also called oxiranes), carbonates, arylating agents, imidoesters, carbodiimides, and anhydrides.

In some embodiment, Michael acceptors may also react with amines, depending on the reaction conditions—i.e. more basic conditions. Michael acceptors may include maleimides, maleimide derivatives including dihalomaleimides, and vinyl groups including vinyl sulfones and acryloyl derivatives, haloacetyl and other alkyl halide derivatives, aziridines, and arylating agents.

In some embodiments, the end groups may react with a carboxyl group in the biologic agents. Examples of such end groups may include, but are not limited to, amines via amidation chemistry, diazoalkanes and diazoacetyl compounds.

In some embodiments, the reactive groups may react with hydroxyl groups in the biologic agents. Examples of such end groups may include, but are not limited to, epoxides (also called oxiranes), carbonyldiimidazoles, carbonates and chloroformates, alkyl halogens, and isocyanates.

In some embodiments, the end groups may react with an aldehyde, ketone, or any other oxo moiety introduced into the biologic agent. Examples of such end groups may include, but are not limited to, aminooxy (hydroxylamines), hydrazines, and amines (with and without reductive amination).

In some embodiments, the end group may react with azide or alkyne groups introduced in the biologic agent. Examples of such end groups include, but are not limited to, alkynes and amines.

In some embodiments, the moiety that reacts with the reactive group is present naturally in the biologic agent. In some embodiments, the moiety that reacts with the reactive group is added to the biologic agent by chemical modification (e.g., by chemical synthesis) or biological modification (e.g., inclusion of non-naturally amino acids via recombinant synthesis).

In one embodiment, the present invention relates to a composition and a method of applications of a homopolymer or copolymer having a structure of (2) that remarkably stabilizes biomolecules to environmental stressors by mixing a suitable amount of a homopolymer or copolymer having a structure of (2) with the biomolecule. In this embodiment, the formation of chemical bonds between the homopolymers or copolymers and the biomolecule are not necessary. The homopolymers or copolymers are not covalently attached to the biomolecule, but added as an excipient.

A suitable concentration of the homopolymer or copolymer may be 50 µg/mL, 75 µg/mL, 100 µg/mL, 200 µg/mL, 300 µg/mL, 400 µg/mL, 500 µg/mL, 700 µg/mL, 900 µg/mL, 1 mg/mL, or 5 mg/mL, preferably 100 µg/mL. A suitable ratio of the polymers or co-polymers to biomolecule may be 1:1, 10:1, 20:1, 50:1, 100:1, or 200:1, and preferable 50:1 or 100:1, and most preferably 100:1.

The Examples below (e.g., Examples 1, 6 and 7) disclose typical steps for mixing the trehalose-based homopolymer or copolymer with biomolecules. In one embodiment, a suitable amount of the solid phase of trehalose-based homopolymers or co-polymers may be added into the solution of biomolecules. In another embodiment, a solution of the trehalose-based homopolymers or copolymers may be made, and a suitable amount of the trehalose-based homopolymer or copolymer solution may be added into the solution of biomolecules. In another embodiment, a suitable amount of the solid phase of trehalose-based homopolymers or copolymers may be added into the solid phase of biomolecules to form a mixture, and the mixture may be made into a solution. In another embodiment, solution phase trehalose may be added to solution or solid protein and dried to solid.

One may mix the protective polymer and the target biomolecule together in various suitable ways. We have done successful mixing at temperatures ranging from 4° C. to room temperature (23° C.) and we believe that there is flexibility with this parameter. The temperature is not critical so far as the polymer is concerned, only that the protein or biomolecule maintains activity during the mixing, which may be temperature dependent. A pH of neutral (7.4) is preferred, but not necessary. As with temperature, the biomolecule should remain active and this activity may be pH dependent. Mixing time was typically brief in the examples. We typically mixed right before use. However, this is typically not necessary. Buffers are not critical so far as the polymer concerned, but may matter depending on the protein. Our examples were typically run with phosphate buffered saline. Whatever conditions will maintain activity of the protein or biomolecule prior to being fully mixed with the polymer should be used.

Applicants envision that suitable monomers for producing the homopolymers or copolymers may include a styrene monomer, an acrylate monomer, a methacrylate monomer, an acrylamide monomer, a methacrylamide monomer, a vinyl monomer, a norborenyl monomer, and a strained cycle alkene monomer.

The invention may also include, but is not limited to, stabilization of proteins, enzymes, antibodies, DNA, siRNA, and pharmaceutical compositions against the environmental stresses which include but are not limited to heat, desiccation, light, storage, exposure to enzymes, endo- and exonucleases and pH variation. Commercial applications of this invention include, but are not limited to, stabilization of proteins, enzymes, antibodies, DNA, siRNA, and pharmaceutical compositions thereof utilized as therapeutics, biochemical reagents, and chemical reagents.

The homopolymer or copolymer with or without a sugar side chain of trehalose may be added to a solution or powder form of the biomolecule alone or as part of a formulation. The homopolymer or copolymer alone with or without a sugar side chain of trehalose may also be covalently attached to a protein or other biomolecule to form a conjugate. Unconjugated homopolymer or copolymer may be added to the homopolymer or copolymer conjugate.

This invention is distinguished from the use of a trehalose alone as a stabilizer in that the trehalose is attached to a homopolymer or copolymer backbone. By attaching a trehalose to side chain of a homopolymer or copolymer, the protective properties of the trehalose are unexpectedly and dramatically enhanced. The desiccation and heat stability was significantly greater for the homopolymer or copolymer than for trehalose itself, at the same concentration of trehalose. This invention is also distinguished from the use of trehalose alone as surprisingly, the trehalose polymer is a better stabilizer.

Previously reported trehalose-based homopolymers or copolymers include a sugar as part of the homopolymer or copolymer backbone, rather than in a side chain. In this disclosure, the sugar of trehalose is part of a side chain. Homopolymers or copolymers with, for example, trehalose as part of the backbone, so called condensation homopolymers or copolymers, cannot be prepared with an end group that can be used to attach to biomolecules. This is useful for making conjugates with biomolecules.

The present invention also demonstrates that homopolymers or copolymers, which were covalently attached to biomolecules show better stabilization properties than the homopolymers or copolymers which were added non-covalently to biomolecules at the same concentration. Conjugating a trehalose-based homopolymer or copolymer directly to the biomolecule also has the advantage of employing the minimum required amount for stabilization. In addition, for therapeutics, a trehalose-based biomolecules-homopolymer or copolymer conjugate could combine the advantages of environmental stabilization due to trehalose with improved pharmacokinetics resulting from the homopolymer or the copolymer.

Furthermore, previously described trehalose-based homopolymers or copolymers could not be prepared with narrow molecular weight distributions, which is readily achieved by the methods disclosed herein. Finally, the protective properties of trehalose are based on the hydroxyl functionality as well as the clam shell shape of the molecule. When the sugar, e.g., trehalose, is incorporated into a backbone, rather than free as a side chain, the protective properties are likely compromised.

The homopolymers or copolymer disclosed herein may be prepared with a reactive group at one end for conjugation to biomolecules, and the homopolymers or copolymers have narrow molecular weight distributions. This is not possible utilizing previously reported procedures. Different molecular weights have different toxicities, solubilities, and pharmokinetic properties, thus narrow molecular weight distributions are important. Indeed, few homopolymers or copolymers have been reported to stabilize proteins to environmental stressors, and these do not contain sugars (e.g., trehalose) as a side chain.

In certain preferred embodiments, the disclosed homopolymers or copolymers are attached to biomolecules utilized as drugs. Addition of the nonconjugated homopolymer or copolymers to biomolecules alone or combination with other formulation agents is another example of a use for the disclosed homopolymers or copolymers. The homopolymers or copolymers may also be employed to stabilize proteins and other biologics used solely for research purposes. Applicants envision that the disclosed homopolymers or copolymers may also be useful in other diverse applications such as healthcare (pharmaceuticals), molecular biology, biofuels, paper, detergent, personal care (diapers where the polymers are very hydroscopic), photographic, rubber, brewing, dairy and food (additives) processing industries.

The following examples are offered for illustrative purposes only, and are not intended to limit the scope of the present invention in any way. Indeed, various modifications of the disclosed method in addition to those shown and described herein will become apparent to those skilled in the art from the foregoing description and the following examples and fall within the scope of the appended claims.

Definitions

Before the composition and related methods are described, it is to be understood that this invention is not limited to the particular methodology, protocols, materials, and reagents described, as these may vary. The terminology used herein is for the purpose of describing particular embodiments only, and is not intended to limit the scope of the present invention which will be limited only by any later-filed non-provisional applications.

The invention described herein provides a means for stabilizing biomolecules by protecting or maintaining the structure using effective amounts of trehalose covalently bonded to homopolymers or copolymers conjugated to the biomolecules.

According to one embodiment of the invention, a trehalose-based homopolymer or copolymer is used to stabilize protein against aggregation, conformational changes and/or degradation, such as denaturation of native protein or renaturation of denatured (unfolded or partially folded) protein, helping to maintain the protein in the desired configuration in a hostile or stressful environment, and intended function is maintained to be at least equal to the protein in its natural states or is enhanced over a reduced activity that the protein would have in the stressful environment. A trehalose-based homopolymer or copolymer will act to stabilize proteins against degradation, e.g. by heat, electromagnetic radiation, shear stress, proteolysis, or by chemical modification such as reduction, oxidation, or carbamoylation. In methods of the invention, a trehalose-based homopolymer or copolymer may be used to stabilize a protein in aqueous solution, or in dry form, e.g. produced by desiccation, dehydration, evaporation or lyophilisation (freeze drying) of an aqueous solution.

The term "aryl" refers to a carbocyclic (non-heterocyclic or heterocyclic) aromatic ring or mono-, bi- or tri-cyclic ring system. The aromatic ring or ring system is generally composed of 6 to 10 carbon atoms. Examples of aryl groups include but are not limited to phenyl, biphenyl, naphthyl and tetrahydronaphthyl. 6-membered aryls such as phenyl are preferred.

The term "alkyl" refers to optionally substituted straight chain or branched chain hydrocarbon groups. Examples include methyl (Me), ethyl (Et), propyl (Pr), isopropyl (i-Pr), butyl (Bu), isobutyl (i-Bu), sec-butyl (s-Bu), tert-butyl (t-Bu), pentyl, neopentyl, hexyl and the like. Unless the context requires otherwise, the term "alkyl" also encompasses alkyl groups containing one less hydrogen atom such that the group is attached via two positions, i.e., divalent. "$C_{1-4}$alkyl" and "$C_{1-3}$alkyl" including methyl, ethyl, propyl, isopropyl, n-butyl, iso-butyl, sec-butyl and tert-butyl are preferred with methyl being particularly preferred.

"Stressful environment" means an environment which will reduce a functional property or activity of a biomolecule. For example, the environment may reduce a functional property or activity of a protein over a native protein or that which the protein has in its natural state. A stressful environment may include temperatures which create adverse thermal environments which could be elevated or reduced temperatures, solvents such as an organic solvent, the presence of proteases, pH and/or lack of buffer.

The term "biomolecule" as used herein refers, but is not limited to proteins, enzymes, antibodies, DNA, siRNA, and pharmaceutical compositions. Such biomolecules are subject to environmental stresses which include but are not limited to heat, desiccation, light, storage, exposure to enzymes, endo- and exo-nucleases and pH variation.

The term "protein" used herein refers to any compound of two or more individual amino acids (whether or not naturally occurring) linked via peptide bonds, as occur when the carboxyl carbon atom of the carboxylic acid group bonded to the α-carbon of one amino acid (or amino acid residue) becomes covalently bound to the amino nitrogen atom of the amino group bonded to the α-carbon of an adjacent amino acid. These peptide bond linkages, and the atoms comprising them (i.e., α-carbon atoms, carboxyl carbon atoms (and their substituent oxygen atoms), and amino nitrogen atoms (and their substituent hydrogen atoms)) form the "polypeptide backbone" of the protein. In addition, as used herein, the term "protein" is understood to include the terms "polypeptide" and "peptide." Similarly, protein fragments, analogs, derivatives, and variants are may be referred to herein as "proteins," and shall be deemed to be a "protein" unless otherwise indicated. The term "fragment" of a protein refers to a polypeptide comprising fewer than all of the amino acid residues of the protein. As may be appreciated, a "fragment" of a protein may be a form of the protein truncated at the amino terminus, the carboxyl terminus, and/or internally (such as by natural splicing), and may also be variant and/or derivative. A "domain" of a protein is also a fragment, and comprises the amino acid residues of the protein required to confer biochemical activity corresponding to naturally occurring protein. The term "protein" used herein also include "protein conjugate" which refers to a compound complex comprising a "protein" which is interlinked to one another molecule or subject. The term "complex" is used herein to mean those compounds comprising at least two components. The protein may be naturally occurring and isolated from its source. The protein may be produced using DNA recombination or mutation techniques. The protein may be produced in vivo in a whole animal, or in a eukaryotic or prokaryotic cell; alternatively, the protein may be generated using an in vitro method such as cell-free in vitro translation, e.g., using *E. coli* lysate, wheat germ extract, or rabbit reticulocyte. Cell free in vitro translation methods can be employed following in vitro transcription, e.g., following phage or ribosome display.

Examples of proteins include, without limitation, Lysozyme, Adenosine deaminase, L-Asparaginase, Mammalian urate oxidase, Interferons, Anti-TNF a Fab, granulocyte colony stimulated factor (G-CSF), Continuous erythropoietin receptor activator, hGH antagonist B2036, Insulin, Insulin human inhalation, Insulin aspart, Insulin glulisine, Insulin lispro, Isophane insulin, Insulin detemir, Insulin glargine, Insulin zinc extended, Pramlintide acetate, Growth hormone (GH), Somatotropin, Mecasermin, Mecasermin rinfabate, Factor VIII. Factor IX, Antithrombin III (AT-iii), fibroblast growth factor (FGF), basic fibroblast growth factor (bFGF), vascular endothelial growth factor (VEGF), platelet derived growth factor (PDGF), Protein C concentrate, β-Gluco-cerebrosidase, Alglucosidase-α, Laronidase (α-L-iduronidase), Idursulphase (iduronate-2-sulphatase), Galsulphase, Agalsidase-β (human α-galactosidase A), α-1-Proteinase inhibitor, Lactase, Pancreatic enzymes, lipase, amylase, protease, Adenosine deaminase, Pooled immunoglobulins, Human albumin, Erythropoietin, Epoetin-α, Darbepoetin-α, Sargramostim (granulocytemacrophage colony stimulating factor; GM-CSF), Oprelvekin (interleukinll; IL11) Human follicle-stimulating hormone (FSH), Human chorionic gonadotropin (HCG), Lutropin-α, Type I alpha-interferon, interferon alfacon 1, consensus interferon, Aldesleukin (interleukin 2 (IL2), epidermal thymocyte activating factor (ETAF), Alteolase (tissue plasminogen activator: tPA), Reteplase (deletion mutein of tPA), Tenecteplase, Urokinase, Factor VIIa, Drotrecogin-α (activated protein C), Salmon calcitonin, Teriparatide (human parathyroid hormone residues 1-34), Exenatide, Octreotide, Dibotermin-α (recombinant human bone morphogenic protein 2; rhBMP2), Recombinant human bone morphogenic protein 7 (rhBMP7), Histrelin acetate (gonadotropin releasing hormone; GnrH), Palifermin (keratinocyte growth factor; KGF), Becaplermin (platelet-derived growth factor; PDGF), Trypsin, Nesiritide, Botulinum toxin type A, Botulinum toxin type B, Collages, Collagenase, Human deoxyribonuclease I, dornase-α, Hyaluronidase (bovine, ovine), Hyaluronidase (recombinant human), Papain, L-Asparaginase, Rasburicase, Lepirudin, Bivalirudin, Streptokinase, Anistreplase (anisoylated plasminogen streptokinase activator complex; APSAC), Bevacizumab, Cetuximab, Panitumumab, Alemtuzumab, Rituximab, Trastuzumab, Abatacept Anakinra, Adalimumab, Etanercept, Infliximab, Alefacept, Efalizumab, Natalizumab, Eculizumab, Antithymocyte globulin (rabbit), Basiliximab, Daclizumab, Muromonab-CD3, Omalizumab, Palivizumab, Enfuvirtide, Abciximab, Crotalidae polyvalent immune Fab (ovine), Digoxin immune serum Fab (ovine), Ranibizumab, Denileukin diftitox, Ibritumomab tiuxetan, Gemtuzumab ozogamicin, Tositumomab, and itositumomab.

A denatured protein can be fully denatured, or partially denatured or renatured such that the protein is in non-native form as unfolded protein and/or partially folded refolding intermediate(s). An aqueous solution or dried sample comprising denatured protein may contain one or more of these forms. A native protein is in a folded, functional conformation. Some protein may also be present in aqueous solution, or in a dried sample, in the form of contaminating aggregates and/or inclusion bodies.

The term "stability" refers to the maintenance of a protein or other biomolecule's native bioactivity function after storage. The present invention will provide stability of at least 70%, and preferably at least 80%, of the protein's function as compared to storage without a trehalose stabilizing agent under identical environmental conditions. It is envisioned that, for example, when a protein like insulin is conjugated with a trehalose-based polymer or copolymer as described here, the insulin protein retains at least 70%, 75%, 80%, 85%, 90% or greater percentage of its native bioactivity compared to insulin by itself, which may retain only 20% of its original bioactivity at best. Those skilled in the art appreciate that the percent of bioactivity that is retained is protein and stress dependent. Furthermore, the length of time that a conjugated protein is able to maintain its bioactivity or function compared to a naked/unmodified protein varies depending on the environmental stressors it is subjected to. It is envisioned the conjugated proteins as described here can retain bioactivity for at least 5, 10, 20, 30, 40, 50, 60, 70, 80, 90, or 100 times longer than an unconjugated native protein under identical environmental conditions.

The term "antibody" or "antibody molecule" as used herein refers to immunoglobulin molecules or other molecules which comprise an antigen binding domain. The term "antibody" or "antibody molecule" as used herein is thus intended to include whole antibodies (e.g., IgG, IgA, IgE, IgM, or IgD), monoclonal antibodies, polyclonal antibodies, and chimeric antibodies.

The terms "monoclonal antibody" or "monoclonal antibody composition" as used herein refer to a preparation of antibody molecules of a single amino acid composition. The monoclonal antibody also includes "human monoclonal antibody" which refers to antibodies displaying a single binding specificity which have variable and constant regions derived from human germline immunoglobulin sequences. The human monoclonal antibodies can be produced by a hybridoma which includes a B cell obtained from a transgenic nonhuman animal, for example, a transgenic mouse, having a genome comprising a human heavy chain trans gene and a light human chain transgene fused to an immortalized cell.

The term "chimeric antibody" refers to a monoclonal antibody comprising a variable region, i.e., binding region, from one source or species and at least a portion of a constant region derived from a different source or species, usually prepared by recombinant DNA techniques. Chimeric antibodies can also comprise a murine variable region and a human constant region. Such murine/human chimeric antibodies are the product of expressed immunoglobulin genes comprising DNA segments encoding murine immunoglobulin variable regions and DNA segments encoding human immunoglobulin constant regions. Other forms of "chimeric antibodies" are those in which the class or subclass has been modified or changed from that of the original antibody. Such "chimeric" antibodies are also referred to as "class-switched antibodies." Methods for producing chimeric antibodies involve conventional recombinant DNA and gene transfection techniques now well known in the art.

The term "antibody" also shall include humanized antibody, human antibody and recombinant human antibody. The term "humanized antibody" refers to antibodies in which the framework or "complementarity determining regions" (CDR) have been modified to comprise the CDR of an immunoglobulin of different specificity as compared to that of the parent immunoglobulin. In a preferred embodiment, a murine CDR is grafted into the framework region of a human antibody to prepare the "humanized antibody." Particularly preferred CDRs correspond to those representing sequences recognizing the antigens noted above for chimeric and bifunctional antibodies.

The term "human antibody" includes antibodies having variable and constant regions derived from human germline immunoglobulin sequences. The variable heavy chain is preferably derived from germline sequence DP-50 and the variable light chain is derived from germline sequence L6. The constant regions of the antibody are constant regions of human IgG 1 type.

The term "recombinant human antibody" includes all human antibodies that are prepared, expressed, created or isolated by recombinant means, such as antibodies isolated from a host cell such as an SP2-0, NSO or CHO cell (like CHO K1) or from an animal (e.g., a mouse) that is transgenic for human immunoglobulin genes or antibodies expressed using a recombinant expression vector transfected into a host cell. Such recombinant human antibodies have variable and constant regions derived from human germline immunoglobulin sequences in a rearranged form.

The term "antibody" also includes "antibody fragments" or "antibody-derived fragments" which comprise an antigen binding domain are also included. The term "antibody fragment" as used herein is intended to include any appropriate antibody fragment that displays antigen binding function, for example, Fab, Fab', F(ab')$_2$, scFv, Fv, dsFv, ds-scFv, Fd, dAbs, TandAbs dimers, mini bodies, monobodies, diabodies, and multimers thereof and bispecific antibody fragments. Antibodies can be fragmented using conventional techniques. For example, F(ab')$_2$ fragments can be generated by treating the antibody with pepsin. The resulting F(ab')$_2$ fragment can be treated to reduce disulfide bridges to produce Fab' fragments. Papain digestion can lead to the formation of Fab fragments. Fab, Fab' and F(ab')$_2$, scFv, Fv, dsFv, Fd, dAbs, TandAbs, ds-scFv, dimers, minibodies, diabodies, bispecific antibody fragments and other fragments can also be synthesized by recombinant techniques or can be chemically synthesized. Techniques for producing antibody fragments are well known and described in the art.

The antibodies or antibody fragments can be produced naturally or can be wholly or partially synthetically produced. Thus the antibody may be from any appropriate source, for example recombinant sources and/or produced in transgenic animals or transgenic plants. Thus, the antibody molecules can be produced in vitro or in vivo. Preferably the antibody or antibody fragment comprises an antibody light chain variable region ($V_L$) and an antibody heavy chain variable region ($V_H$) which generally comprise the antigen binding site. The antibody or antibody fragment can comprises all or a portion of a heavy chain constant region, such as an IgG1, IgG2, IgG3, IgG4, IgA1, IgA2, IgE, IgM or IgD constant region. Preferably, the heavy chain constant region is an IgG1 heavy chain constant region. Furthermore, the antibody or antibody fragment can comprise all or a portion of a kappa light chain constant region or a lambda light chain constant region. All or part of such constant regions may be produced naturally or may be wholly or partially synthetic. Appropriate sequences for such constant regions are well known and documented in the art.

The term "fragment" as used herein refers to fragments of biological relevance (functional fragment), e.g., fragments which can contribute to or enable antigen binding, e.g., form part or all of the antigen binding site, or can contribute to the inhibition or reduction in function of the antigen or can contribute to the prevention of the antigen interacting with its natural ligands. Fragments thus comprise a heavy chain variable region ($V_H$ domain) and/or a light chain variable region ($V_L$ domain) of the antibodies of the invention. Fragments may also comprise one or more of the heavy chain complementarity determining regions (CDRs) of the antibodies or of the $V_H$ domains, or one or more of the light chain complementarity determining regions (CDRs) of the antibodies, or of the $V_L$ domains.

The term "sugar polymer" as used herein encompasses polymeric and oligomeric saccharide molecules comprising three or more mono-, di- or tri-saccharide units. The sugar polymer can be a linear or non-linear amphipathic sugar polymer derivative. Specifically, sugar polymers comprise one or more sugar(s) including, without limitation, trehalose, erythrose, threose, ribose, arabinose, xylose, lyxose, allose, altrose, glucose, mannose, gulose, idose, galactose, talose, psicose, fructose, sorbose, tagatose, xylulose and ribulose. The sugar polymers can be a dextran, cellulose, amylose, starch, pullulan, mannan, chitin, chitosan, inulin, levan, xylan, cyclodextrin (provided that it is not an alpha, beta or gamma cyclodextrin), cycloamylose or a derivative thereof.

Sugar polymers, specifically trehalose-based homopolymer or copolymers suitable for use in the invention are those which, at an appropriate concentration and in appropriate conditions, can (1) maintain a native biomolecule in its native state to retain a functional property of the native biomolecule in a stressful environment or (2) maintain a denatured biomolecule in a non-native state as desired by the researcher. Suitable trehalose-based homopolymer or copolymers are those which are capable of shielding hydrophobic amino acid side chains or modifying the net biomolecule charge or hydrogen bonding characteristics. Suitable trehalose-based homopolymer or copolymers may also comprise those capable of water entrapment, or those having hydrogen bonding characteristics.

EXAMPLES

Example 1: Trehalose Glycopolymers for Stabilization of Protein Conjugates to Environmental Stressors Procedures, Results, and Discussion.

As an illustrative example of the disclosed homopolymer or copolymer, the polymerizable trehalose monomer was first prepared in two steps (Scheme 1). Terephthaldehyde monodiethylacetal was employed to form 1 via a Wittig reaction in 97% yield. This in turn was used to effect a transacetal reaction with trehalose exclusively at the 4,6 position under slightly acidic conditions affording 4,6-O-(4-vinylbenzyl)-α-D-glucopyranosyl-(1→1)-α-D-glucopyranoside (2) in 41% yield. No other isomers were observed indicating that preference for the 4,6 position was retained for the substituted benzaldehyde diethylacetal. The $^1$H NMR and $^{13}$C NMR, are provided in FIG. 1. Heteronuclear single quantum coherence total correlation spectroscopy (HSQC-TOCSY) experiments were performed to verify both the selectivity of the reaction as well as the integrity of the product ring systems. Furthermore, NOESY NMR was undertaken to demonstrate retention of the unique confirmation of the native disaccharide whereby the two glucose subunits are held in a rigid clamshell shape about the α,α-1,1-glycosidic linkage. This result is important as it has proven to be a critical component in generating the unique physicochemical and protective properties of the carbohydrate (Sakurai, Murata, et al., 1997).

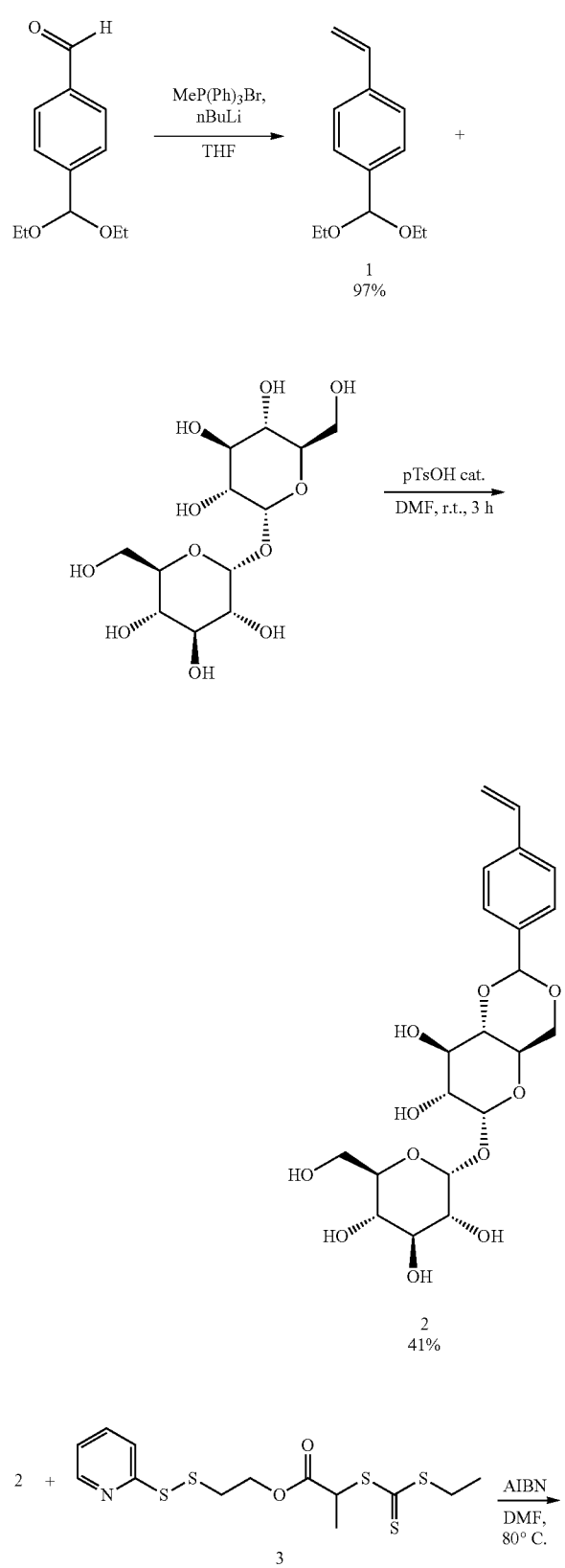

Scheme 1. Synthesis of illustrative trehalose monomer and subsequent polymerization of the monomer by RAFT to form the polymer.

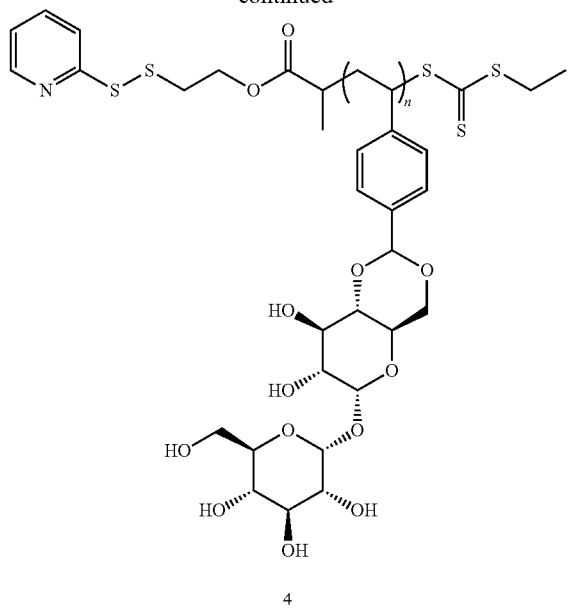

4

Scheme 1. Synthesis of Illustrative Trehalose Monomer and Subsequent Polymerization of the Monomer by RAFT to Form the Polymer.

The styrene monomer is shown in this example, yet any other polymerizable monomers including, but not limited to, acrylate, methacrylate, acrylamide, methacrylamide, vinyl, norborenyl, and strained cycle alkene can be employed. In addition, the monomer may be linked to the trehalose through —OH groups at any position.

Reversible addition-fragmentation (RAFT) polymerization was used to prepare the polymer in this illustrative example, although a number of other techniques could be employed, including but not limited to atom transfer radical polymerization (ATRP), nitroxide mediated polymerization (NMP), cyanoxyl-mediated free radical polymerization, conventional radical polymerization and ring opening metathesis polymerization (ROMP). The CTA 3 was prepared with a pyridyl disulfide group. However any CTAs may be utilized, as well as corresponding functionalized initiators for ATRP, NMP, cyanoxyl-mediated, conventional radical polymerization and catalysts and functionalized alkenes for ROMP.

Figure 2:
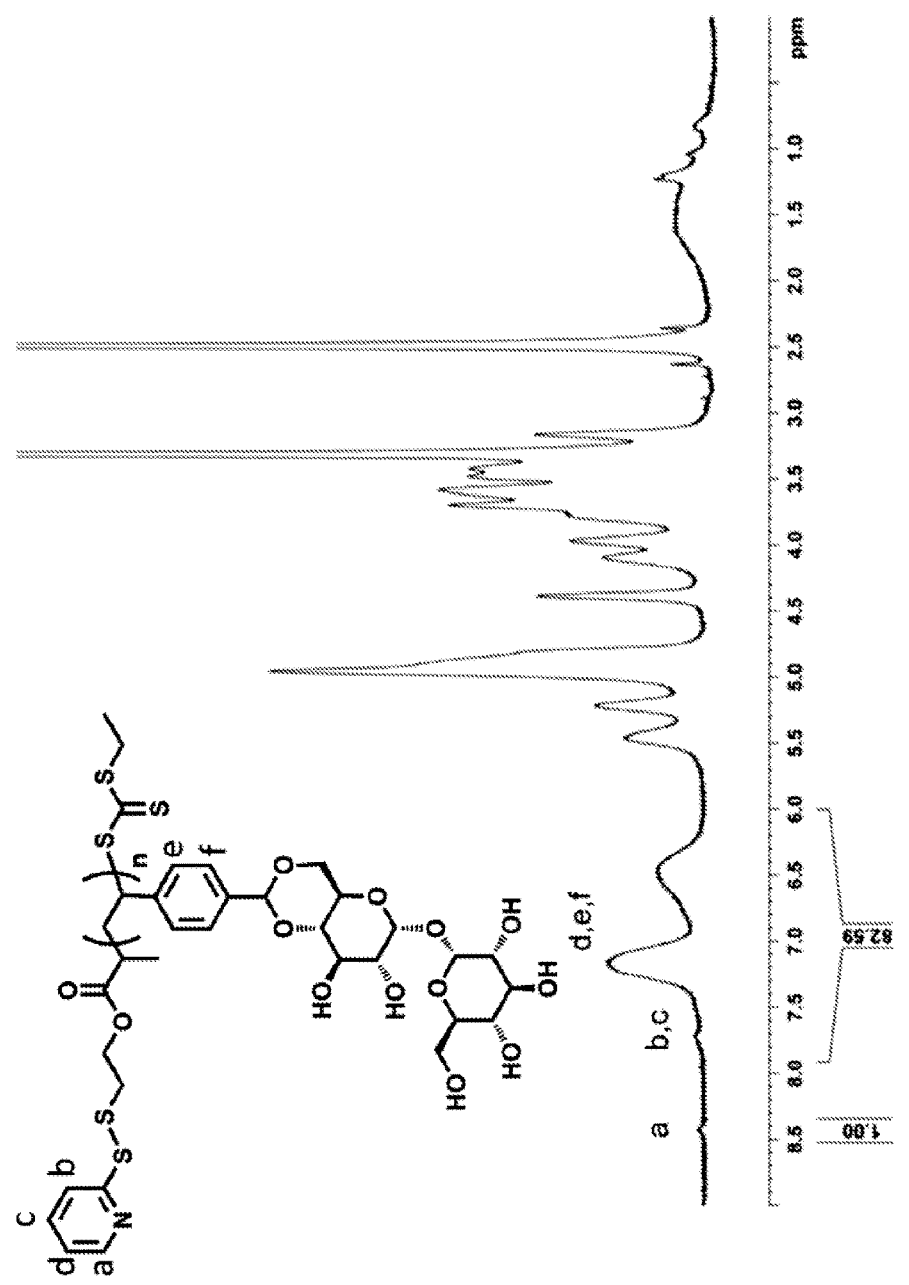
FIG. 2 is $^1$H NMR spectroscopy of trehalose polymer 4 (D6-DMSO).

RAFT polymerization of 2 with 3 was performed at 80° C. (Scheme 1). The ratio used for polymerization was [CTA]:[monomer]:[AIBN]=1:29:0.2, with a concentration of 0.8 M monomer. After 6 h, the polymerization was stopped to obtain a 77% conversion. The homopolymer 4 was dialyzed against aqueous sodium bicarbonate with a MWCO 2,000 g/mol. The molecular weight of 4 was analyzed by $^1$H NMR (FIG. 2) spectroscopy and was 9,600 g/mol by comparing the integration of the end-group pyridine peaks (a, b, c, d) to the aromatic ring from styrene (e, f). The PDI by GPC was 1.07, demonstrating that a well-defined polymer was formed. Other molecular weights are readily obtained. To demonstrate this, the [CTA]:[monomer]:[AIBN] ratios were then altered to obtain other molecular weights ranging from 4,200 g/mol to 19,000 g/mol (Table 1) with narrow PDIs obtained in all cases; although a narrow PDI is not required.

TABLE 1

Polymerization results of 2 by RAFT polymerization with 3. Polymerizations were conducted in DMF at 80° C. with 0.08M monomer concentration for all trials.

| CTA:M:AIBN | Target $M_n$ | Conv (%) | $M_n$ (H NMR) | PDI |
|---|---|---|---|---|
| 1:21:0.2 | 7,000 | 72 | 4,200 | 1.05 |
| 1:29:0.2 | 9,600 | 77 | 9,400 | 1.07 |
| 1:35:0.2 | 13,800 | 84 | 14,700 | 1.11 |
| 1:50:0.2 | 20,000 | 85 | 19,000 | 1.14 |

CTAs with pyridyl disulfides and different structures may also be utilized and/or with different reactive groups including but not limited to activated esters, maleimides (may also be protected or substituted), vinyl sulfones (may also be protected or substituted), ketones, aldehydes or any other oxo group, amines, hydroxyl amines, hydrazines, azides, alkynes. As an illustrative example, CTA 5 with a hydrophilic triethylene glycol spacer between the trithiocarbonate and pyridyl disulfide end-group was prepared (Scheme 2). Tri(ethylene glycol) (TEG) was modified by tosylation followed by refluxing with thiourea (Steinem, C. et al. Valinomycin-mediated transport of alkali cations through solid supported membranes. *Bioelectrochemistry and Bioenergetics* 45, 17-26 (1998)). The resulting 1-mercapto triethylene glycol was treated with Aldrithiol® to obtain the activated disulfide with subsequent carbodiimide mediated coupling to the acid moiety on 2-(ethyl sulfanylthiocarbonyl sulfanyl)-propionic acid affording the thiol reactive chain transfer agent 5 in 9% yield over five linear steps.

Scheme 2. Synthesis of thiol reactive chain transfer agent 5.

Figure 3:
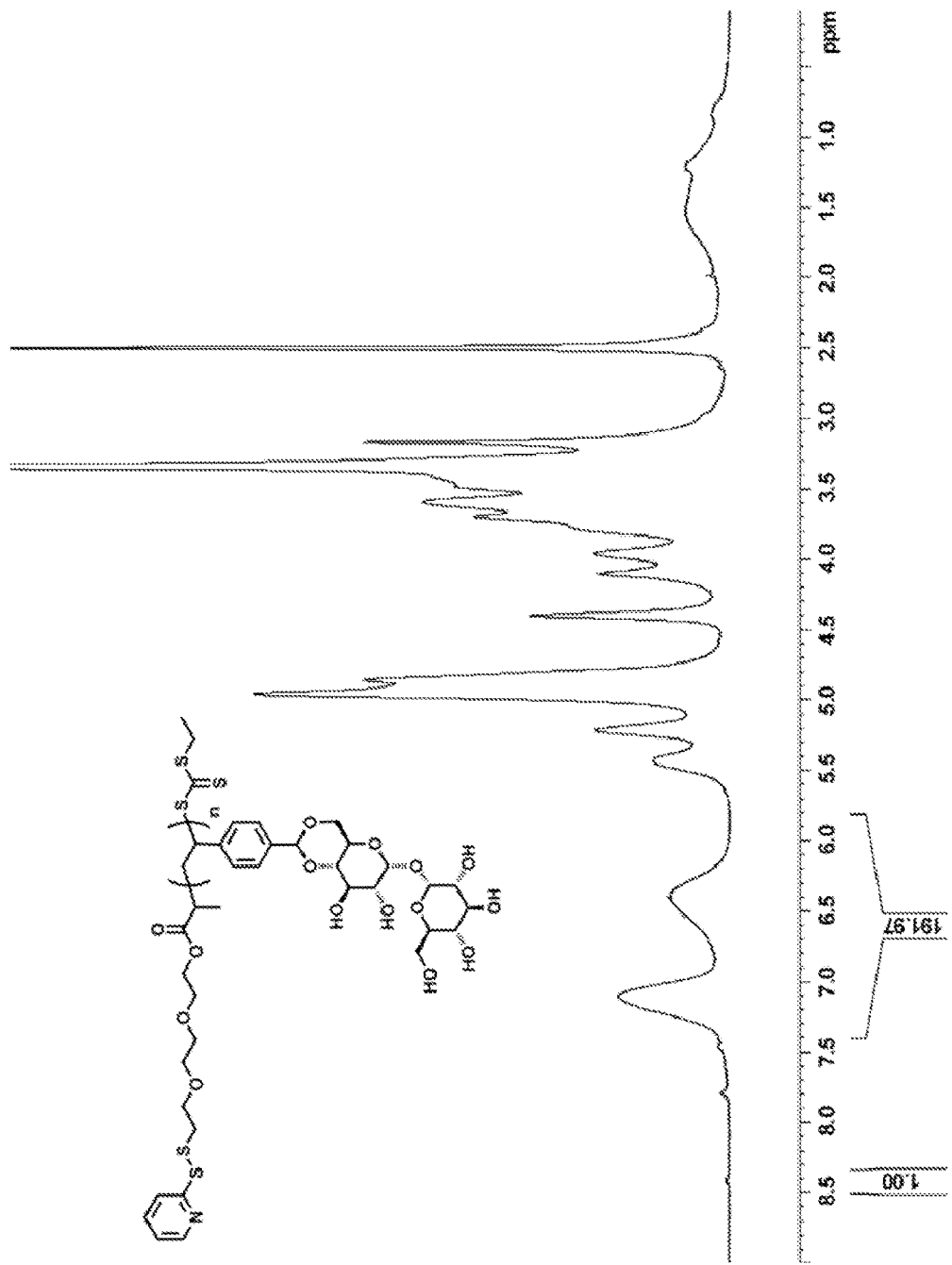
FIG. 3 is $^1$H NMR spectroscopy of glycopolymer made in the presence of 5 (D6-DMSO).

RAFT polymerization of 2 in the presence of 5 (Scheme 3) was shown to proceed to 92% conversion over six hours to result in a polymer with well defined molecular weight Mn=22.4 kDa (NMR) and PDI=1.10 (GPC) ($^1$H NMR provided as FIG. 3). If removal of the trithiocarbonate end group is desired, this can be accomplished by radical exchange with excess AIBN (Perrier, S., Takolpuckdee, P. & Mars, C. A. Reversible addition-fragmentation chain transfer polymerization: End group modification for functionalized polymers and chain transfer agent recovery. *Macromolecules* 38, 2033-2036 (2005)) to produce homopolymer 6 (Scheme 3) or the polymer may be reduced to the thiol and reacted with any number of reagents. In addition, the invention claims polymers with any end group, including those that react with other areas of proteins. This includes, but is not limited to, end groups that react with amines, carboxylic acids, alcohols, non-natural amino acid functionality such as click chemistry partners (azides, alkynes, hydroxyl amines, oxo groups, hydrazines, etc.), ligand binding sites. As an illustrative example, a CTA with a ketone was synthesized (Scheme 4) in two steps. This CTA was utilized to prepare an amine-reactive polymer (Scheme 5). The resulting polymer had a Mn of 10.9 kDa (NMR) and a PDI of 1.42 by GPC.

Scheme 3. RAFT Polymerization and removal of the trithiocarbonate end group form homopolymer 6.

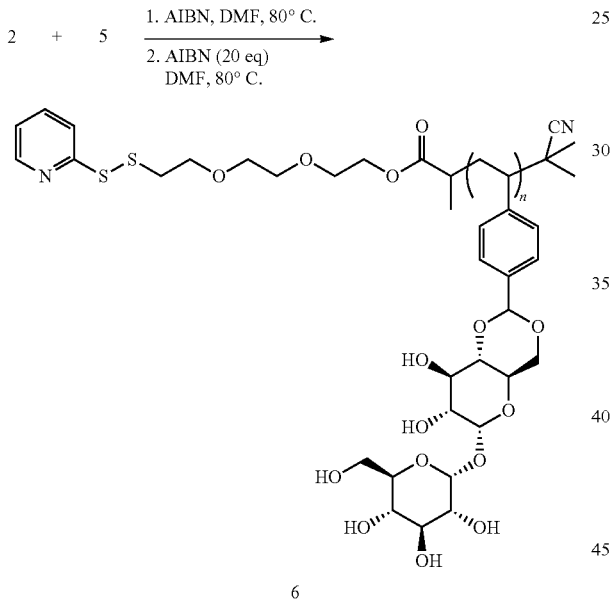

Scheme 4. Amine reactive CTA synthesis.

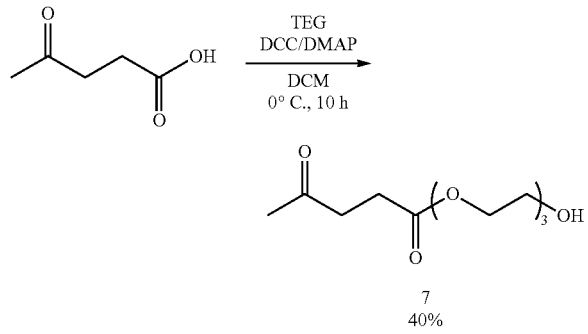

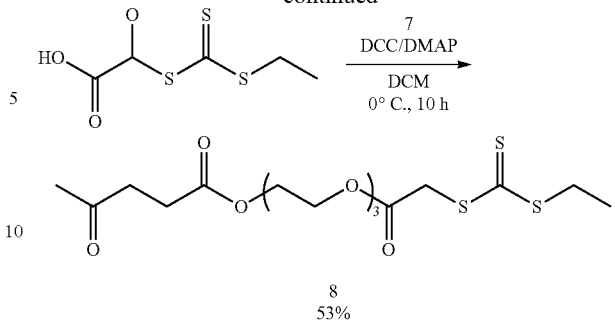

Scheme 5. RAFT polymerization with CTA 8 to form amine reactive polymer 9.

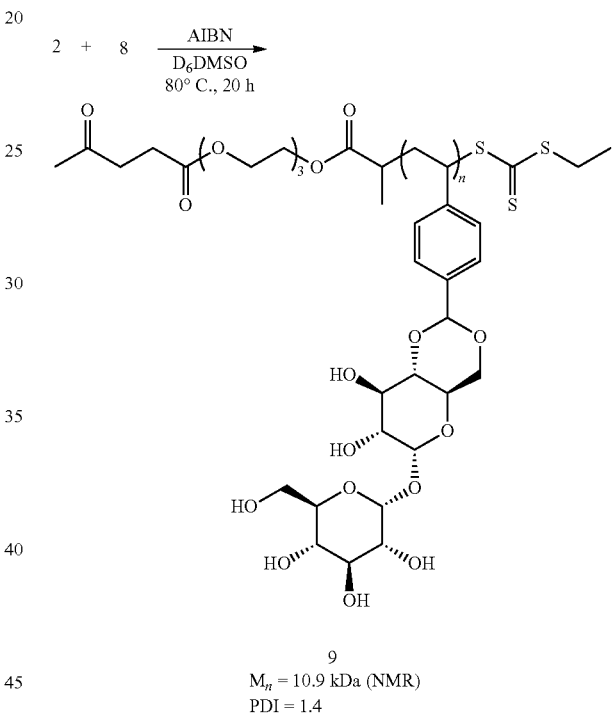

Conjugation of Polymer to Proteins.

Figure 35:
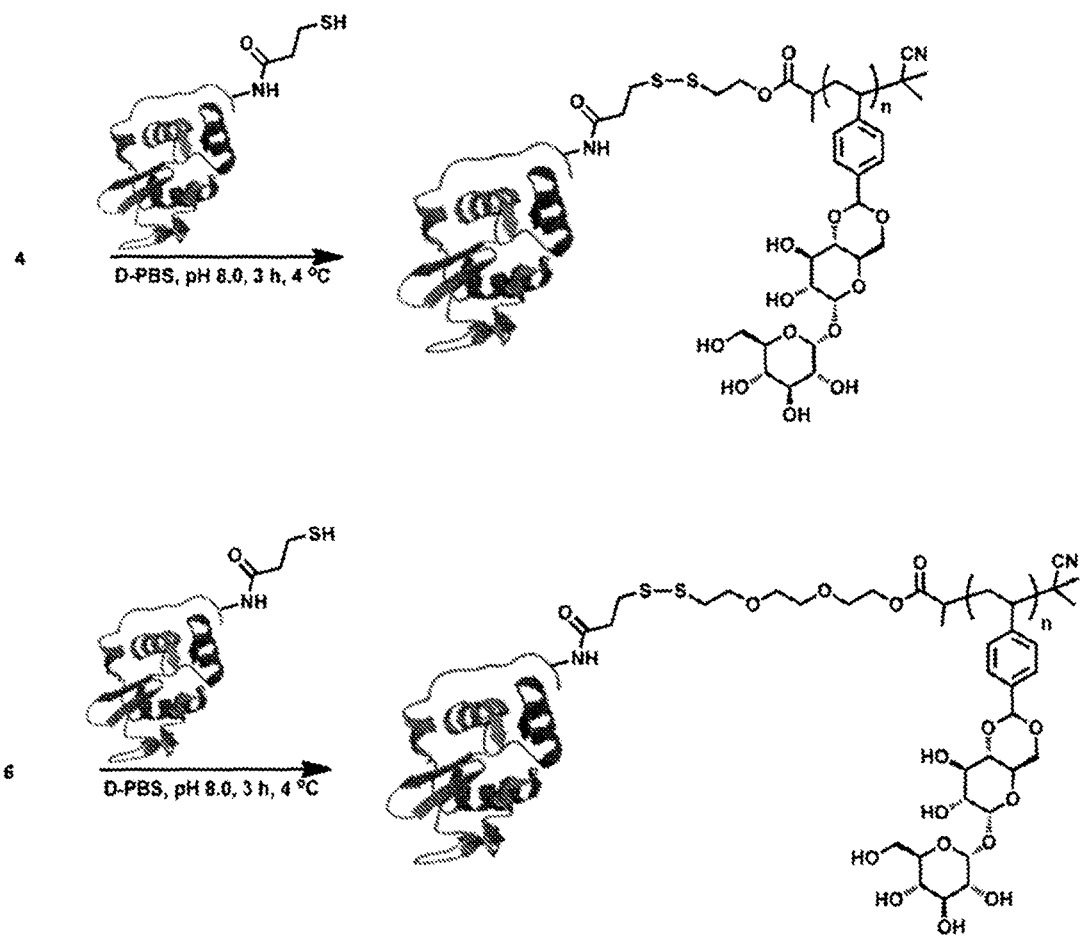
FIG. 35 shows Scheme 6. Illustrative conjugation reactions of thiolated lysozyme with polymer 4 and polymer 6 to form the respective conjugates.

The trehalose-based homopolymers 4 ($M_n$=9,400 g/mol) and 6 were conjugated to thiolated lysozyme (LyzSH, Scheme 4) as a model protein and illustrative example for this invention (FIG. 35 Scheme 6). Any number of proteins, enzymes, antibodies, DNA, siRNA, other biomolecules and drugs may be utilized as conjugation partners. Hen egg white lysozyme was treated with succinimidyl acetyl-thiopropionate (SATP) in a procedure known to covalently attach thioacetate functionality to proteins via amide bonds (Hermanson, 1996). After deprotection with hydroxyl amine and removal of excess SATP, free thiols were quantified on the thiolated lysozyme (LyzSH) by Ellman's assay resulting in a thiol:protein ratio of 1:1.4 (71% thiol). After incubation with the trehalose polymer, conjugate was observed by SDS-PAGE (not shown) under non-reducing conditions as a smear centered at ~25 kDa corresponding to the theoretical molecular weight of conjugate. Polymer 6 was also conjugated to the same protein (LyzSH). The resulting lysozyme-glycopolymer conjugate (Lyz-6) was purified by fast protein liquid chromatography (FPLC) (FIG. 4a). Activity of the purified Lyz-6 conjugate was confirmed by observing active lysis of the FITC labeled gram positive bacteria *Micrococcus luteus* (FIG. 4b). Conjugation was verified by SDS-PAGE (FIG. 4c-e).

Figure 5:
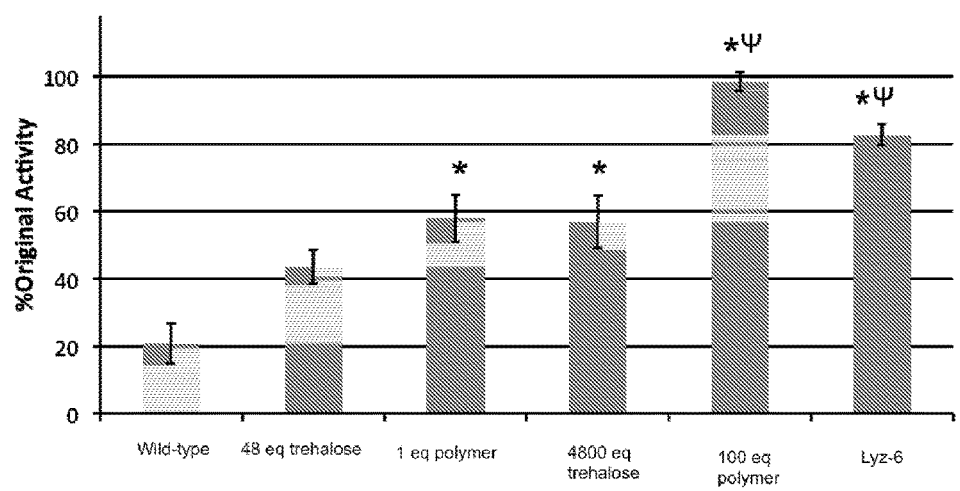
FIG. 5 shows desiccation stability of wild-type lysozyme with and without added trehalose and polymer and conjugate Lyz-6. Samples were treated with 10 lyophilization cycles and compared to untreated protein. (*,$^\psi$,$^\times$, $p<0.05$ compared to wild-type lysozyme, lysozyme treated with 1 eq of trehalose, and lysozyme treated with 1 eq of polymer respectively). Note that in these experiments, the lysozyme was considerably more concentrated than in FIG. 7.

Samples of Lyz-6 and wild-type lysozyme alone or with added trehalose or nonconjugated polymer 6 were then exposed to environmental stresses in an identical fashion and assayed for activity (FIG. 5). Samples of Lyz-6 conjugate exposed to 10 lyophilization cycles (i.e. desiccation) had 80% of the activity of unexposed Lyz-6 that had been stored at 4° C., whereas wild-type lysozyme retained only ~20% of the original activity under identical conditions. Therefore, conjugating the polymer covalently to the protein significantly improves the stability of the protein. Samples containing 1 equivalent of unconjugated polymer to protein stabilized the protein to ~60% activity and 100 equivalents of unconjugated polymer to protein fully stabilized the biomolecule (100% activity). Trehalose was added to wild-type lysozyme at 48 equivalents to protein, which is equivalent to the amount of trehalose in 1 equivalent of polymer. Trehalose with 4800 equivalents is the same amount of trehalose as in 100 equivalents of polymer, and this was added to the protein in a separate sample. In both cases the added, unconjugated glycopolymer was found to stabilize the protein significantly better than equivalent amounts of added trehalose, demonstrating that free polymer is a more effective cryo-protectant than trehalose.

Figure 6:
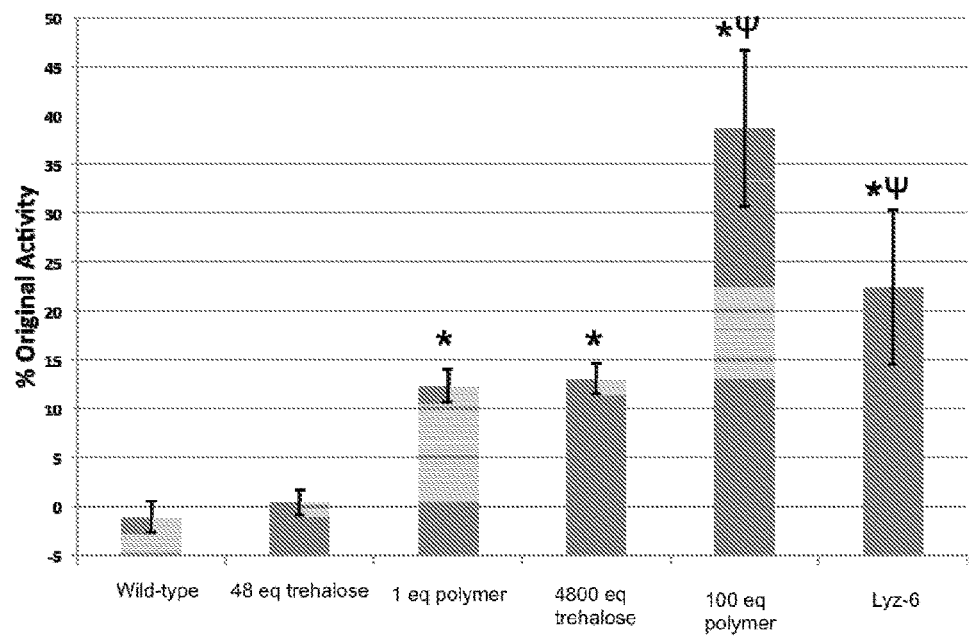
FIG. 6 shows heat stability (exposed to 90° C. heat burden for 3 h) of wild-type lysozyme, Lyz-6 lysozyme-glycopolymer conjugate, wild-type lysozyme formulated with various concentrations of glycopolymer or trehalose. (*,$^\psi$ $p<0.05$ compared to wild-type lysozyme, and lysozyme treated with 100 eq of trehalose respectively). Note that in these experiments, the lysozyme was considerably more concentrated than in FIG. 8.

To investigate thermal stability, samples were exposed to a heat burden of 90° C. for 3 hours and assayed for remaining activity (FIG. 6). Although no activity remained in the wild-type lysozyme, >20% activity was retained by conjugating the polymer to the protein (Lyz-6). The free polymer added to the wild-type lysozyme also significantly stabilized the protein and stabilized better (i.e. protein activity was higher) than equivalent amounts of added trehalose. This result shows that the glycopolymer stabilizes biomolecules to high temperatures both added in solution and covalently attached as a conjugate.

Experimental Details

Materials. All solvents were purchased from Fisher Scientific (Pittsburgh, Pa.) and used without further purification unless otherwise noted. Trehalose was purchased from The Endowment for Medical Research, (Houston, Tex.) and rendered anhydrous prior to use via known procedures (Reisener, H. J., Perlin, A. S., Ledingham, G. A. & Goldschmid, H. R. FORMATION OF TREHALOSE AND POLYOLS BY WHEAT STEM RUST (*PUCCINIA GRAMINIS TRITICI*) UREDOSPORES. *Canadian Journal of Biochemistry and Physiology* 40, 1248-& (1962)). The starting compound 1-mercaptotriethylene glycol was prepared according to literature procedures (Steinem, C. et al. Valinomycin-mediated transport of alkali cations through solid supported membranes. *Bioelectrochemistry and Bioenergetics* 45, 17-26 (1998)). The EnzChek® lysozyme assay kit was purchased from Invitrogen and used as per manufacturer instructions. Hen egg white lysozyme and all other chemical reagents were purchased from Sigma-Aldrich.

Analytical Techniques.

NMR spectra were recorded on a Bruker Advance 500 or 600 MHz spectrometer. Gel permeation chromatography (GPC) was conducted on a Shimadzu HPLC system equipped with a refractive index detector RID-10A and two Polymer Laboratories PLgel 5 µm mixed D columns (with guard column). Lithium bromide (0.1 M) in N,N-dimethylformamide (DMF) at 40° C. was used as the solvent (flow rate: 0.6 mL/min). Near-monodisperse poly(methyl methacrylate) standards (Polymer Laboratories) were employed for calibration. UV-Visible spectroscopy was performed with a BioMate 5 Spectrophotometer (Thermo Spectronic Instruments). ESI Mass spectra were acquired using a Thermo Finnigan LCQ Deca MS with electrospray ionization source. Infrared spectra were obtained with a Perkin-Elmer Spectrum One instrument equipped with a universal ATR accessory. Preparatory reverse phase HPLC was carried out on a Shimadzu HPLC system equipped with a UV detector using a Luna 5 µm C18 (2) 100A column (preparatory: 5 µm, 250×21.2 mm) with monitoring at λ=254 and 220 nm. A linear gradient water:methanol (40:60 to 10:90) solvent system was used as the mobile phase at a flow rate of 10 mL/min.

Synthesis of Monomers, CTAs, and Polymers

Synthesis of 4-Vinylbenzylacetal (1).

1 was synthesized following a literature procedure (Sun, G. R., Cheng, C. & Wooley, K. L. Reversible addition fragmentation chain transfer polymerization of 4-vinylbenzaldehyde. *Macromolecules* 40, 793-795 (2007)). Methyltriphenylphosphonium bromide (5.4 g, 14.5 mmol) and 45 mL of THF were added to a flame-dried 250 mL round bottom flask. The reaction mixture was cooled to −78° C. and stirred for 20 min. n-BuLi was added drop wise over the course of 20 min. The reaction was stirred for 30 min at −78° C., warmed to 25° C. and stirred for 10 min. The orange-red colored reaction solution was then cooled down to −78° C. Terephthaldehyde monodiethylacetal (2.5 g, 12.0 mmol) dissolved in 7.5 mL of THF was added dropwise over the course of 1 h. After stirring at −78° C. for 30 min, the reaction flask was warmed to 0° C. and stirred for 3 h. Then the reaction warmed to 25° C. and stirred for 1 h. The reaction was quenched by adding 10 mL saturated NaHCO$_3$ solution. The organic layer was collected after adding 50 mL of H$_2$O, and the aqueous layer was extracted with 20 mL of ether three times. The combined organic layers were dried over MgSO$_4$. After purification by silica gel column chromatography with Hex:EtOAc=20:1, 2.40 g of product in liquid form was obtained (97% yield). $^1$H NMR (500 MHz, in CDCl$_3$) δ: 7.55-7.45 (d, J=7 Hz, 2H), 7.45-7.36 (d, J=7 Hz, 2H) 6.78-6.68 (dd, 1H), 5.81-5.74 (d, J=17 Hz, 1H), 5.57-5.51 (s, 1H), 5.29-5.22 (d, J=11 Hz, 1H), 3.70-3.50 (m, 4H), 1.40-1.10 (t, J=7 Hz, 6H). $^{13}$C NMR (500 MHz in CDCl$_3$) δ: 138.80, 137.43, 136.59, 126.84, 125.93, 113.77, 101.00, 60.65, 15.10.

Synthesis of 4,6-O-(4-vinylbenzyl)-α-D-glucopyranosyl-(1→1) -α-D-glucopyranoside (2)

To a flame dried round bottom flask was dissolved 1 (0.500 g, 2.42 mmol, 1.00 eq) and trehalose (4.15 g, 12.1 mmol, 5.00 eq) in 150 mL DMF, and the resulting mixture was cooled to 0° C. Next, p-toluene sulfonic acid (92 mg, 0.20 mmol, 0.12 eq) was added and the solution was warmed to 25° C. and stirred for 3 h. Solvent was removed from the resulting crude reaction product in vacuo to give a white solid that was further purified by HPLC (40:60 to 10:90 water:methanol linear gradient over 30 minutes at 10 mL/min). After removal of solvents the resulting product 2 (456 mg, 0.99 mmol, 41% yield) was obtained as a white solid. $^1$H NMR (600 MHz, D$_6$DMSO) δ: 7.51 (d, 2H, 8.4 Hz), 7.46 (d, 2H, 8.4 Hz), 6.78 (dd, 1H, 10.8, 17.4 Hz), 5.89 (d, 1H, 17.4 Hz), 5.59 (s, 1H), 5.32, (d, 1H, 11.4 Hz), 5.26 (d, 1H, 4.8 Hz), 5.03-5.02 (m, 2H), 4.99 (d, 1H, 3.6 Hz), 4.92 (d, 1H, 3.6 Hz), 4.87-4.85 (m, 2H), 4.45 (dd, 1H, 6, 6 Hz), 4.14 (dd, 1H, 4.8, 9.6 Hz), 4.04 (ddd, 1H, 4.8, 9.6, 10.2 Hz), 3.80 (ddd, 1H, 4.8, 5.4, 9.3 Hz), 3.77 (ddd, 1H, 2.1, 4.5, 9.9 Hz), 3.69 (dd, 1H, 10.2, 10.2 Hz), 3.64-3.60 (m, 2H), 3.53 (ddd, 1H, 5.4, 5.7, 11.7 Hz), 3.45-3.40 (m, 2H), 3.32 (ddd, 1H, 3.8, 5.6, 9.4 Hz), 3.20 (ddd, 1H, 4.8, 5.4, 9.3 Hz). $^{13}$C NMR (500 MHz D$_6$DMSO) δ: 138.4, 138.3, 137.2, 127.6, 126.7, 115.8, 101.6, 101.5, 95.3, 94.8, 82.4, 73.6, 73.1, 72.4, 70.9, 70.5, 69.2, 63.3, 61.6. MS (ESI-MS) calc. for $C_{21}H_{28}O_{11}Na^+$: 479.15. observed: 479.15, IR: ν=3356, 2921, 1629, 1455, 1376, 1148, 1073, 976, 833, 800 cm$^{-1}$, UV/Vis (H$_2$O) λ=225, 259 nm. The NMR spectra are shown as FIG. 1.

Synthesis of Pyridyldisulfide Trithiocarbonate (3).

Figure 14:
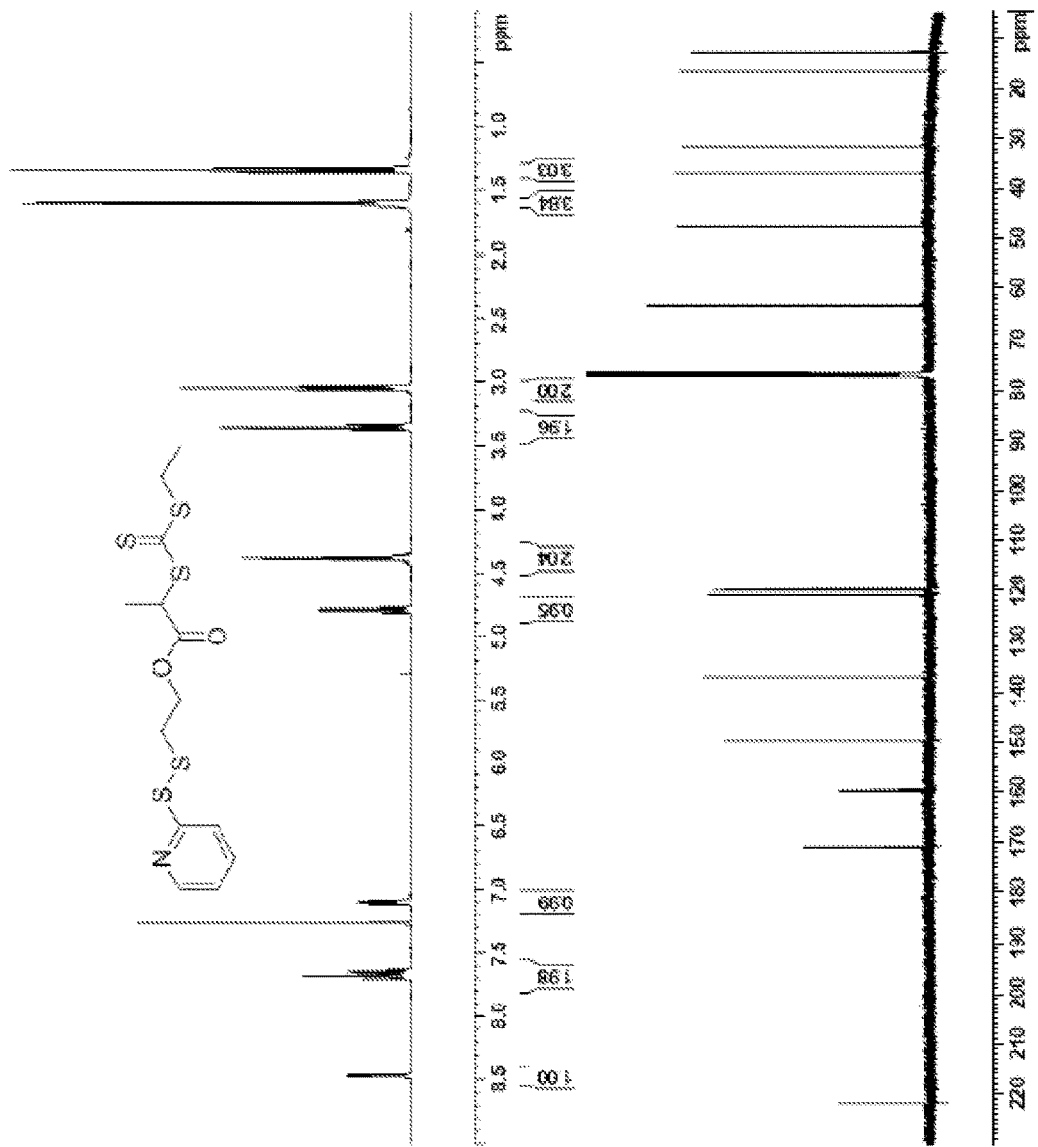
FIG. 14 is a graph showing $^1$H and $^{13}$C NMR spectra of pyridyldisulfide trithiocarbonate (3).

The synthesis was according to a literature procedure. Pyridyl disulfide alcohol (97.94 mg, 0.52 mmol) and trithiocarbonate acid (100 mg, 0.48 mmol) were dissolved in 9.60 mL of dry DCM. After the reaction was stirred at 0° C. for 20 min, 1-ethyl-3-(3-dimethylaminopropyl)carbodiimide (EDC, 273.41 mg, 1.56 mmol) and dimethylamino pyridine (DMAP, 11.62 mg, 0.10 mmol) were added. The reaction color changed from yellow to orange. The ice bath was removed after 5 h, and the reaction was stopped after 24 h. The solution was washed with 30 mL of H$_2$O three times and the organic layer was dried over MgSO$_4$. After silica gel column chromatography with Hex:EtOAc=1:1, 117 mg of product was collected (70% yield) as yellow oil. $^1$H NMR (500 MHz, in CDCl$_3$) δ: 8.48-8.47 (m, 1H), 7.70-7.63 (m, 2H), 7.11-7.09 (m, 1H), 4.81 (q, J=7 Hz, 1H), 4.43-4.35 (m, 2H), 3.39-3.34 (q, J=7 Hz, 2H), 3.09-3.03 (m, 2H), 1.61-1.59 (d, J=7 Hz, 3H), 1.37-1.34 (t, J=7 Hz, 3H).$^{13}$C NMR (500 MHz in CDCl$_3$) δ: 221.8, 170.9, 159.7, 149.8, 137.2, 121.0, 120.0, 63.5, 47.9, 37.3, 31.5, 16.7, 12.8. The NMR spectra are shown as FIG. 14.

RAFT Polymerization of Trehalose Monomer (Poly 1-4).

Figure 9:
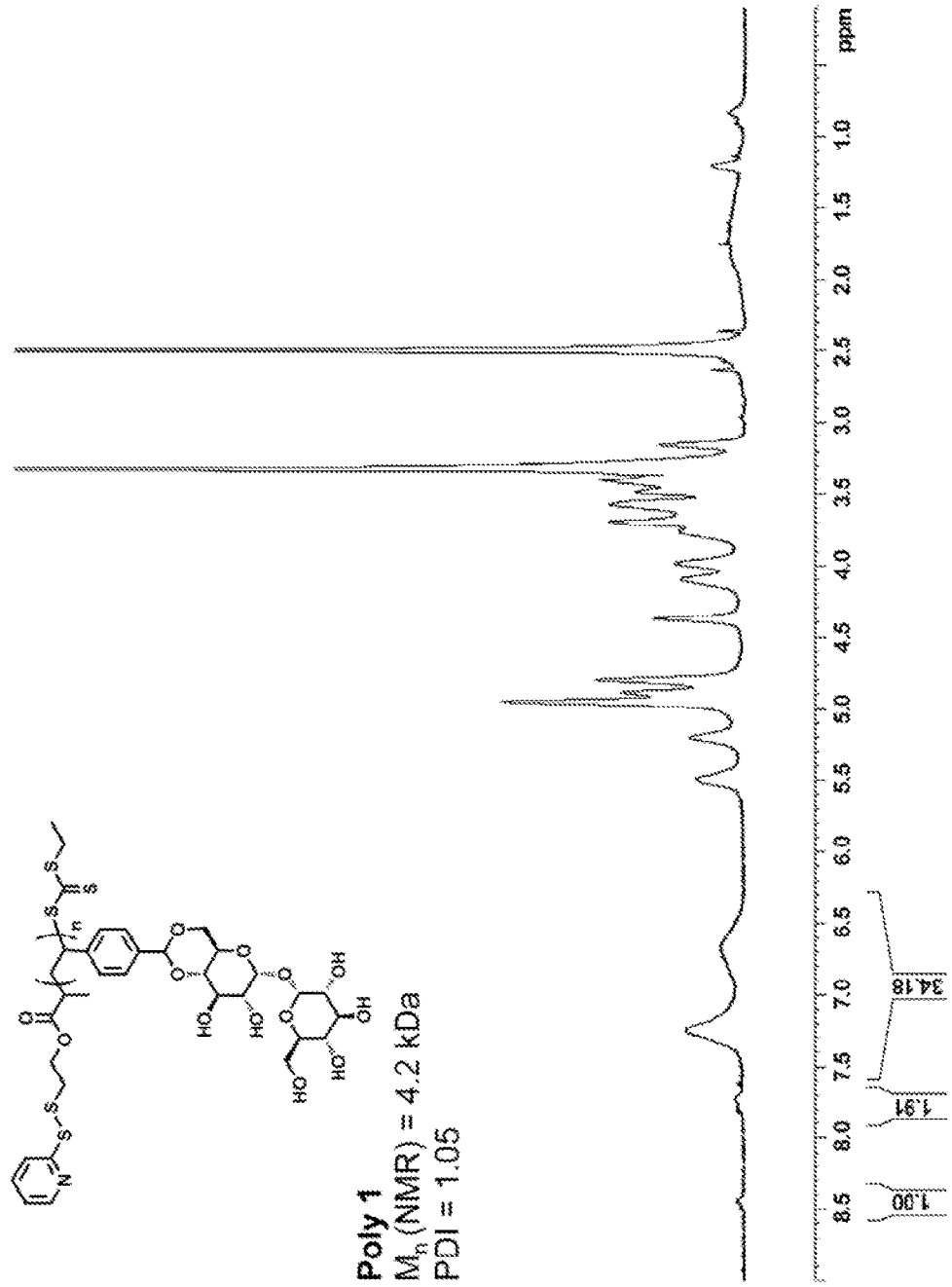
FIG. 9 is a set of graphs showing $^1$H NMR spectroscopy of trehalose polymers (Poly 1-4) (D6-DMSO).
Figure 9:
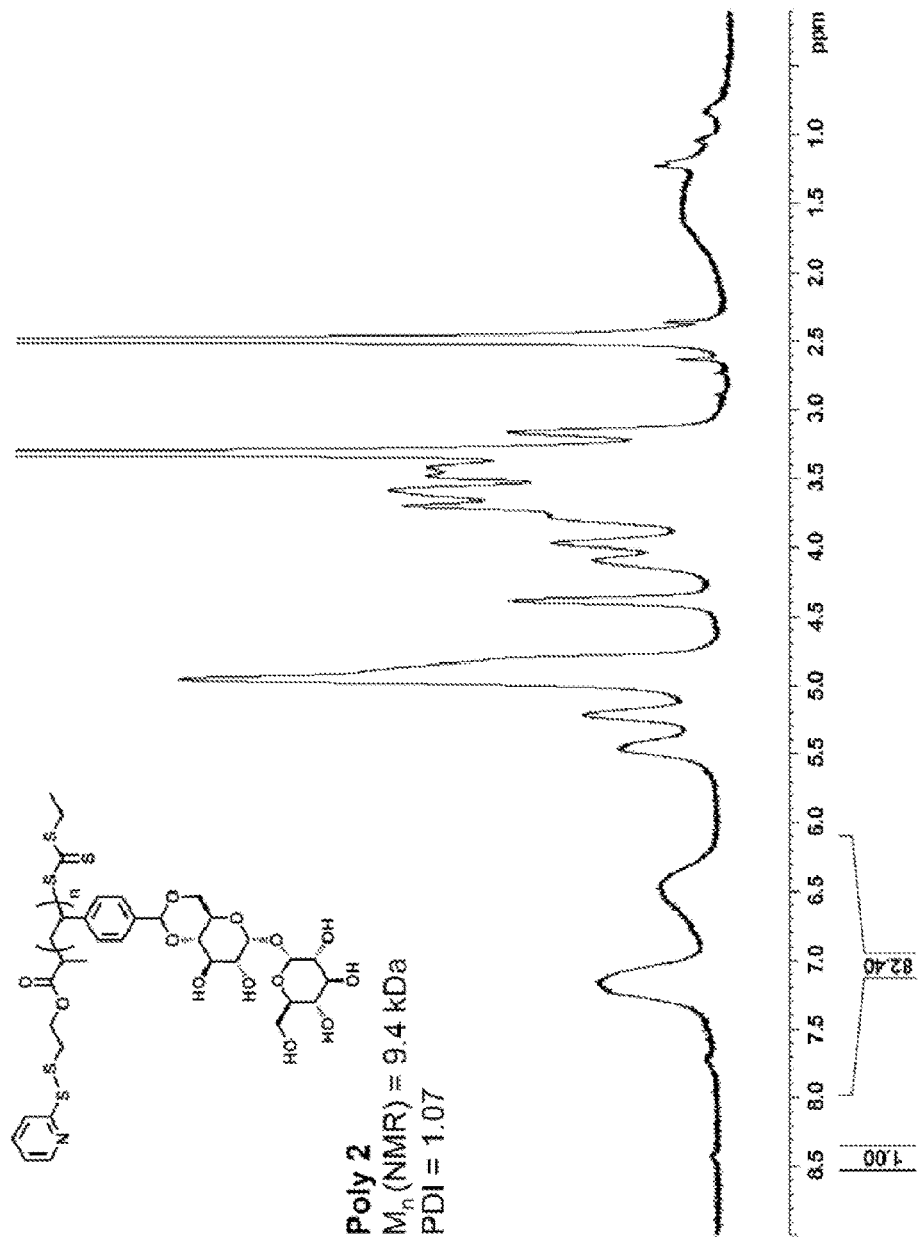
Figure 9:
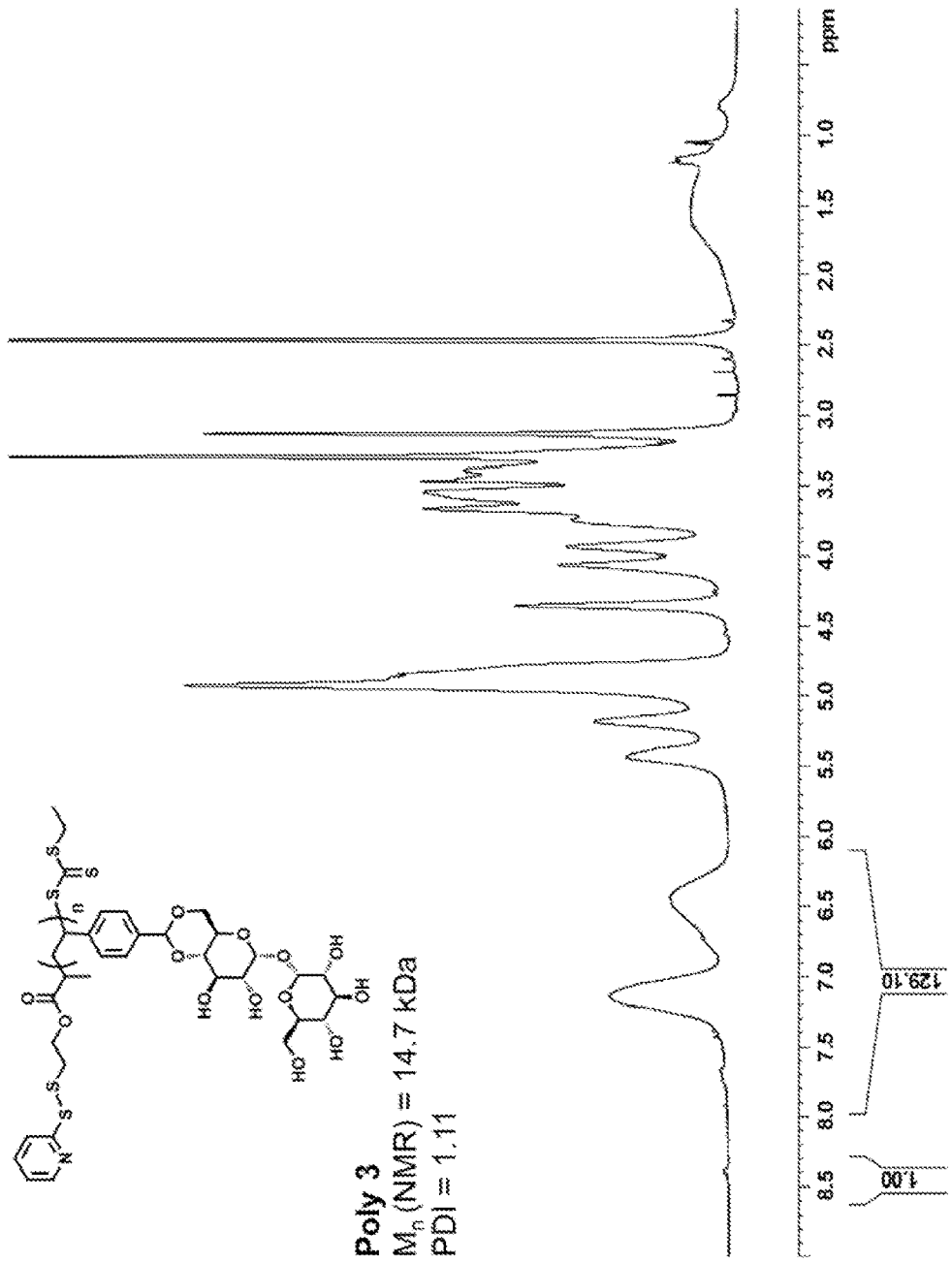
Figure 9:
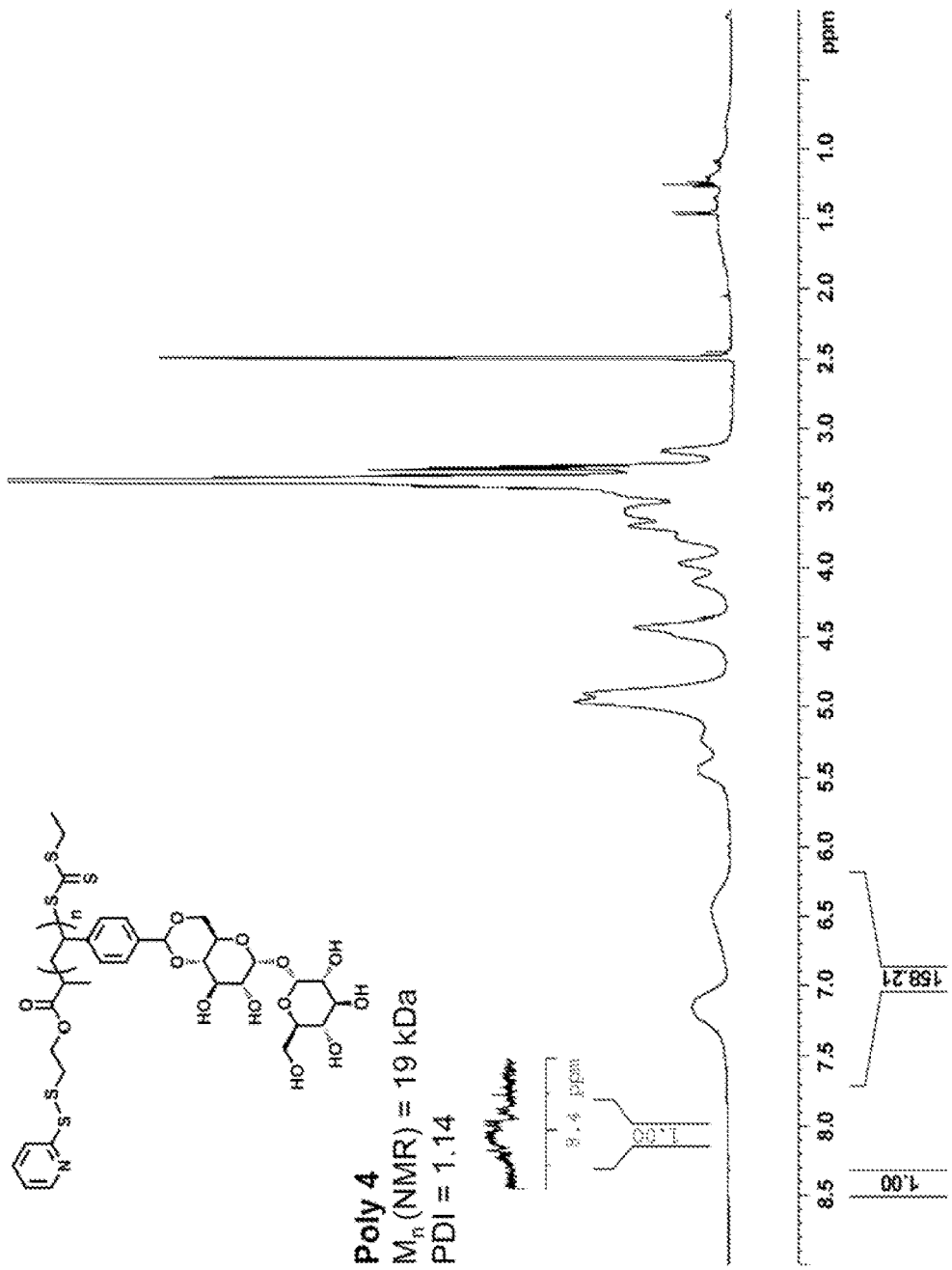

In a typical polymerization, 3 (18.34 mg, 5.22×10$^{-2}$ mmol), 2 (500 mg, 1.09 mmol) and AIBN (1.71 mg, 1.04×10$^{-2}$ mmol) were dissolved in 1.37 mL of dry DMF. Five freeze-pump-thaw cycles were repeated to remove oxygen, and the reaction was immersed in an 80° C. oil bath. After 6 h, the reaction was stopped by submerging the reaction flask into liquid nitrogen. The polymer 4 was purified by dialysis against H$_2$O made weakly basic with sodium bicarbonate (MWCO 2,000 g/mol) followed by MeOH. UV/Vis (H$_2$O): λ$_{max}$=213 nm, IR: ν=3298, 2914, 1653, 1375, 1148, 1112, 1072, 1020, 976, 824 cm$^{-1}$. Poly 1: $^1$H NMR (500 MHz, D6DMSO) δ: 8.47 (1H), 7.91-7.62 (m, 2H), 7.61-6.25 (m, 34H), 5.51, 5.22, 4.95, 4.90, 4.81, 4.37, 4.12, 3.98, 3.60, 3.78, 3.71, 3.57, 3.49, 3.42, 3.17, 1.71, 1.23, 0.85 ppm. Mn (NMR) 4.2 kDa. Mn (GPC) 8.5 kDa. PDI (GPC) 1.05. Poly 2: $^1$H NMR (500 MHz, D6DMSO) δ: 8.43 (1H), 7.93-6.03 (m, 83H), 5.47, 5.23, 4.95, 4.39, 4.10, 3.96, 3.70, 3.59, 3.49, 3.42, 3.16, 1.50, 1.25, 0.85 ppm. Mn (NMR) 9.4 kDa. Mn (GPC) 15.6 kDa. PDI (GPC) 1.07. Poly 3: $^1$H NMR (500 MHz, D6DMSO) δ: 8.40 (1H), 7.97-6.11 (m, 129H), 5.44, 5.19, 4.93, 4.36, 4.07, 3.94, 3.75, 3.67, 3.55, 3.47, 3.39, 3.13, 1.54, 1.19, 1.04, 0.83 ppm. Mn (NMR) 14.7 kDa. Mn (GPC) 17.3 kDa. PDI (GPC) 1.11. Poly 4: $^1$H NMR (500 MHz, D6DMSO) δ: 8.42 (1H), 7.71-6.16 (m, 158H), 5.45, 5.23, 4.96, 4.91, 4.44, 4.10, 3.97, 3.70, 3.59, 3.17, 1.40, 1.19, 1.04, 0.83 ppm. Mn (NMR) 19.0 kDa. Mn (GPC) 28.9 kDa. PDI (GPC) 1.14. The NMR spectra are shown as FIG. 9.

Synthesis of 2-(2-(2-(pyridin-2-yldisulfanyl)ethoxy)ethoxy)ethanol (4)

Figure 15:
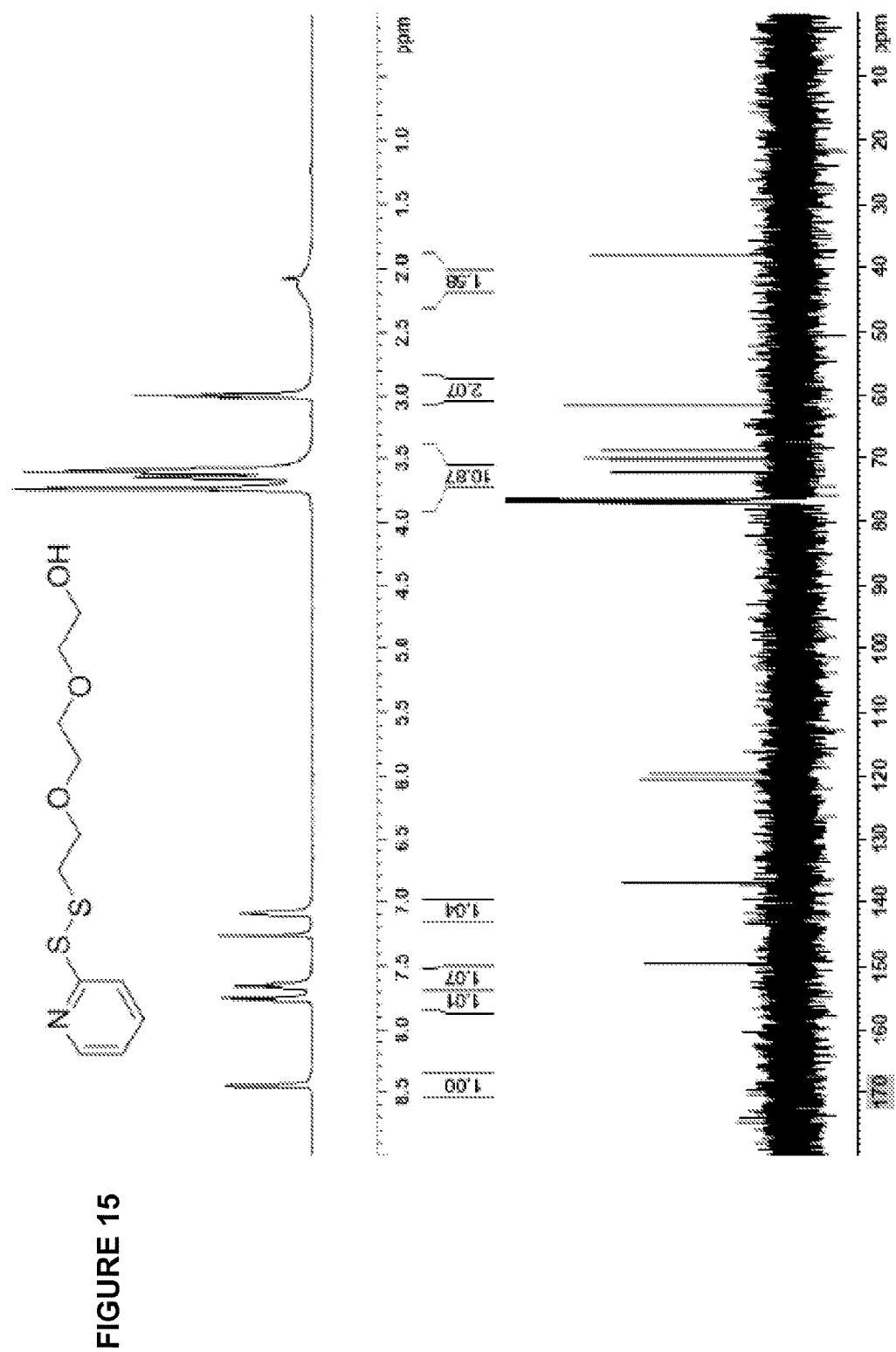
FIG. 15 is a graph showing $^1$H and $^{13}$C NMR spectra of 2-(2-(2-(pyridin-2-yldisulfanyl)ethoxy)ethoxy)ethanol (4).

In a flame dried round bottom flask Aldrithiol® (1.99 g, 9.03 mmol, 3 eq) was dissolved in methanol (24 mL) and acetic acid (1 mL). Next, 1-mercapto triethylene glycol (500 mg, 3.01 mmol, 1 eq) was added dropwise over 10 min. The resulting yellow reaction mixture was stirred for 140 min at 25° C. before removal of solvent in vacuo. The crude reaction product was dissolved in DCM, washed with water, dried with magnesium sulfate, and concentrated by rotary evaporation. The product was purified by column chromatography (100% EtOAc) to produce a yellow oil (613 mg, 2.22 mmol, 74% yield). $^1$H NMR (500 MHz, CDCl$_3$) δ: 8.46-8.45 (m, 1H), 7.77-7.64 (m, 2H), 7.10-7.08 (m, 1H), 3.75-3.58 (m, 10H), 3.01-2.98 (m, 2H), 2.14 (s, 1H). $^{13}$C NMR (500 MHz CDCl$_3$) δ: 149.4, 137.0, 120.6, 119.6, 72.4, 70.3, 70.3, 68.9, 61.7, 38.2. UV/Vis (MeOH) λ=256, IR: ν=3666, 2973, 2927, 2875, 1735, 1703, 1606, 1575, 1509, 1444, 1419, 1389, 1370, 1334, 1299, 1211, 1176, 1092, 1033, 1019, 1000, 918, 869, 846, 809, 720, 695 cm-1. The NMR spectra are shown as FIG. 15.

Synthesis of Thiol Reactive Chain Transfer Agent 5.

Figure 16:
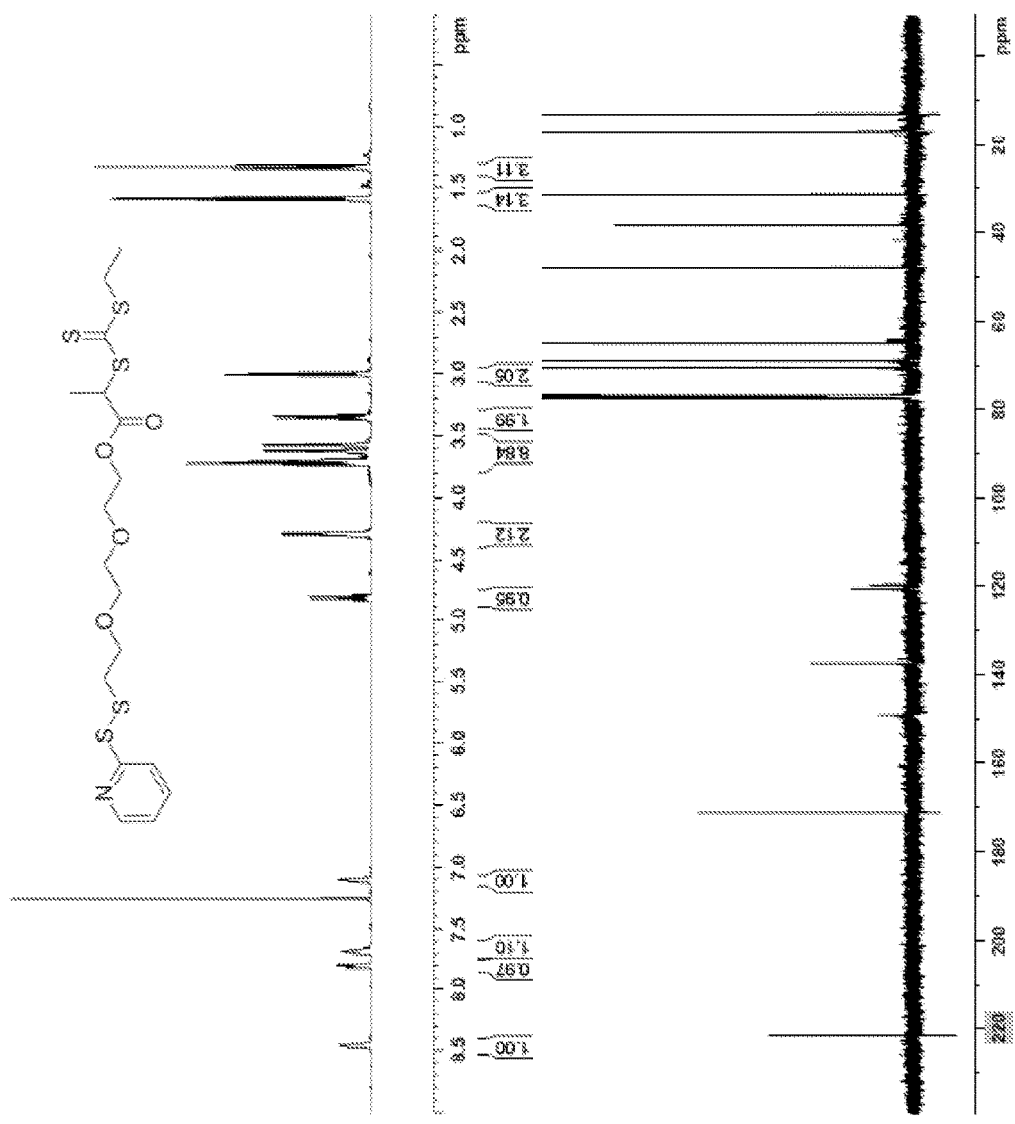
FIG. 16 is a graph showing $^1$H and $^{13}$C NMR spectra of thiol reactive Chain Transfer Agent (CTA 5).

In a flame dried round bottom flask 2-(2-(2-(pyridin-2-yldisulfanyl)ethoxy)ethoxy)ethanol (500 mg, 1.82 mmol, 1.1 eq) and 2-(ethyl sulfanylthiocarbonyl sulfanyl)-propionic acid (347 mg, 1.65 mmol, 1 eq) were dissolved in 16.5 mL of DCM made anhydrous by distillation. The reaction was stirred for 20 min at 0° C. before addition of EDC (759 mg, 3.96 mmol, 2.4 eq) and DMAP (40 mg, 0.33 mmol, 0.2 eq). After additional stirring at 0° C. for 5 hours the reaction was allowed to warm to room temperature and was stirred for an additional 24 h. The crude reaction product was washed 3 times with water and the organic layer was dried over MgSO$_4$. The solution was concentrated before purification by column chromatography (100% EtOAc) to isolate product 5 as a yellow oil (478 mg, 1.02 mmol, 62% yield). $^1$H NMR (500 MHz, CDCl$_3$) δ: 8.46-8.45 (m, 1H), 7.78-7.64 (m, 2H), 7.10-7.07 (m, 1H), 4.83 (q, J=7 Hz, 1H), 4.32-4.29 (m, 2H), 3.74-3.57 (m, 8H), 3.35 (q, J=8 Hz, 2H), 3.00 (t, J=6 Hz, 2H), 1.60 (d, J=7 Hz, 3H), 1.34 (t, J=7 Hz, 3H). $^{13}$C NMR (500 MHz, CDCl$_3$) δ: 221.8, 171.1, 160.4, 149.6, 137.1, 120.6, 119.6, 77.3, 77.0, 76.8, 70.6, 70.4, 69.5, 69.0, 69.0, 68.9, 65.0, 64.9, 64.4, 47.9, 39.9, 38.5, 31.5, 21.6, 16.9, 16.8, 13.0. UV/Vis (50% DMF$_{(aq)}$) λ 252 (ε=2.36), 297 (ε=12.76), IR: ν=3043, 2866, 1732, 1573, 1445, 1417, 1374, 1352, 1298, 1250, 1163, 1138, 1112, 1080, 1026, 1042, 985, 875, 812, 760, 717, 616 cm$^{-1}$. MS (ESI) calc for $C_{17}H_{25}NO_4S_5H$: 468.0465, Found: 468.0466. The NMR spectra are shown as FIG. 16.

Synthesis of ω-(ethyl sulfanylthiocarbonyl sulfanyl)-poly-4,6-O-(4-vinylbenzylidene) trehalose The synthesis is very similar to those of Poly 5-8 with end groups not removed. Different ratios of monomer to CTA were used to achieve different molecular weights. To a flame dried schlenk tube was added 2 (300 mg, 0.66 mmol, 300 eq), 5 (5.12 mg, 0.109 mmol, 5 eq) and AIBN (0.36 mg, 0.22 μmol, 1 eq) and anhydrous DMF (0.82 mL) before placing the mixture under argon protection. Oxygen was removed from the resulting solution by five freeze-pump-thaw cycles and the solution was heated to 80° C. for 6 hours. The polymerization was stopped by immersing the reaction vessel in liquid nitrogen and the polymer was purified by dialysis (MWCO 1 kDa, 1 mM NaHCO$_3$(aq) followed by MeOH, 3 days). Solvent was removed from the resulting polymer before standard characterization. $^1$H NMR (500 MHz, D$_6$DMSO) δ: 8.42 (m, 1H), 7.10-6.39 (m, 192H), 5.42, 5.21, 4.95, 4.86, 4.40, 4.10, 3.96, 3.70, 3.60, 3.34, 3.17, 3.16, 1.50 ppm. UV/Vis λ$_{max}$ 261 nm (ε=21.26), 311 nm (ε=9.25). IR: ν=3341, 2085, 1658, 1647, 1417, 1385, 1147, 1098, 1073, 1045, 977, 930, 826, 801, 722, 662 cm$^{-1}$. Mn (NMR) 22.4 kDa. PDI (GPC) 1.10.

Synthesis of ω-isobutyronitrile-poly-4,6-O-(4-vinyl-benzylidene) trehalose (6)

The ω-trithiocarbonate functionality was removed (Perrier, S., Takolpuckdee, P. & Mars, C. A. Reversible addition-fragmentation chain transfer polymerization: End group modification for functionalized polymers and chain transfer agent recovery. *Macromolecules* 38, 2033-2036 (2005)). In a typical procedure, to ω-(ethyl sulfanylthiocarbonyl sulfanyl)-poly-4,6-O-(4-vinylbenzylidene) trehalose (50 mg, 2.23 μmol, 1 eq) in a flame dried schlenk tube was added AIBN (7.33 mg, 44.6 μmol, 20 eq) and 0.5 mL DMF, and the reaction mixture was placed under argon protection. Oxygen was removed from the reaction vessel by five freeze-pump-thaw cycles before subsequent heating to 80° C. for 20 h. The resulting polymer 6 was purified by dialysis (MWCO 1 kDa, 50% MeOH$_{(aq)}$, 3 days) before lyophilization to give a white solid. UV/Vis $\lambda_{max}$ 261 nm ($\epsilon$=25.22). IR: ν=3330, 2923, 2112, 1652, 1376, 1149, 1101, 1072, 1047, 980, 928, 828, 801, 726 cm$^1$.

Synthesis of poly-4,6-O-(4-vinylbenzylidene) trehalose (Poly 5-8)

In a typical synthesis: To a flame dried Schlenk tube was added 2 (218.1 mg, 0.48 mmol), 5 (11 mg, 2.4×10-2 mmol) and AIBN (1.58 mg, 9.60 μmol, 1 eq) and anhydrous DMF (0.60 mL) before placing the mixture under argon protection. Oxygen was removed from the resulting solution by five freeze-pump-thaw cycles and the solution was heated to 80° C. for 94% monomer conversion. The polymerization was stopped by immersing the reaction vessel in liquid nitrogen and the polymer was purified by dialysis (MWCO 1 kDa, 1 mM NaHCO3(aq) followed by MeOH, 3 days). Solvent was removed from the resulting polymer before standard characterization. Poly 5: $^1$H NMR (500 MHz, D6DMSO) δ: 8.42 (1H), 7.80 (2H), 7.56-6.25 (m, 66H), 5.49, 5.20, 4.95, 4.79, 4.38, 4.11, 3.99, 3.78, 3.70, 3.58, 3.48, 3.43, 3.18, 2.99, 1.66, 1.25, 0.83 ppm. UV/Vis $\lambda_{max}$ 310 nm ($\epsilon$=18939 cm-1M-1). IR: ν=3354, 2929, 1638, 1419, 1375, 1211, 1147, 1098, 1072, 1046, 977, 929, 826, 800, 722, 662 cm-1. Mn (NMR) 8.0 kDa. Mn (GPC) 9.6 kDa. PDI (GPC) 1.10. Poly 6: $^1$H NMR (500 MHz, D6DMSO) δ: 8.47 (1H), 7.79 (2H), 7.40-6.16 (m, 87H), 5.46, 5.20, 4.95, 4.88, 4.38, 4.08, 3.96, 3.76, 3.69, 3.57, 3.47, 3.40, 3.15, 2.95, 1.48, 1.21, 1.08, 0.85 ppm. UV/Vis $\lambda_{max}$ 261 nm ($\epsilon$=68804 cm-1M-1). IR: ν=3371, 2930, 1655, 1376, 1212, 1385, 1148, 1098, 1073, 1046, 977, 930, 826, 800, 722, 662 cm-1. Mn (NMR) 15.4 kDa. Mn (GPC) 12.1 kDa. PDI (GPC) 1.13. Poly 7: $^1$H NMR (500 MHz, D6DMSO) δ: 8.25 (1H), 7.82 (2H), 7.41-6.11 (m, 210H), 5.45, 5.22, 4.97, 4.87, 4.42, 4.13, 3.98, 3.80, 3.72, 3.60, 3.49, 3.43, 3.18, 1.65, 1.25, 0.87 ppm. UV/Vis $\lambda_{max}$ 261 nm ($\epsilon$=38421 cm-1M-1). IR: ν=3353, 2919, 1618, 1376, 1212, 1148, 1098, 1073, 1046, 977, 929, 826, 800, 722, 662 cm-1. Mn (NMR) 24.5 kDa. Mn (GPC) 18.8 kDa. PDI (GPC) 1.20. Poly 8: $^1$H NMR (500 MHz, D6DMSO) δ: 8.42 (1H), 7.80 (2H), 7.47-6.02 (m, 429H), 5.45, 5.22, 4.97, 4.85, 4.39, 4.10, 3.98, 3.78, 3.71, 3.60, 3.48, 3.43, 3.17, 1.49, 1.39, 0.85, 1.27 ppm. UV/Vis $\lambda_{max}$ 261 nm ($\epsilon$=59405 cm-1M-1). IR: $=3368, 2928, 1615, 1373, 1212, 1385, 1147, 1098, 1073, 1046, 977, 930, 825, 800, 722, 662 cm-1. Mn (NMR) 49.5 kDa. Mn (GPC) 33.6 kDa. PDI (GPC) 1.47. The spectra of NMR are shown as FIG. 10.

Synthesis of Amine Reactive Chain Transfer Agent (8).

As shown in Scheme 4, to a flame dried round bottom flask was added tri(ethylene glycol) levulinate (1.07 g, 4.3 mmol, 1 eq), 2-(ethyl sulfanylthiocarbonyl sulfanyl)-propionic acid (1 g, 4.8 mmol, 1.1 eq), and DCM (35 mL). The reaction mixture was cooled to 0° C. before addition of DCC (1.38 g, 6.7 mmol, 1.55 eq) and DMAP (0.068 g, 0.6 mmol, 0.13 eq). The solution was stirred for 10 hours and allowed to warm to room temperature before removal of solvent in vacuo. The crude reaction product was purified by column chromatography (1:1 DCM:EtOAc) to obtain CTA 8 (1.00 g, 2.28 mmol, 53% yield). $^1$H NMR (400 MHz, CDCl$_3$) δ: 4.85 (q, 1H, J=7.4, 14.7 Hz), 4.31 (q, 2H, J=3.6, 6.1 Hz), 4.26-4.23 (m, 2H), 3.73-3.69 (m, 4H), 3.66-3.62 (m, 4H), 3.37 (q, 2H, J=7.5, 14.8 Hz), 2.76 (t, 2H, J=6.5 Hz), 2.62 (t, 2H, J=6.5 Hz), 2.20 (s, 3H), 1.62 (d, 3H, J=7.4 Hz), 1.36 (t, 3H, J=7.4 Hz) ppm.

Synthesis of ω-(ethyl sulfanylthiocarbonyl sulfanyl)-poly-4,6-O-(4-vinylbenzylidene) trehalose (9)

As shown in Scheme 5, to a flame dried schlenk tube was added 2 (180 mg, 0.39 mmol, 100 eq), 8 (8.69 mg, 0.02 mmol, 5 eq) and AIBN (0.65 mg, 4 μmol, 1 eq) and anhydrous D$_6$DMSO (1 mL) before placing the mixture under argon protection. Oxygen was removed from the resulting solution by five freeze-pump-thaw cycles and the solution was heated to 80° C. for 10 hours. The polymerization was stopped by immersing the reaction vessel in liquid nitrogen and the polymer was purified by dialysis (MWCO 1 kDa, 1 mM NaHCO$_3$(aq) followed by MeOH, 3 days). Solvent was removed from the resulting polymer before standard characterization. $^1$H NMR (500 MHz, D$_6$DMSO) δ: 7.16-6.46 (92H), 5.50, 5.24, 4.99, 4.88, 4.60 (1H), 4.43, 4.14, 4.00, 3.74, 3.63, 3.53, 3.45, 3.32, 3.21, 2.77, 2.74, 2.71, 2.16, 1.58, 1.28 ppm. Mn (NMR) 10.9 kDa. PDI (GPC) 1.42.

Lysozyme Conjugation

Thiopropionyl Hen Egg White Lysozyme (LyzSH).

Hen egg white lysozyme was reconstituted as received to a concentration of 10 mg/mL (50 mM PB, 1 mM EDTA, pH 7.5). Next, 10 μL of succinimidyl acetyl-thiopropionate (16 mg/mL, 65 mM in DMF) was added and the solution was cooled to 4° C. for 4 hours. The resulting modified protein was purified by centriprep ultrafiltration (MWCO 3 kDa, 50 mM PB, 1 mM EDTA, pH 7.5) to a final volume of 1 mL. The protein was then deprotected by treatment with 100 μL of a 0.5M hydroxyl amine solution (50 mM PB, 25 mM EDTA, pH 7.5). Purification of the final protein was performed by centriprep ultrafiltration (MWCO 3 kDa, 50 mM PB, 1 mM EDTA, pH 7.5) before quantification of free-thiols by Ellman's Assay (1:1.4 thiol:lysozyme).

Lysozyme-glycopolymer conjugate (Lyz-6). To a 1.5 mL Lo-Bind® centrifuge tube was added thiopropionyl hen egg white lysozyme (LyzSH) (70 μL, 10 mg/mL, DPBS, pH 8.0) and 6 (16 mg, 0.71 μmol, 15 eq) and the entire reaction was diluted to a final volume of 500 μL (DPBS, pH 8.0) before storage at 4° C. for 3 hours. The resulting mixture was purified by FPLC (50 mM PB, 150 mM NaCl, pH 7.4), fractions were concentrated by centriprep ultrafiltration (MWCO 3 kDa, DPBS, pH 7.4) and stored at 4° C. Samples were diluted 5 fold before the EnzChek® lysozyme activity assay was employed to measure fraction activity. In a typical assay 50 μL of diluted sample was incubated with 50 μL of *Micrococcus luteus* labeled with FITC (1 mg/mL) at 37° C. for 1 hour. Subsequently, fluorescence of lysed cell membrane and thus lysozyme activity was measured as FITC fluorescence (abs 480 nm/em 530 nm) and quantified relative to known standards.

Lysozyme-Glycopolymer Conjugate (Lyz-Poly 5-8).

To a 1.5 mL Lo-Bind® centrifuge tube was added thiopropionyl hen egg white lysozyme (LyzSH) (70 µL, 10 mg/mL, DPBS, pH 8.0) and Poly 5-8 (0.71 µmol, 15 eq) and the entire reaction was diluted to a final volume of 500 µL (DPBS, pH 8.0) before storage at 4° C. for 3 hours. The resulting mixture was purified by FPLC (50 mM PB, 150 mM NaCl, pH 7.4), fractions were concentrated by centriprep ultrafiltration (MWCO 3 kDa, DPBS, pH 7.4) and stored at 4° C. before further characterization by SDS-PAGE.

Wild-Type Lysozyme.

Wild-type lysozyme was prepared by reconstituting hen egg white lysozyme (0.1 mg/mL, 1 eq, DPBS, pH 7.4) as received without further purification. Samples were further diluted to 0.021 mg/mL (1 kU/mL) in 20 µL aliquots prior to application of lyophilization or thermal insults.

Wild-Type Lysozyme Stabilized by Glyco-Polymer.

Wild-type lysozyme samples mixed with glyco-polymer were prepared by adding trehalose polymer (Poly 5-8, 1 or 100 eq relative to lysozyme) to a solution of lysozyme (0.1 mg/mL, DPBS, pH 7.4) before storage at 4° C. Samples were further diluted to a lysozyme concentration of 0.021 mg/mL (1 kU/mL) in 20 µL aliquots prior to application of lyophilization or thermal insult.

Wild-Type Lysozyme Stabilized by Trehalose.

Wild-type lysozyme samples mixed with trehalose were prepared by adding trehalose (1 or 100 eq relative to the number of trehalose monomer units in Poly 5-8) to a solution of lysozyme (0.1 mg/mL, DPBS, pH 7.4) before storage at 4° C. Samples were further diluted to a lysozyme concentration of 0.021 mg/mL (1 kU/mL) in 20 µL aliquots prior to application of lyophilization or thermal insults.

Wild-Type Lysozyme Stabilized by Poly(Ethylene Glycol) (PEG).

Wild-type lysozyme samples mixed with PEG were prepared by adding PEG (2 kDa, 8.5 kDa, or 20 kDa; 1 or 100 eq relative to lysozyme) to a solution of lysozyme (0.1 mg/mL, DPBS, pH 7.4) before storage at 4° C. Samples were further diluted to a lysozyme concentration of 0.021 mg/mL (1 kU/mL) in 20 µL aliquots prior to application of lyophilization or thermal insults.

Lyophilization Stability Activity Assay.

Wild-type lysozyme was prepared by reconstituting hen egg white lysozyme (0.1 mg/mL, DPBS, pH 7.4) as received without further purification. Polymer controls were prepared by adding trehalose polymer (Mn (NMR) 18 kDa, 0.14 mg/mL or 14 mg/mL, 1 eq or 100 eq respectively) to a solution of lysozyme (0.1 mg/mL, DPBS, pH 7.4) before storage at 4° C. in 20 µL aliquots. Trehalose controls were prepared by adding trehalose (0.12 mg/mL or 12 mg/mL, 0.37 µmol or 0.37 mmol, 48 eq or 4800 eq respectively) to a solution of lysozyme (0.1 mg/mL, DPBS, pH 7.4, 1 eq) before storage at 4° C. in 20 µL aliquots. Lyz-6 conjugate (0.1 mg/mL DPBS pH 7.4) was used following FPLC purification and storage at 4° C. in 20 µL aliquots. Aliquots of each type were frozen by immersion in liquid nitrogen before solvent removal via lyophilization. The resulting white solids were reconstituted in 20 µL of Milli-Q water, and this procedure was repeated for a total of 10 lyophilization cycles. Next the EnzChek® lysozyme activity assay was employed as described previously to measure lysozyme activity of the stressed samples relative to identical aliquots that were not lyophilized. The results are provided for 6 repeats. Statistics were calculated utilizing the Students t test; % confidence as +/−=t*(standard deviation)/(number of trials)^(½) with p<1−% confidence/100.

Thermo-Stability (Heat Burden) Assay.

Wild-type lysozyme was prepared by reconstituting hen egg white lysozyme (0.1 mg/mL, DPBS, pH 7.4) as received and was stored without further purification at 4° C. in 20 µL aliquots. Lyz-6 conjugate (0.1 mg/mL, DPBS pH 7.4) was used following FPLC purification and stored at 4° C. in 20 µL aliquots. Aliquots of each type were stressed by heating to 90° C. for 3 hours before cooling to 4° C. Next, all samples were diluted 1:40 before use of the EnzChek® lysozyme activity assay as previously described. Activities of stressed samples were measured relative to identical aliquots that were not exposed to heat. The results are provided for 6 repeats. Statistics were calculated utilizing the Students t test; % confidence as +/−=t*(standard deviation)/(number of trials)^(½) with p<1−% confidence/100.

Example 2: Synthesis of an Additional Exemplary Monomer/Polymer

The monomer of the invention may be prepared with any polymerizable unit and linked to the trehalose moiety side chain in any fashion. As an illustrative example of another monomer that may be polymerized for use in the invention, methacryoyl monomer 12 was prepared (Scheme 7), and its use for polymer synthesis was demonstrated. (Scheme 8).

Materials and Methods.

All solvents were purchased from Fisher Scientific (Pittsburgh, Pa.) and trehalose was purchased from The Endowment for Medical Research, (Houston, Tex.). All other chemical reagents were purchased from Sigma-Aldrich. Dimethylformamide (DMF), methylene chloride (DCM), triethyl amine (TEA), and methacryloyl chloride were distilled prior to use. Water was removed from trehalose dihydrate by repeated azeotrope distillation with ethanol. Azobisisobutyrlnitrile (AIBN) was recrystallized 3 times from ethanol.

4,6-O-benzylidene-α-D-glucopyranosyl-(1→1)-4',6'-O-benzylidene-α-D-glucopyranoside (10)

To a flame dried round bottom flask was added anhydrous trehalose (5 g, 14.6 mmol, 1 eq), p-toluene sulphonic acid monohydrate (0.11 g, 0.6 mmol, 0.04 eq), and DMF (75 mL). Dimethoxy toluene (4.7 mL, 32.1 mmol, 2.2 eq) was added in two equal portions 20 minutes apart while maintaining the reaction temperature at 100° C. The mixture was stirred at 100° C. for an additional 40 minutes before removal of excess DMF in vacuo to produce a viscous liquid. The liquid was further purified first by recrystallization from xylenes followed by recrystallization from a mixture of ethanol:water (1:3) to yield long white needles as the final product (6.6 g, 13 mmol, 87% yield).

Scheme 7. Synthesis of dibenzylidene trehalose (10) followed by subsequent esterification with methacryloyl chloride to produce the protected trehalose monomer (11) and removal of benzylidene groups to obtain 2-methacryloyl trehalose (12).

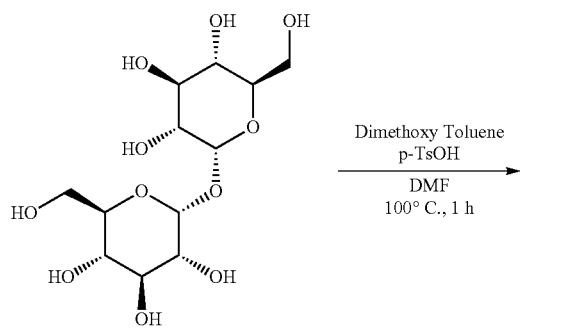

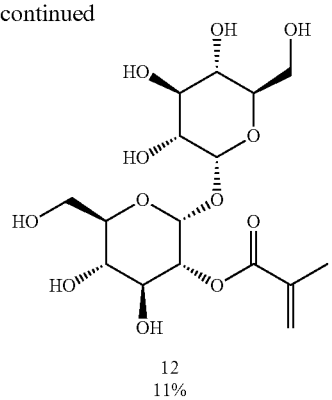

12
11%

Scheme 8. Polymerization of protected monomer (11) with thiol-reactive CTA 3 to produce glycopolymer (13) with an activated disulfide end-group.

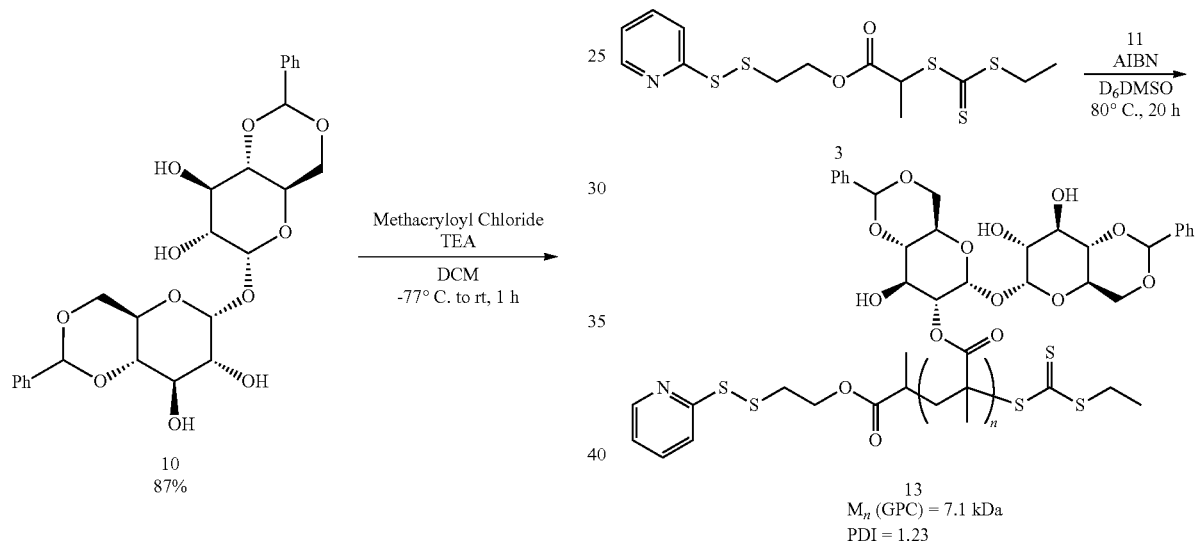

13
$M_n$ (GPC) = 7.1 kDa
PDI = 1.23

2-methacryl-4,6-O-benzylidene-α-D-glucopyranosyl-(1→1)-4',6'-O-benzylidene-α-D-glucopyranoside (11)

In a flame dried round bottom flask dibenzylidene trehalose (1 g, 1.93 mmol, 1 eq) was dissolved in DCM (20 mL), and TEA (0.59 g, 5.79 mmol, 3.0 eq) was added. The reaction mixture was placed under argon protection and cooled to −77° C. Methacryloyl chloride (0.30 g, 2.9 mmol, 1.5 eq) was added dropwise over 30 minutes and the reaction was subsequently stirred for 6 hours at −77° C. and 48 hours at room temperature. The crude reaction mixture was purified directly by column chromatography (50% ethyl acetate in hexanes) to obtain the title compound which was lyophilized from benzene to produce a white solid (0.34 g, 0.59 mmol, 31% yield).

2-methacryl-α-D-glucopyranosyl-(1→1)-α-D-glucopyranoside (12)

In a flame dried round bottom flask 11 (250 mg, 0.43 mmol) was dissolved in chloroform (10 mL) and the mixture

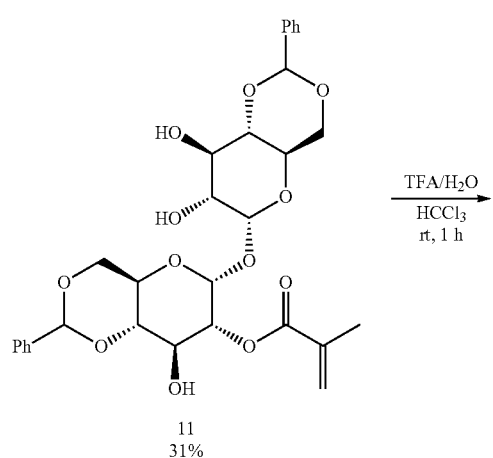

was placed under argon protection. Trifluoroacetic acid (1 mL) and water (1 mL) were added simultaneously over 5 min and the resulting reaction mixture was stirred for 1 h at room temperature before removal of solvents in vacuo. The resulting crude reaction product was purified by silica gel column chromatography (80% ethyl acetate, 10% butanol, 5% acetic acid, 5% water). Acetic acid was removed from the final product by azeotrope with toluene to obtain the title compound as a white solid (19 mg, 0.046 mmol, 11% yield).

Poly(2-methacryl-4,6-O-benzylidene-α-D-glucopyranosyl-(1→1)-4',6'-O-benzylidene-α-D-glucopyranoside) (13)

To a flame dried schlenk tube was added 2 (59 mg, 0.10 mmol, 100 eq), CTA 3 (1.91 mg, 0.01 mmol, 5 eq), and AIBN (0.17 mg, 0.001 mmol, 1 eq). The mixture was dissolved in $d_6$-Dimethyl sulfoxide, placed under argon and subjected to 6 freeze pump thaw cycles for removal of oxygen. The degassed solution was heated to 80° C. for 20 hours and the polymerization was stopped by immersion in liquid nitrogen. The resulting crude polymerization mixture was purified by dialysis against water followed by methanol (MWCO 3,000 Da) and lyophilization to obtain a light yellow powder. Mn (GPC) 7.1 kDa, PDI (GPC) 1.23.

Example 3: Synthesis of Polymers of Varying Molecular Mass

Figure 12:
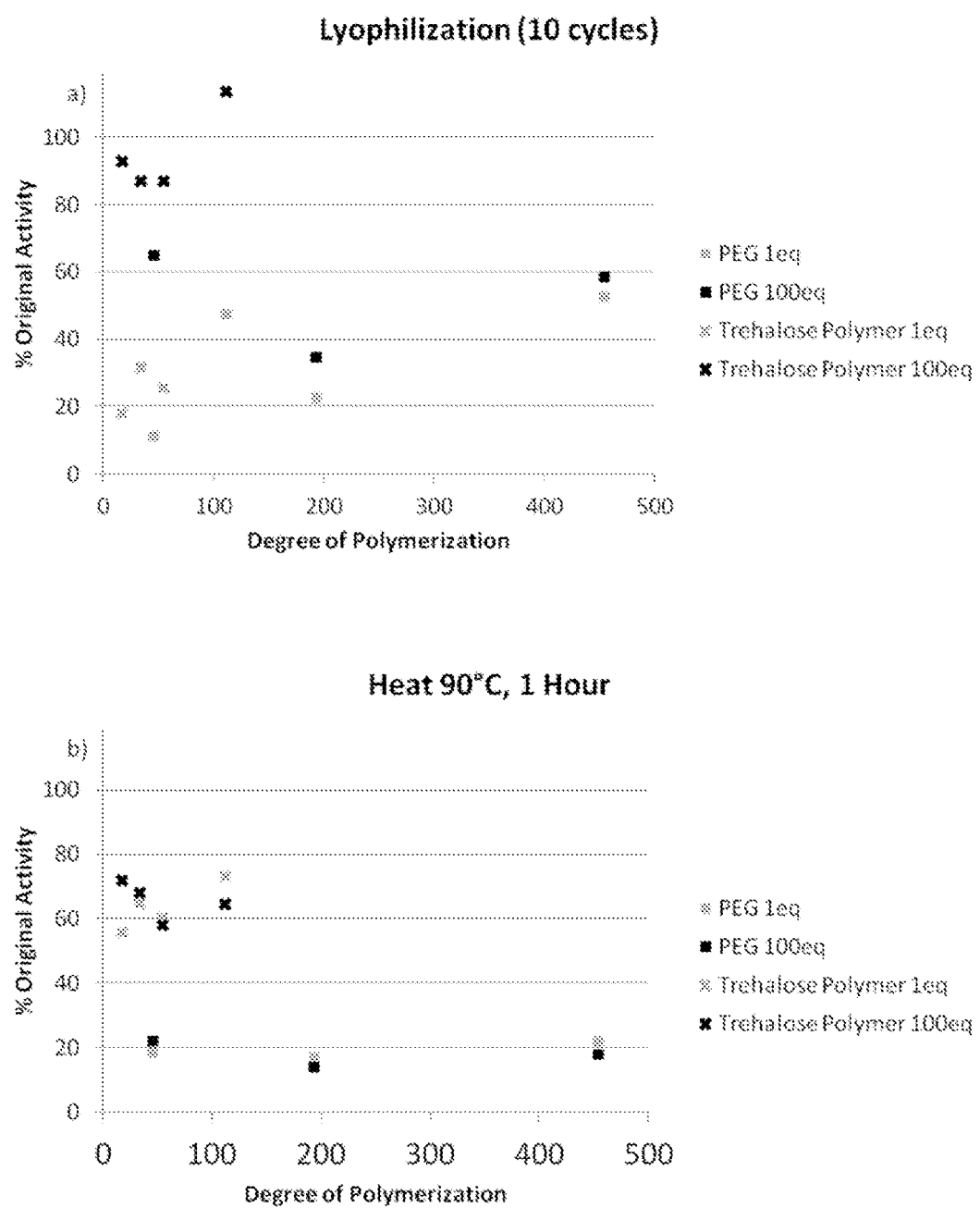
FIGS. 12a and b are a set of graphs showing activity retention of lysozyme stabilized by addition of PEG (1 or 100 eq) or trehalose polymer (1 or 100 eq) relative to degree of polymerization stressed by a) 10 cycles of lyophilization or b) a heat burden of 90° C. for 1 hour.

All of the trehalose polymers may be prepared with different molecular weights. As shown in Scheme 1, RAFT polymerization of 2 with 3 was performed at 80° C. The ratio used for polymerization was [CTA]:[monomer]:[AIBN]=1:29:0.2, with a concentration of 0.8 M monomer. After 6 h, the polymerization was stopped to obtain 77% conversion. The polymer was dialyzed against aqueous sodium bicarbonate with a MWCO 2,000 g/mol. The molecular weight of the polymer was analyzed by 1H NMR spectroscopy and was 9,600 Da by comparing the integration of the end-group pyridine peaks to the aromatic ring from styrene (see FIG. 12). The polydispersity indices (PDIs) by GPC was 1.07, demonstrating that a well-defined polymer was formed. The kinetic study of the trehalose polymer demonstrated that PDIs were well below 1.1 throughout the polymerization. The [CTA]:[monomer]:[AIBN] ratios were then altered to obtain other molecular weights ranging from 4,200 g/mol to 19,000 g/mol (Table 2, Poly 1-4) with narrow PDIs obtained in all cases.

As shown in Scheme 9, RAFT polymerization of 2 in the presence of 5 was shown to proceed for a range of molecular weights (Table 2, Poly 5-8) with slight deviation from narrow polydispersities obtained for highest molecular weight attempted (Poly 8). After purification by dialysis (1 kDa MWCO, H2O, 3 days) these thiol reactive glycopolymers were characterized by NMR spectroscopy to confirm end-group retention and complete removal of monomer (see FIG. 10).

Scheme 9. Polymerization of monomer 2 with thiol-reactive CTA 5 to produce polymers of Poly 5-8 with an activated disulfide end-group.

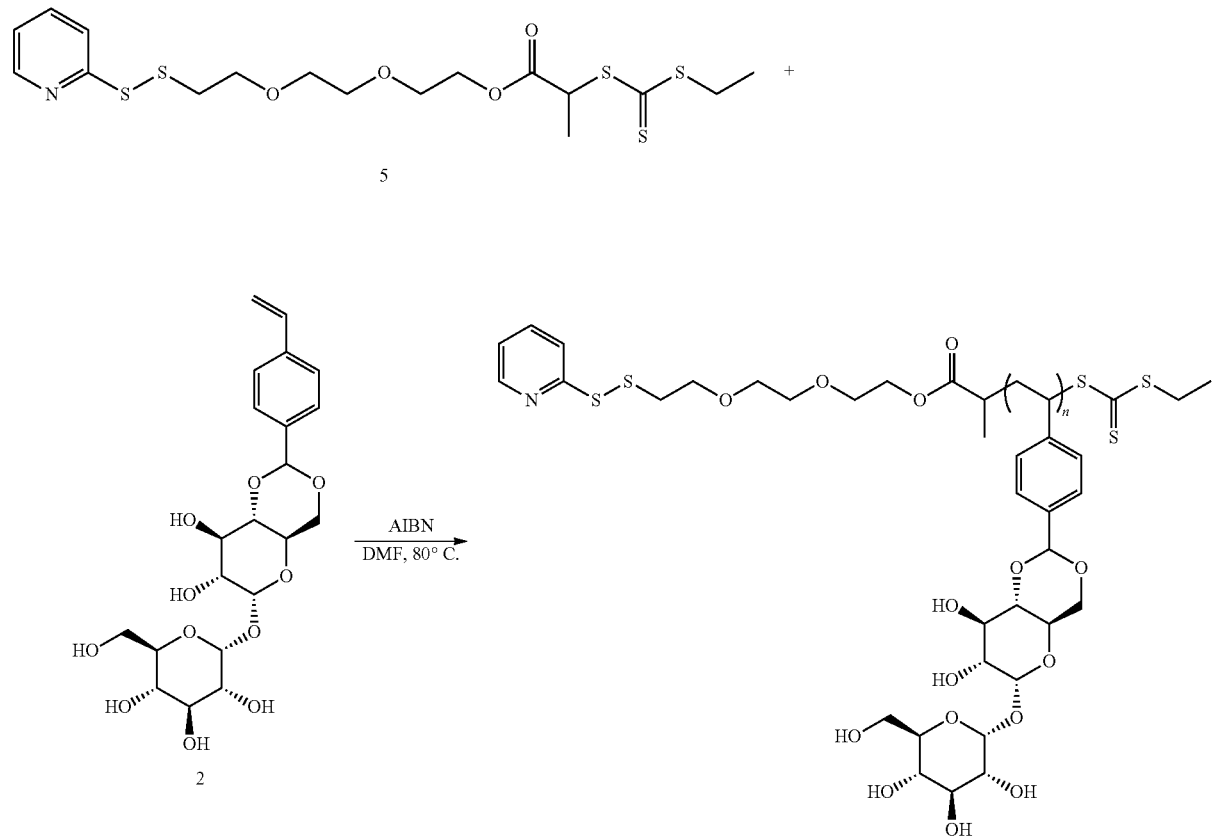

As shown below in Table 2, the molecular mass of the resulting polymer, as measured by $^1$H NMR, varies according to the concentration ratio of the three reactants. Thus, the reaction can be "tuned" to obtain a polymer having a desired molecular mass.

TABLE 2

Polymer Molecular Mass and Reactant Concentration Ratios

| Entry | CTA | CTA:M: AIBN | Target Mn | Conv (%) | Mn NMR | PDI |
|---|---|---|---|---|---|---|
| Poly 1 | 3 | 1:21:0.2 | 7,000 | 72 | 4,200 | 1.05 |
| Poly 2 | 3 | 1:29:0.2 | 9,600 | 77 | 9,400 | 1.07 |
| Poly 3 | 3 | 1:35:0.2 | 13,800 | 84 | 14,700 | 1.11 |
| Poly 4 | 3 | 1:50:0.2 | 20,000 | 85 | 19,000 | 1.14 |
| Poly 5 | 5 | 1:20:0.4 | 9,000 | 94 | 8,000 | 1.10 |
| Poly 6 | 5 | 1:60:0.2 | 11,400 | 40 | 15,400 | 1.13 |
| Poly 7 | 5 | 1:76:0.2 | 25,800 | 73 | 24,500 | 1.20 |
| Poly 8 | 5 | 1:120:0.4 | 44,800 | 81 | 49,500 | 1.47 |

Example 4: Lysozyme-Glycopolymer Conjugate Resistance to Environmental Stress

Figure 36:
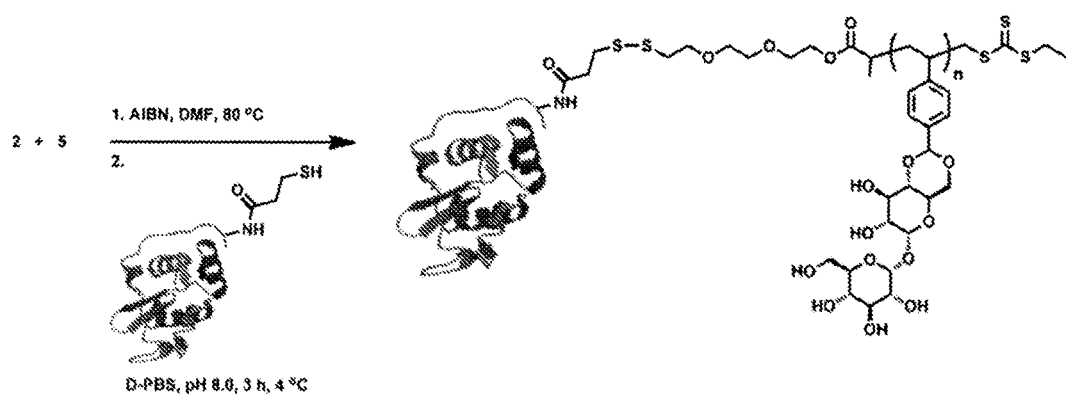
FIG. 36 shows Scheme 10. RAFT polymerization of 2 with CTA 5 to produce the thiol reactive glycopolymers Poly 5 through Poly 8. The glycopolymers were then conjugated to thiolated lysozyme.

As shown in Scheme 10 (FIG. 36), trehalose polymers were then conjugated to thiolated lysozyme. Thiols were added to hen egg white lysozyme by treatment with succinimidyl acetyl-thiopropionate (SATP) in a procedure known to covalently attach thioacetate functionality to proteins via amide bonds (Hernanson, 1996). After deprotection with hydroxyl amine and removal of excess SATP, free thiols were quantified on the thiolated lysozyme (LyzSH) by Ellman's assay resulting in a thiol: protein ratio of 1:1.4 (71% thiol). The LyzSH was then conjugated to various trehalose-based homopolymers (Poly 2, 5-8). After incubation with trehalose polymers, conjugates were seen by SDS-PAGE. The conjugation yield was lower for Poly 2 as compared to Poly 5-8. One possible explanation was that the TEG linker moves the thiol reactive end-group away from the bulky and hydrated trehalose side chain of the polymer improving access to the protein surface.

Figure 11:
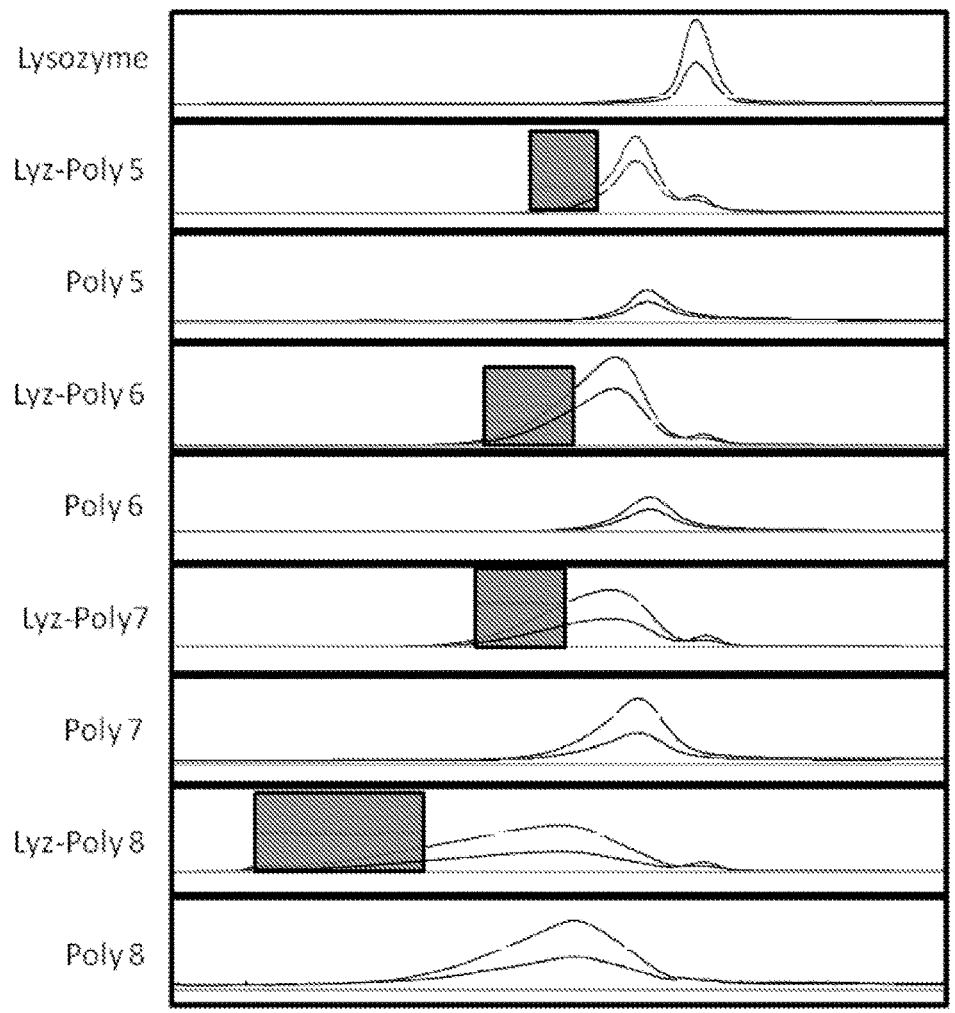
FIG. 11 is a set of graphs showing fast protein liquid chromatography (FPLC) trace of the conjugation of thiolated lysozyme to thiol-reactive glycopolymers (poly 5-8) monitored by conductivity, and UV absorbance at 254 nm and 280 nm with corresponding FPLC traces of native lysozymes and free polymer. Fractions concentrated for use in subsequent experiments are highlighted by the green boxes. These fractions were specifically chosen so as not to contain residual polymer of Lyz.

Lysozyme-glycopolymer conjugates (Lyz-Poly 5-8) were purified by fast protein liquid chromatography (FPLC) with subsequent runs of LyzSH and glycopolymer alone used to determine which fractions would be pure of starting materials (see FIG. 11). These fractions were collected and utilized in subsequent studies. Additionally, SDS-PAGE was used to confirm isolation of conjugate as demonstrated by the absence of lysozyme band under non-reducing conditions. Reappearance of the band under reducing conditions indicated that the polymer was conjugated to the lysozyme through a reducible disulfide bond. Activities of the purified Lyz-Poly conjugate fractions were confirmed by observing active lysis of the FITC labeled gram positive bacteria *Micrococcus luteus* in the EnzChek® lysozyme activity assay.

Figure 10:
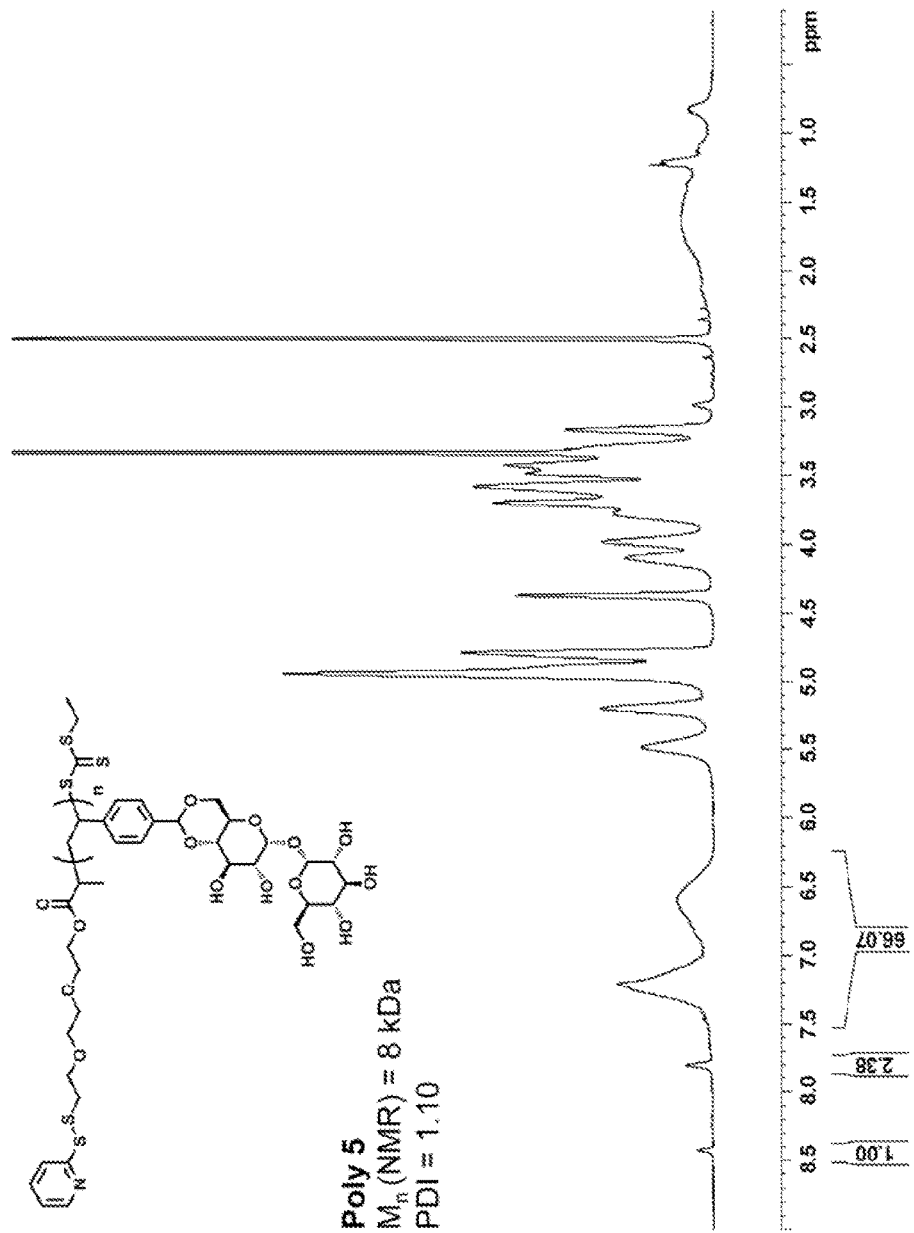
FIG. 10 is a set of graphs showing $^1$H NMR spectroscopy of trehalose-based polymers (Poly 5-8) (D6-DMSO).
Figure 10:
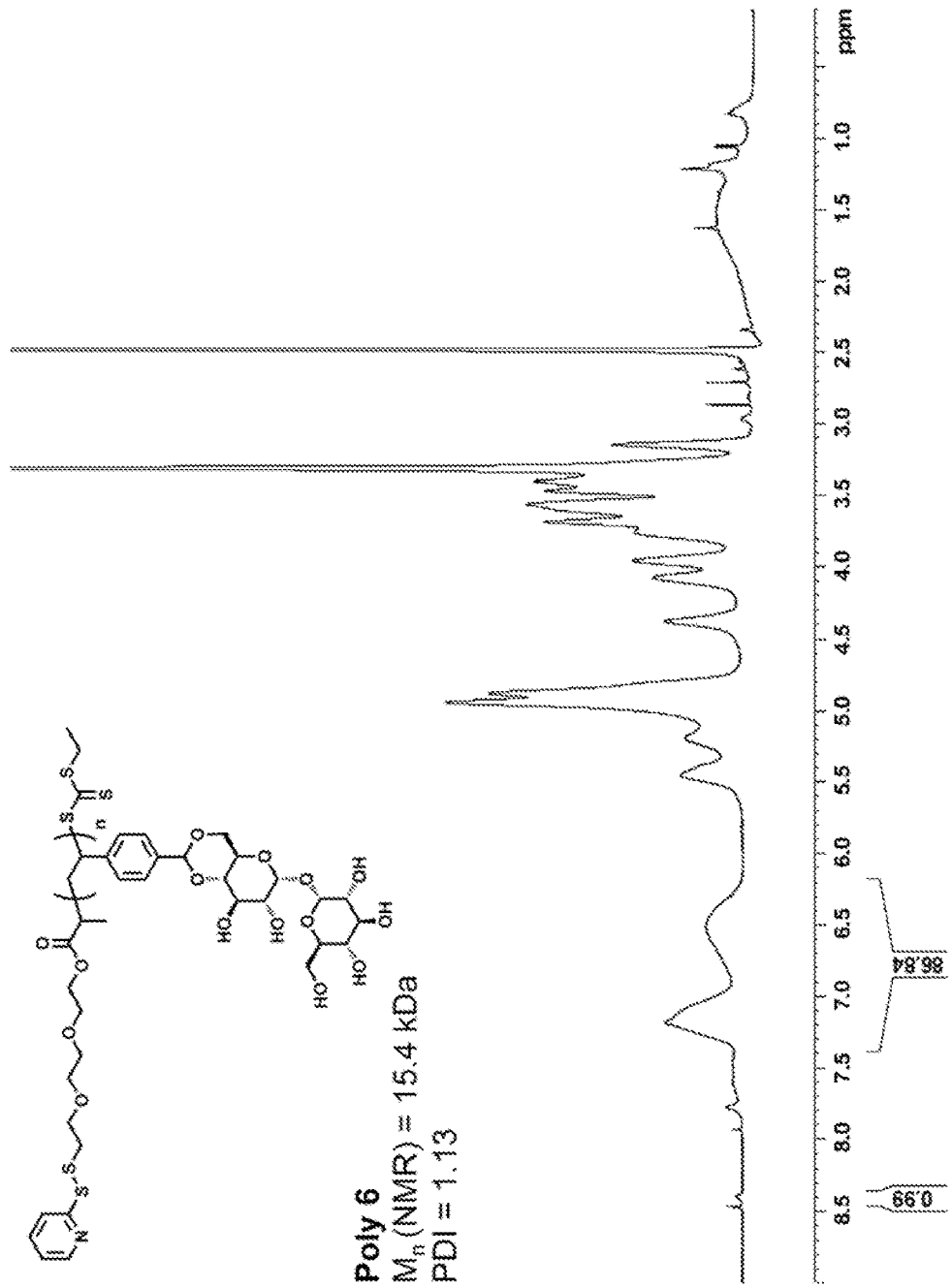
Figure 10:
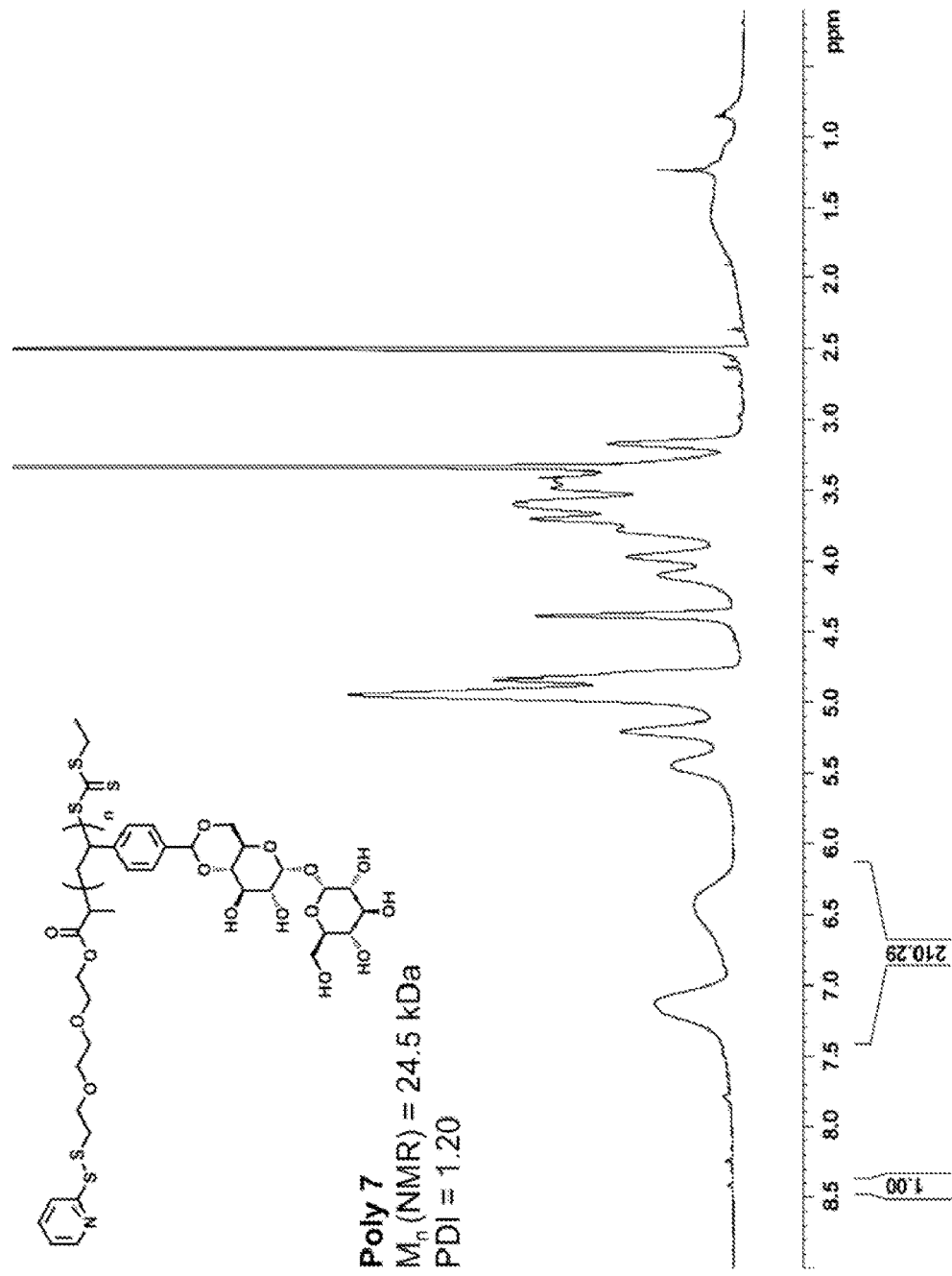
Figure 10:
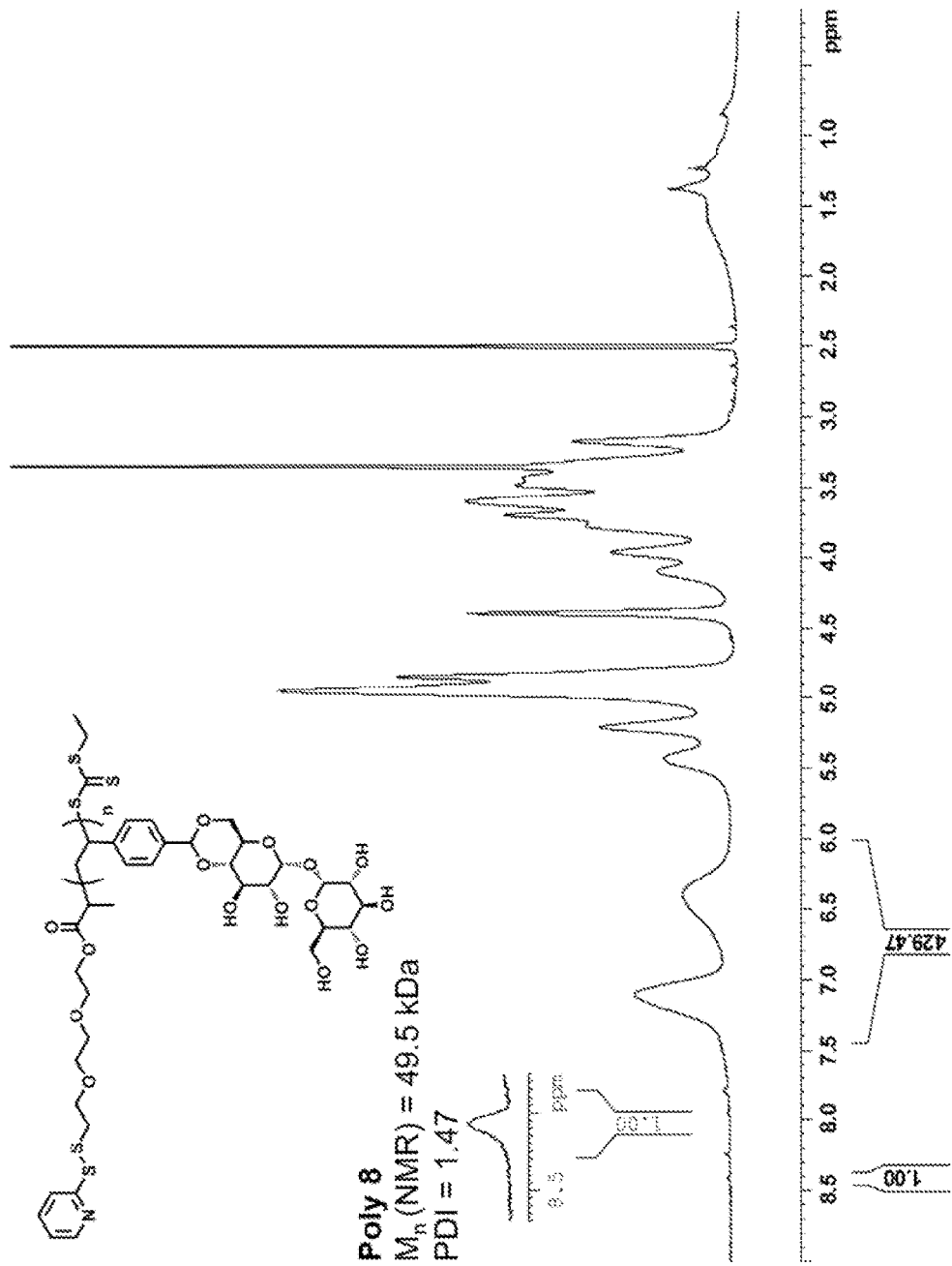

The ability of the polymers to stabilize lysozyme to lyophilization was first verified, and the results were compared to trehalose at the same concentrations. Poly 5-8 at 100 equivalents to protein were added (not conjugated) to wild-type Lyz containing no free thiols. Samples with trehalose added at equivalent concentrations to the trehalose in the various polymers were also tested. The samples were exposed to 10 lyophilization cycles, and the protein activity determined. Wild-type protein retained 16% activity after this treatment, while with a 100-fold excess of polymer, full retention (100%) of activity was observed (FIG. 10). The same effect was seen regardless of the molecular weight tested (8,000 to 49,500 Da). Trehalose at equivalent concentrations to that in the 100-fold polymers only stabilized the lysozyme between 18-31%. The results confirm that the polymers are able to protect the protein during lyophilization. Furthermore, the data show that the polymer is significantly more effective than trehalose alone at the same concentration relative to monomer units present in the polymer. This observation indicates that stabilization effects of trehalose are enhanced by using a polymer where the entropic barrier to having several carbohydrate moieties organized around the protein has already been included in the excipient. Trehalose itself has been proposed to stabilize proteins to desiccation via water replacement, water entrapment and vitrification. The mechanisms by which the trehalose-based homopolymers are stabilizing the protein are not yet understood, and investigative studies are underway. Regardless of the mechanism, the results suggest that trehalose polymers may be useful as a replacement for the disaccharide in formulations of unmodified biomolecules, particularly in instances where the additional materials properties imparted by the polymer would be advantageous.

Figure 7:
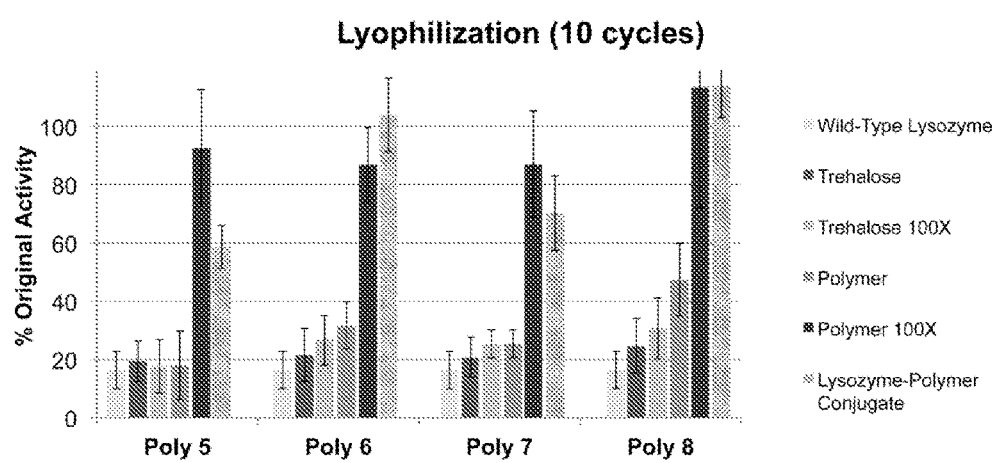
FIG. 7 is a diagram showing activity of lysozyme-glycopolymer conjugate, wild-type lysozyme with glycopolymer (1 or 100 eq relative to lysozyme), or wild-type lysozyme with trehalose (1 or 100 eq relative to polymer monomer units) as excipients exposed to 10 cycles of lyophilization. Data shown is repeated 6 times with $p<0.01$ for all polymer 100× and conjugate samples relative to wild-type.
Figure 8:
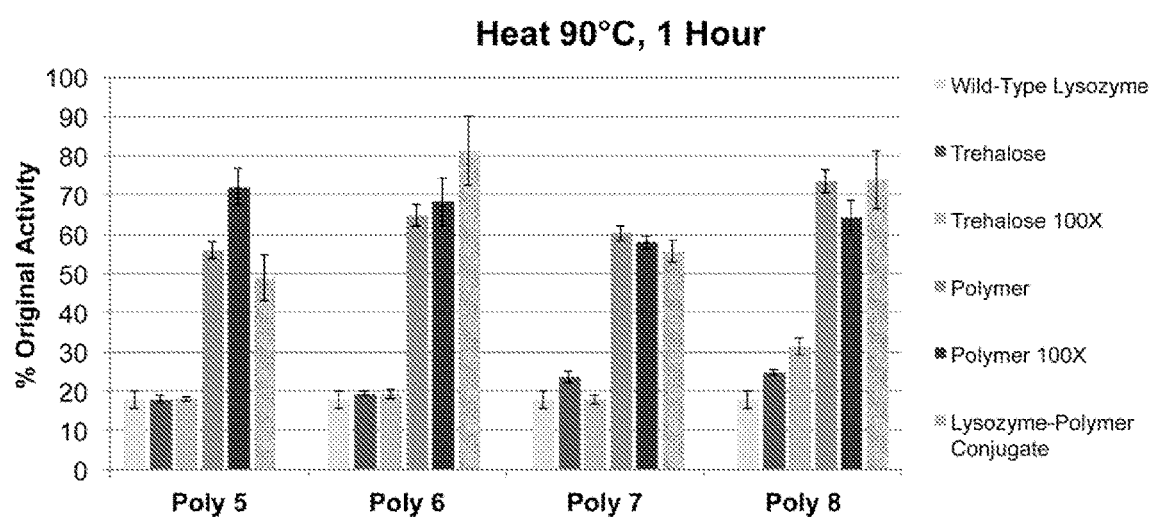
FIG. 8 is a diagram showing activity of lysozyme-glycopolymer conjugate, wild-type lysozyme with glycopolymer (1 or 100 eq relative to lysozyme), or wild-type lysozyme with trehalose (1 or 100 eq relative to polymer monomer units) as excipients exposed to a heat burden of 90° C. for 1 hour. Data shown is repeated 6 times with $p<0.001$ for all polymer and conjugate samples relative to wild-type.

To investigate the ability of the polymer to stabilize when conjugated to the protein, Lyz-Poly5-8 were exposed to the same 10 lyophilization cycles. In this case, the conjugates exhibited between 59 and 100% retention of original activity compared to 16% retention by wild-type lysozyme (FIG. 7). The smallest molecular weight Lyz-Poly5 had the lowest activity, while the largest polymer conjugate Lyz-Poly8 had full retention of activity. However, the activities of the medium sized polymers did not directly correlate to molecular weight. It is possible that this is due to differing numbers of polymer attached to the protein in the fractions analyzed; the number of polymers attached in the collected fractions could not be accurately estimated by SDS PAGE due to the low concentrations involved. Importantly though, the conjugates were all significantly more stable compared to samples containing similar concentration of unattached polymer added (1 eq to protein); addition of polymer resulted in only 18-47% retention of lysozyme activity. These results show that conjugating the polymer to the protein is advantageous with regard to environmental stability. Studies to determine the in vitro and in vivo stability of protein conjugates prepared from these polymers are underway in order to evaluate pharmacokinetic properties and potential use of the polymer in therapeutic conjugates. Trehalose is also known to stabilize biomolecules to increases in heat (Kaushik and Bhat, 2003; Singer and Lindquist, 1998; Xie and Timasheff, 1997). Therefore, an identical array of lysozyme samples were also stressed by exposure to a heat burden of 90° C. for 1 hour (FIG. 8). Although trehalose was found to confer marginal stabilization at the highest concentration tested here (31% activity retention for 100 eq Poly8), the trehalose polymer effects superior protection to heat, both added and as a conjugate. Up to 81% retention of activity under these rigorous conditions was observed. In this particular study, the protective effect was not concentration dependant as adding 1 eq and 100 eq or conjugating the polymer gave similar retention of activity for all molecular weights tested. However, in other studies, which were longer in duration and at a different concentration of protein, concentration dependence was observed (data not shown). Overall, the results demonstrate that the glycopolymers stabilize lysozyme to high temperatures. Furthermore the data suggest that the polymers should be investigated further as an excipient and conjugate to mollify the rigorous storage requirements that are typical for proteins, particularly during transport where large fluctuations in temperature may be observed.

Example 5: Comparison Between Trehalose Glycopolymers and the Commonly Used Excipient Poly(Ethylene Glycol) (PEG)

Figure 13:
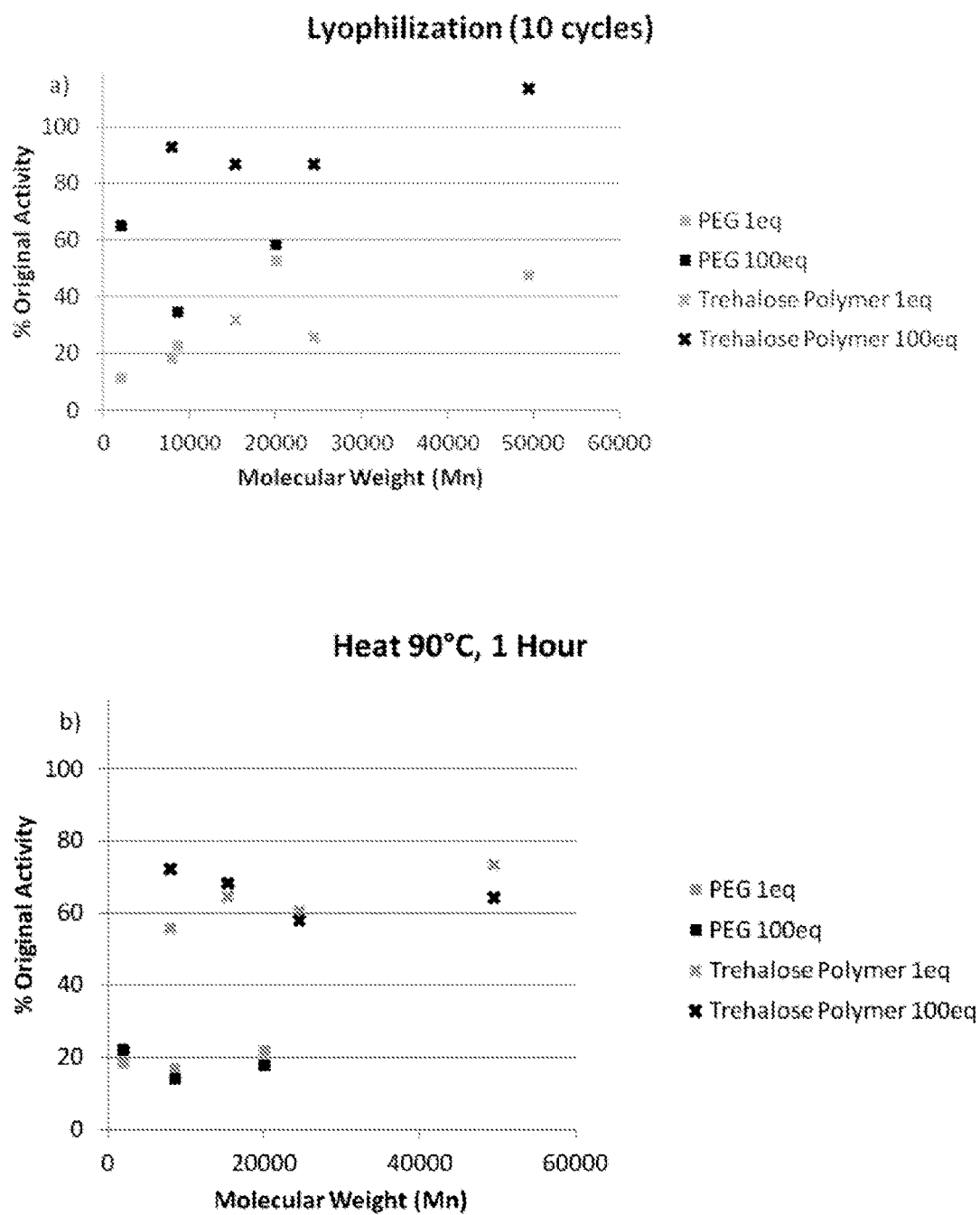
FIG. 13 is a set of graphs showing activity retention of lysozyme stabilized by addition of PEG (1 or 100 eq) or trehalose polymer (1 or 100 eq) relative to molecular weight (Mn) stressed by a) 10 cycles of lyophilization or b) a heat burden of 90° C. for 1 hour.

Additional initial studies were also conducted to compare the trehalose glycopolymers to the commonly used excipient poly(ethylene glycol) (PEG). As such, PEG (Mn=2-20 kDa) was combined with wild-type lysozyme at 1 or 100 eq and stressed by lyophilization or heat in an identical fashion as before. The lyoprotective effect of PEG (see FIGS. 12 and 13) was found to depend on degree of polymerization (DP) with the trehalose glycopolymer outperforming PEG for both 1 and 100 eq relative to protein. Although based on molecular weight, 1 eq of glycopolymer performed similarly to 1 eq of PEG and 100 eq of glycopolymer was a more effective lyoprotectant than PEG. Thermal stability of PEG relative to the glycopolymers was also investigated by exposing the relevant samples to a heat burden of 90° C. for 1 h as before. Although PEG mediates the thermal stress to a minimal extent, the trehalose glycopolymer outperforms PEG based on DP or Mn for all samples tested (see FIGS. 12 and 13). The data collectively indicates that trehalose side chain polymers are highly effective and superior to PEG alone as stabilizers of a representative protein, lysozyme, to lyophilization and heat stress.

Example 6: Trehalose-Based Polymers by Free-Radical Polymerization for Use as Excipients In addition to the monomer with styrenyl acetal as the polymerization handle, trehalose was modified with methacrylate acetal, methacrylate ether, and styrenyl ether moieties to result in three different monomers as examples. These monomers and the styrenyl acetal monomer were then separately polymerized using free radical polymerization with azobisisobutyronitrile (AIBN) as an initiator to synthesize each trehalose polymer. The homopolymers were tested and showed significant stabilization of activity in horseradish peroxidase under 70° C. for 30 min, glucose oxidase under 50° C. for 30 min, insulin for 1 h at 90° C. and 3-galactosidase after 4 cycles of lyophilization. Also, cytotoxicity studies with NIH 3T3, RAW 264.7 murine macrophages, human dermal fibroblasts, and human umbilical vein endothelial cells showed that all the polymers were non-cytotoxic to concentrations up to 1 mg/mL as tested.

Production of Glycopolymers P1

Figure 17:
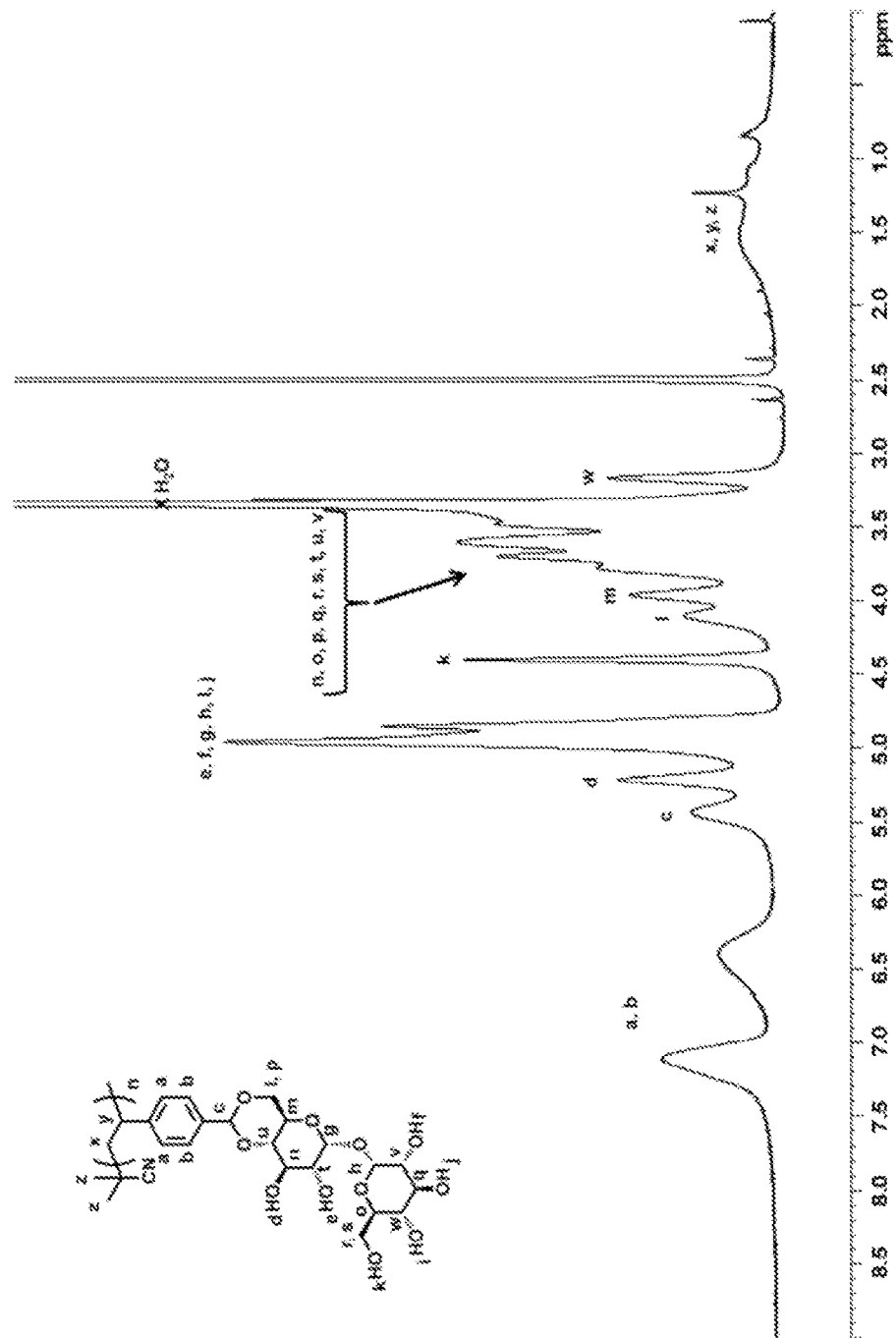
FIG. 17 is a graph showing $^1$H spectra of polymer P1 (in $D_6$DMSO).

The glycopolymer P1 was prepared with monomer 2 (Scheme 11). Azobisisobutyronitrile (AIBN) was used as an initiator at 80° C. After 17 h, the monomer conversion was 100%, and the polymer was purified by dialysis against $H_2O$. The resulting polymer, P1, had a number average molecular weight ($M_n$) of 34.3 kDa and PDI of 1.96 (FIG. 17).

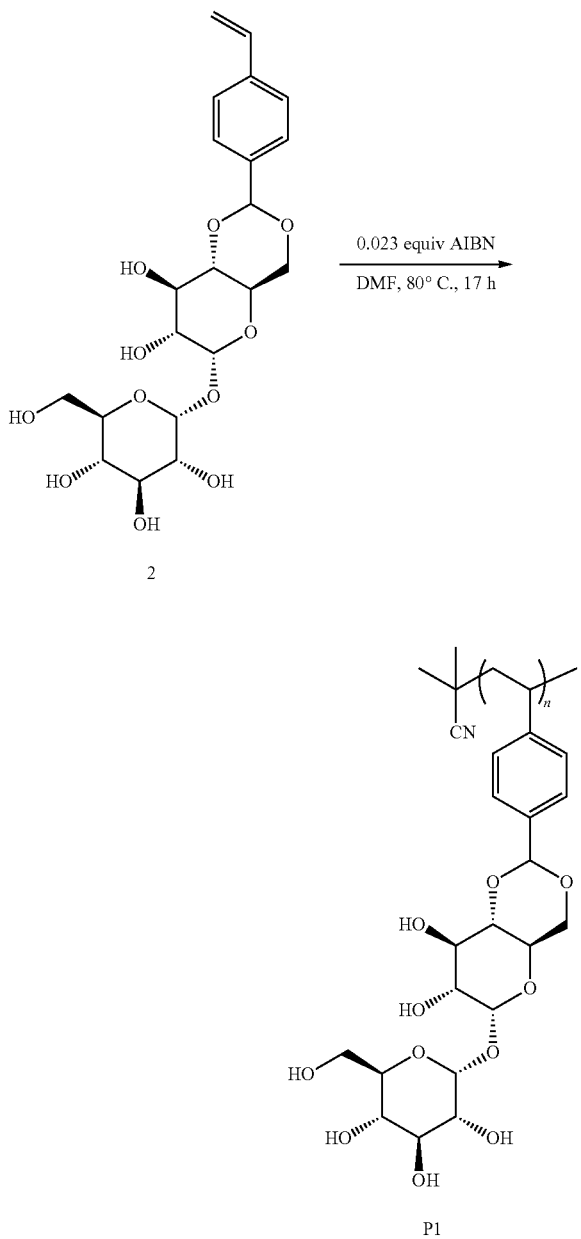

Scheme 11. Free Radical Polymerization of 2 Mediated by AIBN.

Production of Glycopolymers P2

Figure 18:
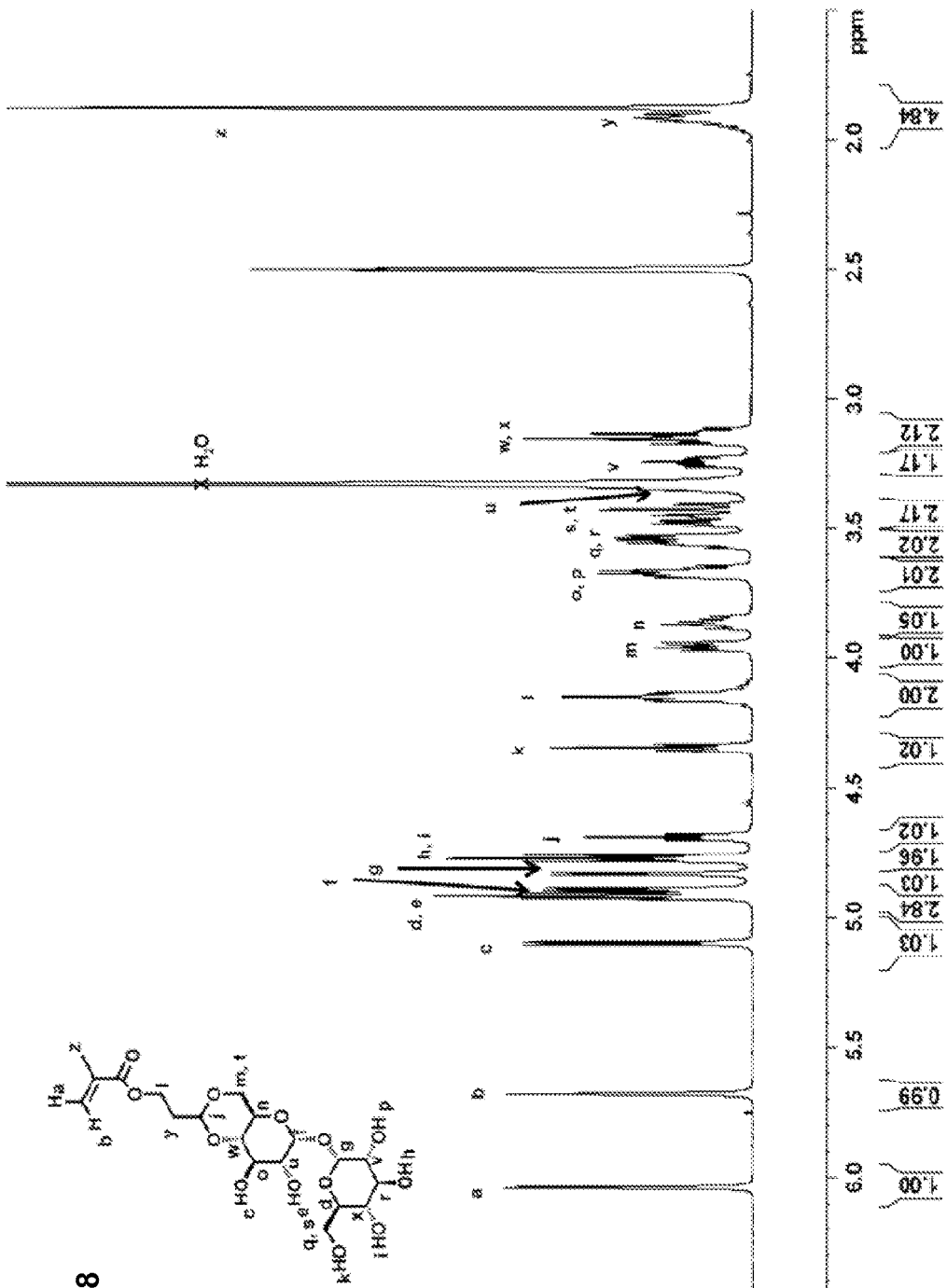
FIG. 18 is a graph showing $^1$H spectra of the monomer to form polymer P2 (in $D_6$DMSO).
Figure 19:
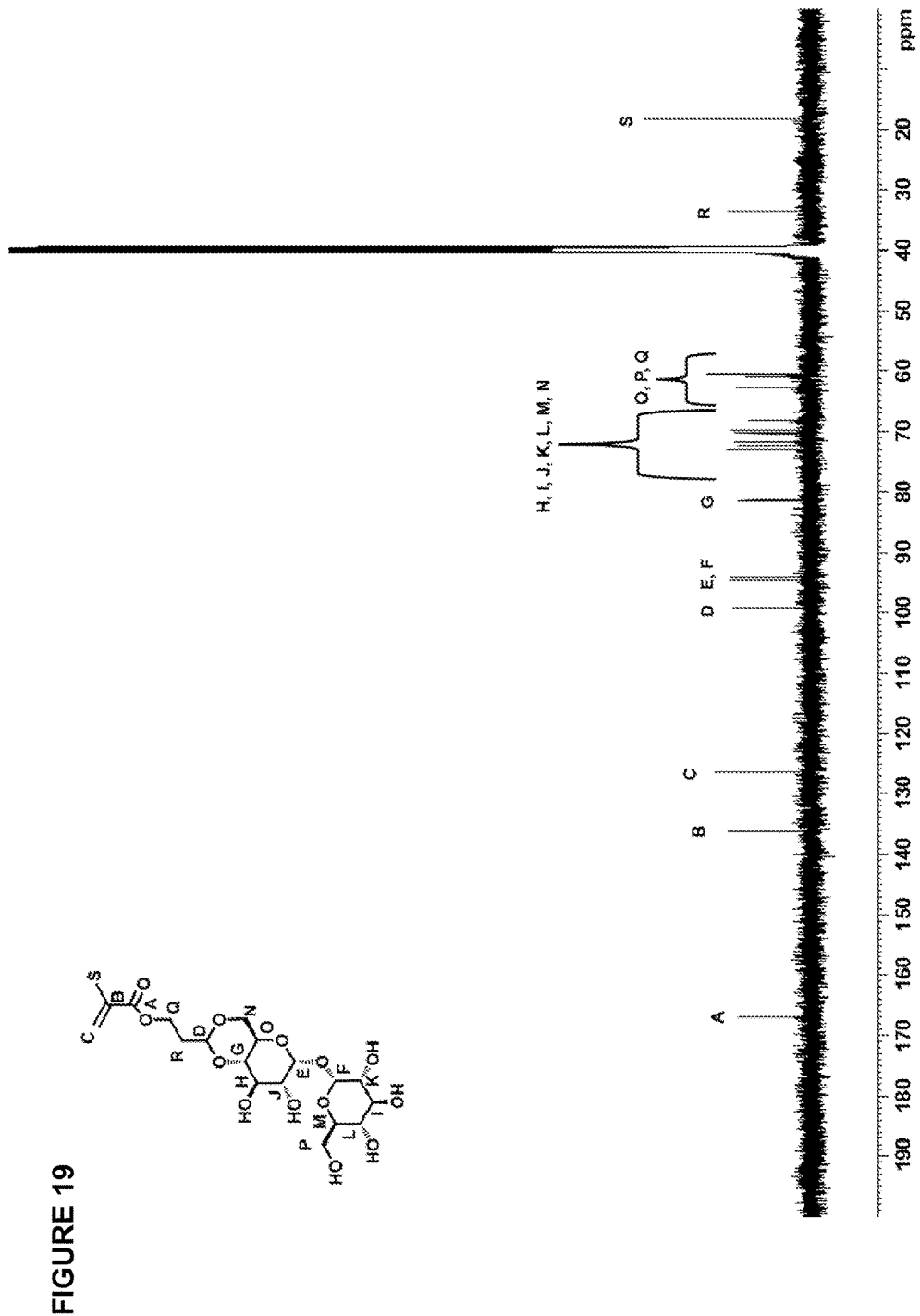
FIG. 19 is a graph showing $^{13}$C NMR spectra of the monomer to form polymer P2 (in $D_6$DMSO).
Figure 20:
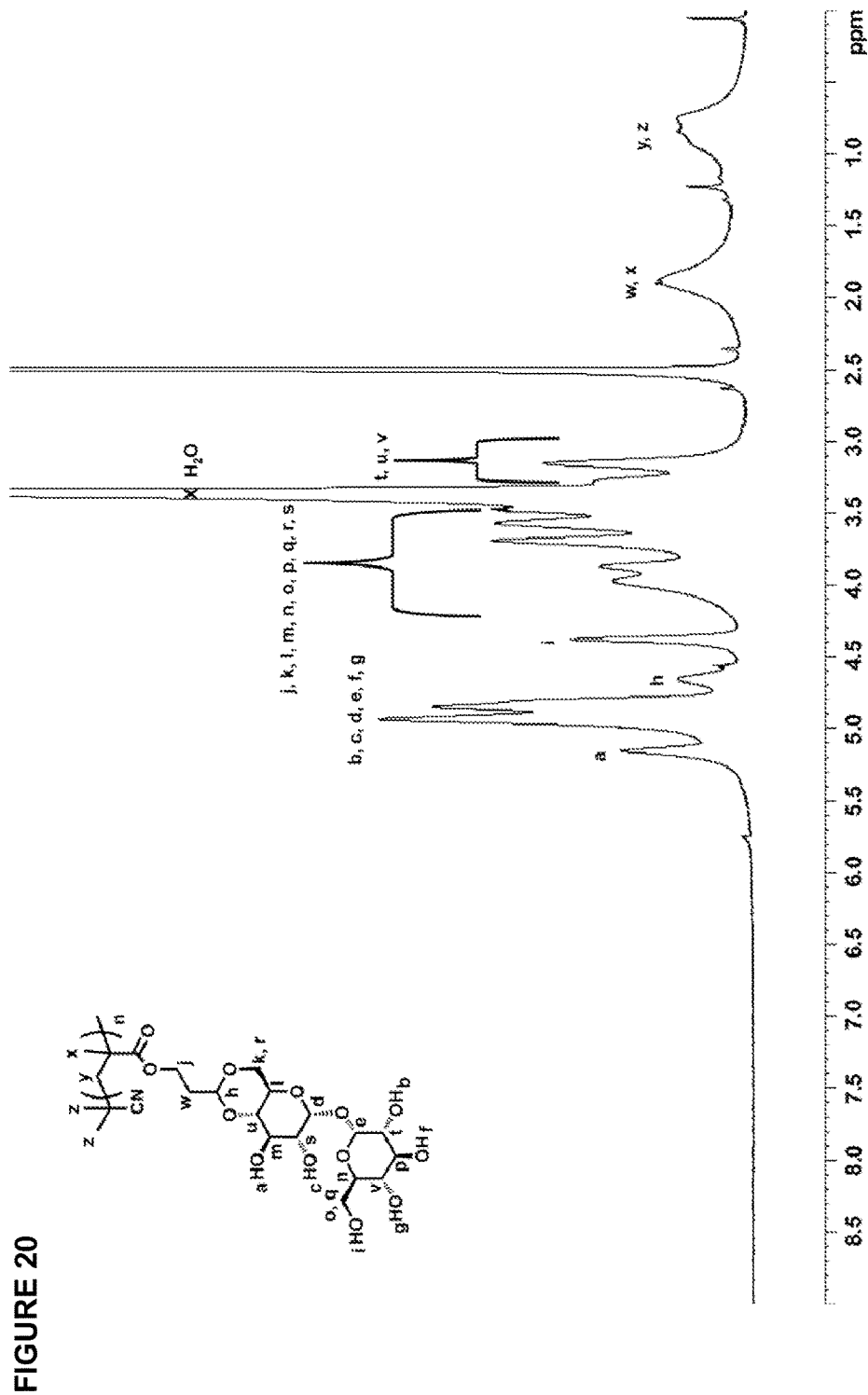
FIG. 20 is a graph showing $^1$H spectra of polymer P2 (in $D_6$DMSO).

The methacrylate acetal trehalose monomer 15 was synthesized using 3,3'-diethoxypropyl methacrylate (DEPMA, 14) as a starting material as shown in Scheme 12. Under slightly acidic conditions with p-TsOH and hydroquinone to inhibit autopolymerization of the DEPMA, monomer 15 was synthesized in 37% yield. FIGS. 18 and 19 are the $^1$H and $^{13}$C NMR spectra, respectively. Monomer 15 was then polymerized with AIBN under 65° C. with a ratio of AIBN to monomer of 1:43. After 22 h, the vinyl peaks from 15 were gone in the NMR spectrum, suggesting 100% monomer conversion. Dialysis against $H_2O$ and lyophilization resulted in P2 with an $M_n$ of 30,100 g/mol and a PDI of 2.03 (FIG. 20).

Scheme 12. Synthesis of Glycomonomer 15 and Free Radical Polymerization of 15 Mediated by AIBN.

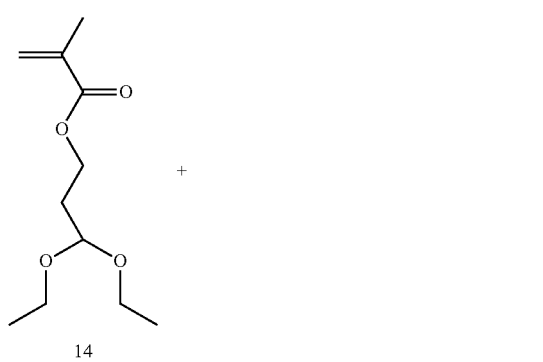

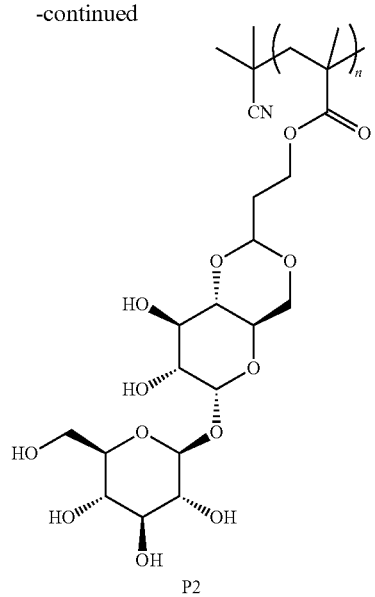

P2

Production of Glycopolymers P3

Figure 21:
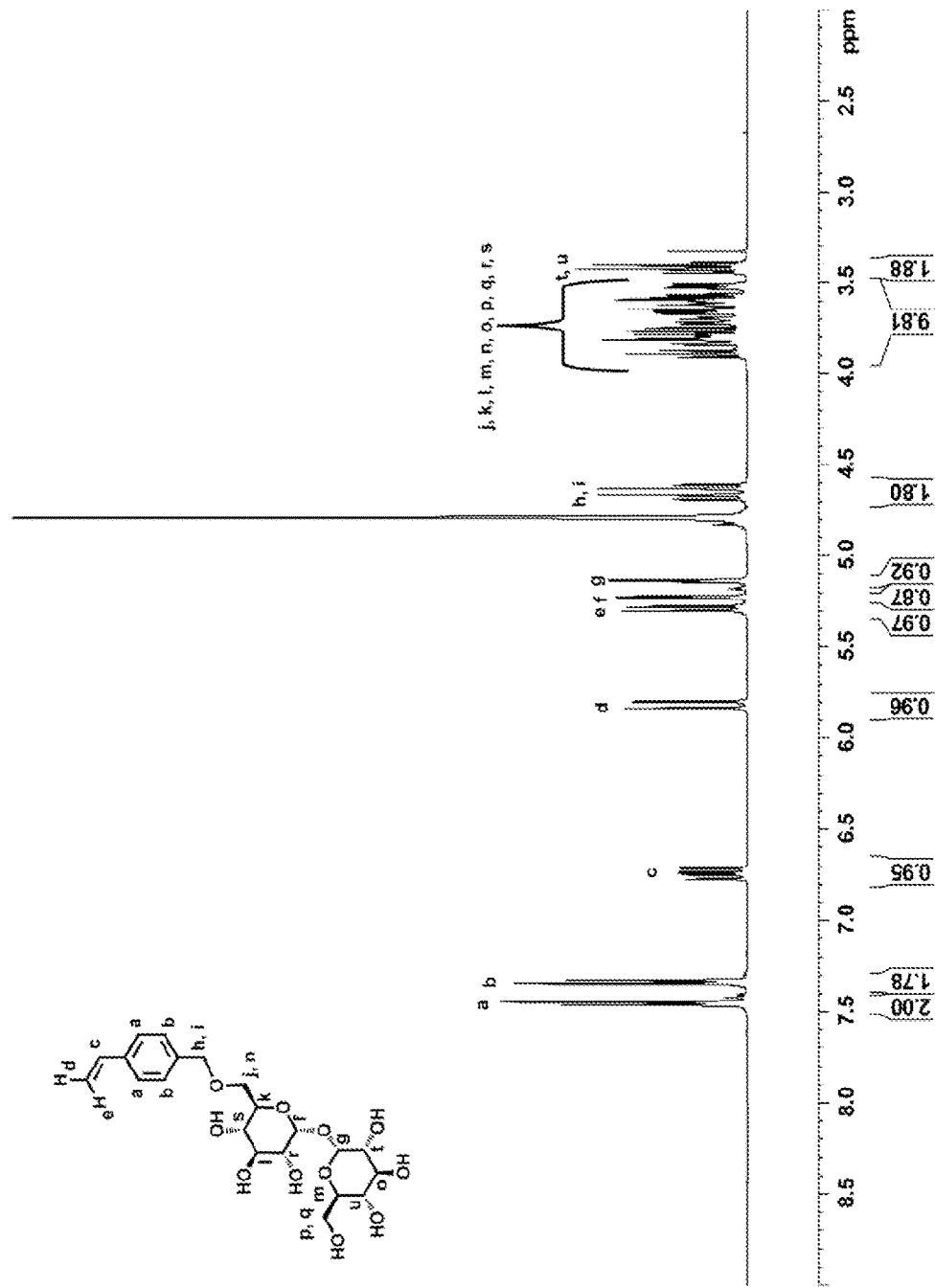
FIG. 21 is a graph showing $^1$H spectra of the monomer to form polymer P3 (in $D_2$O).
Figure 22:
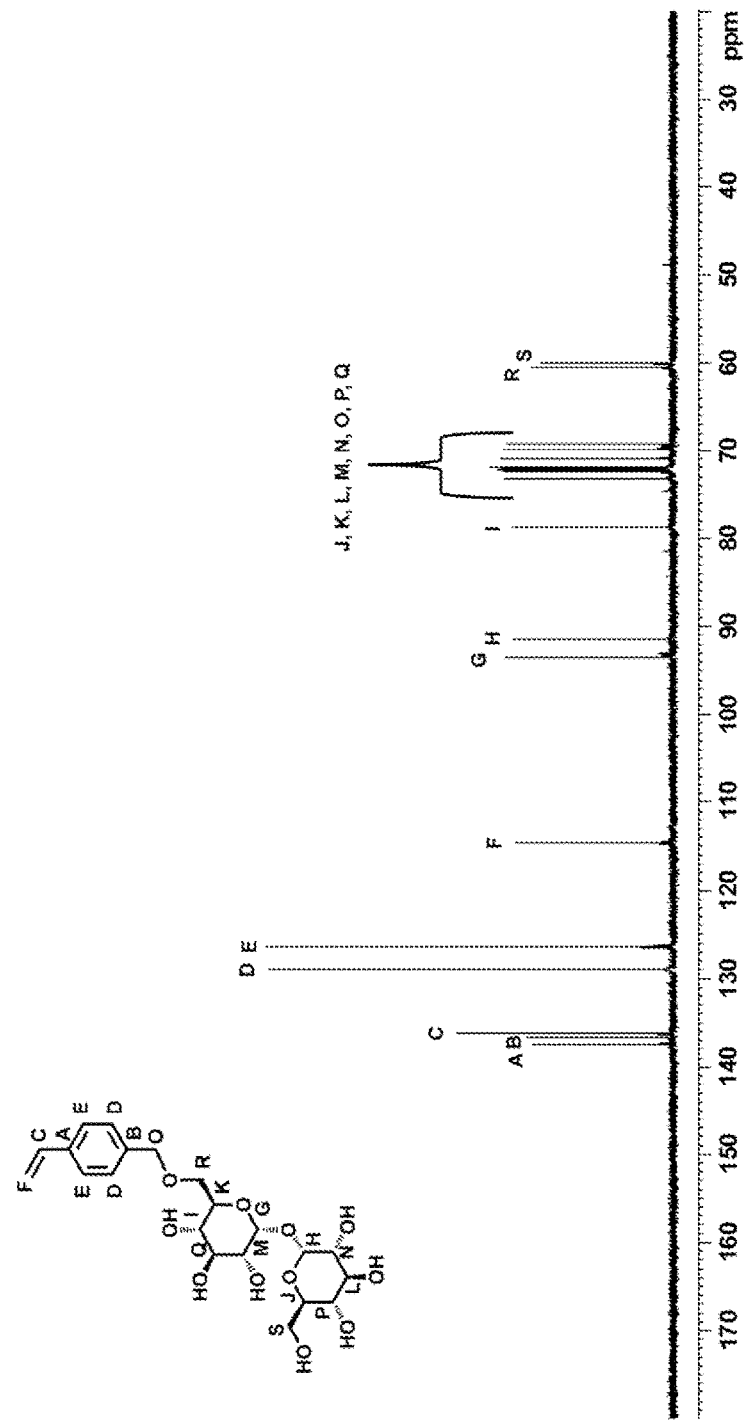
FIG. 22 is a graph showing $^{13}$C NMR spectra of the monomer to form polymer P3 (in $D_2$O).
Figure 23:
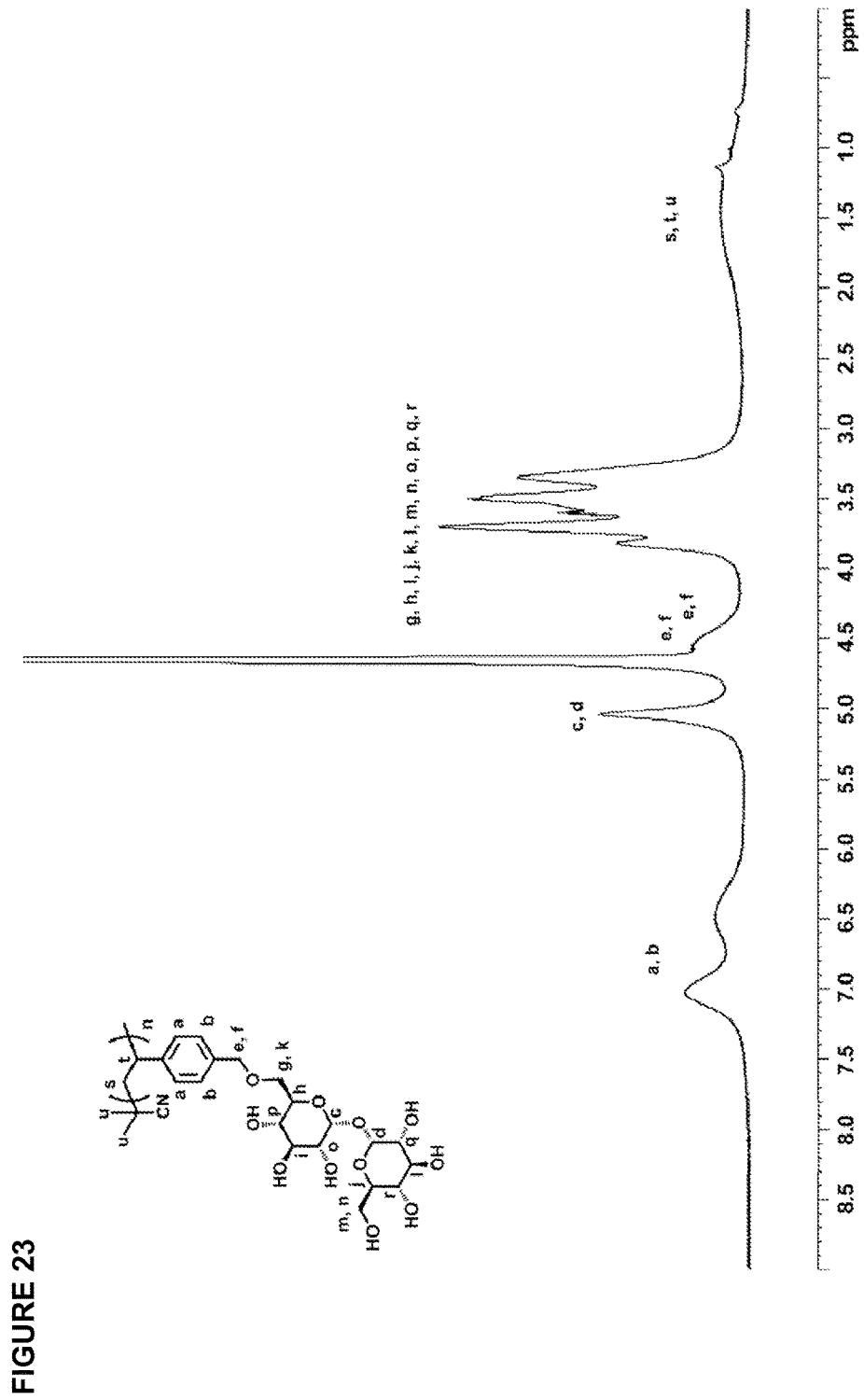
FIG. 23 is a graph showing $^1$H spectra of polymer P3 (in $D_2$O).

Another monomer 16 was synthesized in one step from the starting material, 4-vinyl benzyl chloride by slight modification of a literature procedure (Teramoto and Shibata, 2004). Trehalose was dissolved in dimethyl sulfoxide (DMSO) with NaOH and 4-vinyl benzyl chloride was slowly added into the solution. After 24 h under 25° C., the DMSO solution was added drop-wise into dichloromethane (DCM) to give white precipitate. The precipitate was dried and by HPLC purification monomer 16 was collected as a white powder in 20% yield (FIG. 21 and FIG. 22 are the NMR spectra). Polymerization of 16 was performed in 1:1=DMF:$H_2O$. Under 75° C. for 24 h, the polymerization was stopped and purified by dialysis against $H_2O$ (NMR spectrum, FIG. 23).

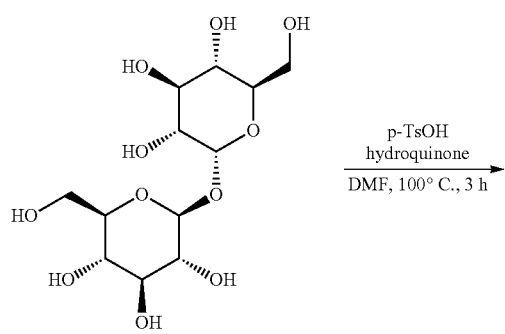

Scheme 13. Synthesis of Glycomonomer 16 and Free Radical Polymerization of 16 Mediated by AIBN.

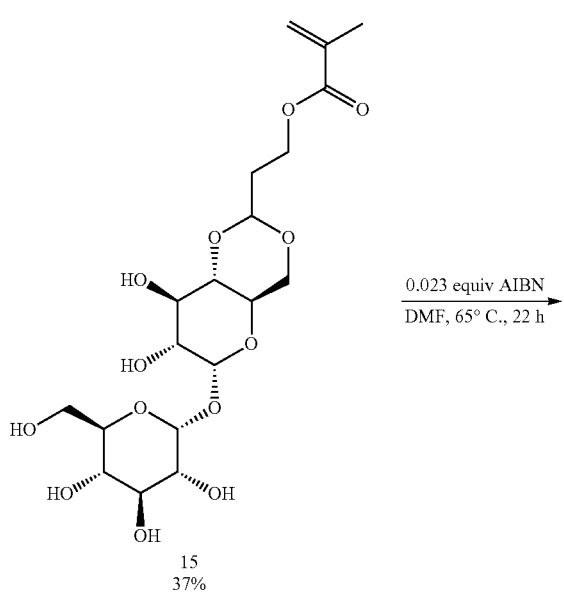

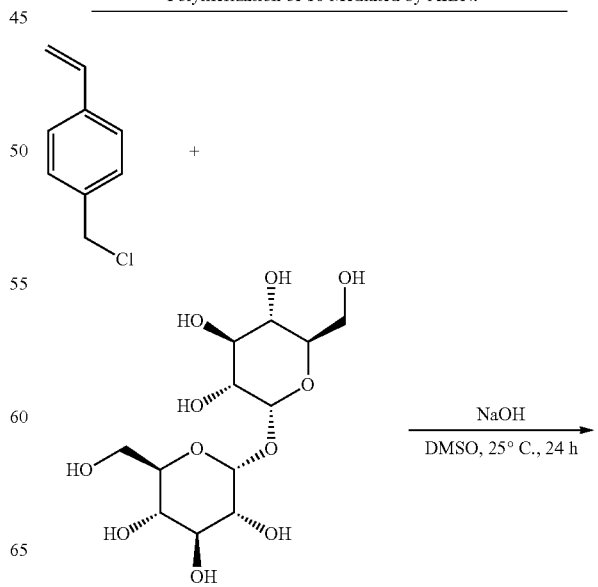

-continued

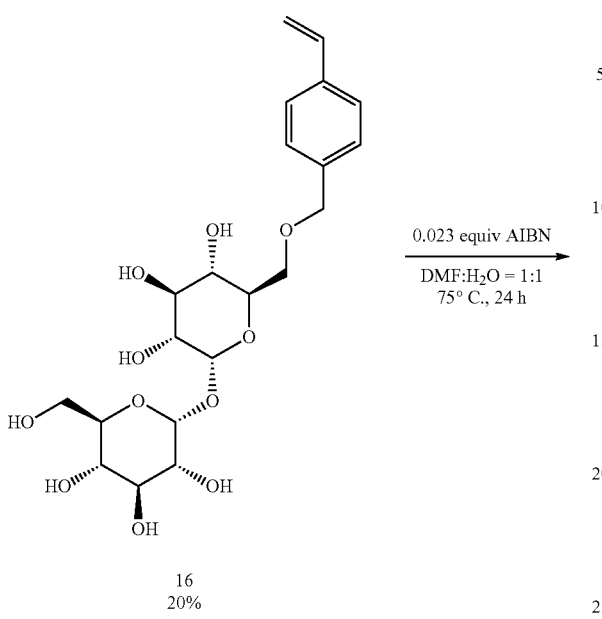

16
20%

P3

Figure 27:
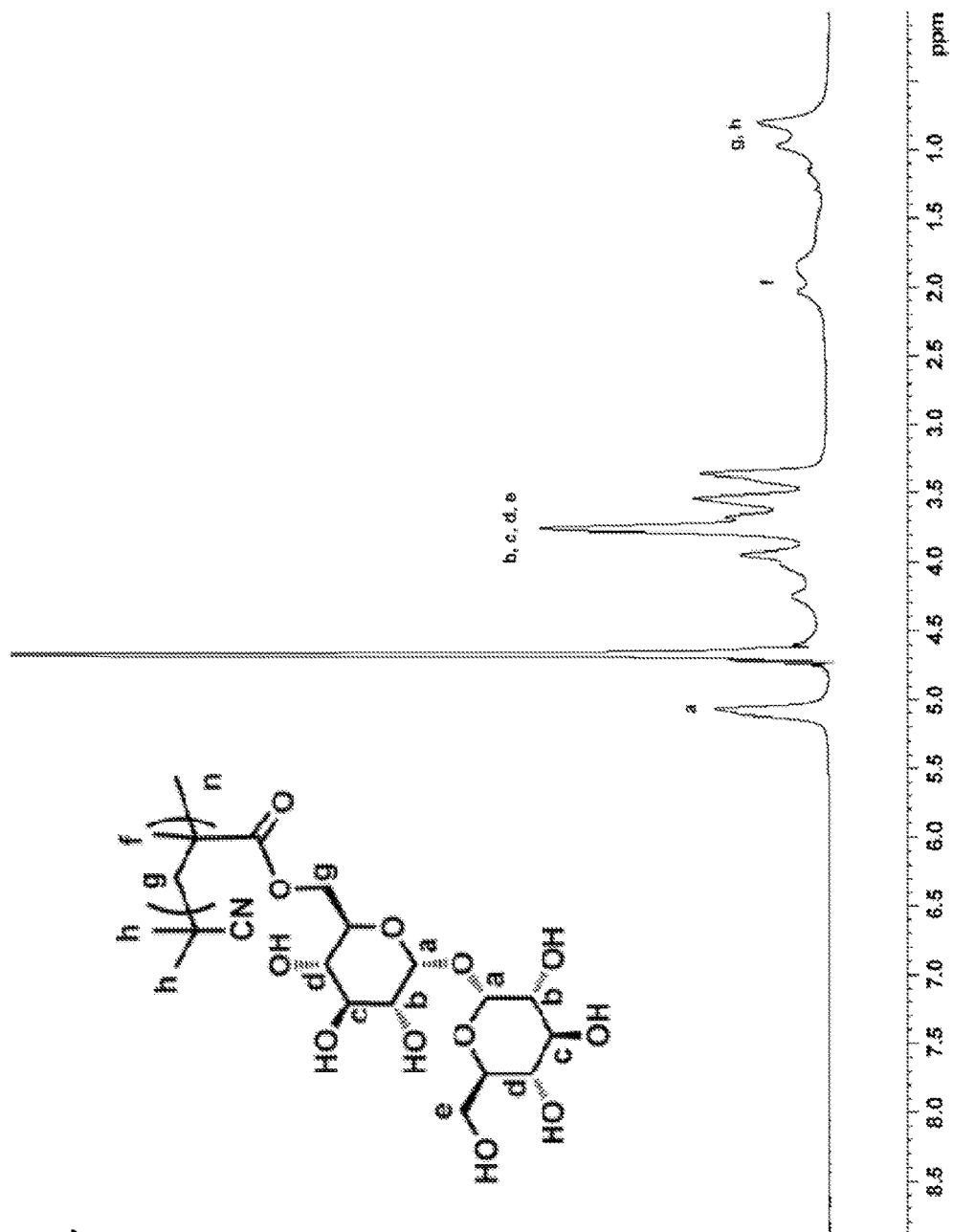
FIG. 27 is a graph showing $^1$H spectra of polymer P4 (in D$_2$O).

P4' had a $M_n$ of 18,292 g/mol and PDI=2.40. P4' was then deprotected by catalytic amount of NaOMe by modifying our previous report, and the product precipitated out as the deprotection occurred (Vazquez-Dorbatt and Maynard, 2006; Ambrosi, Batsanov, et al., 2002). P4 was neutralized with HCl and dialyzed against $H_2O$. From $^1$H-NMR spectroscopy, the peak of OAc methyl protons around 2 ppm disappeared (FIG. 27). From IR, the disappearance of the acetyl C=O and C—O stretches, and the appearance of the O—H absorption were observed.

Scheme 14. Synthesis of Glycomonomer 19 and Free Radical Polymerization of 19 Mediated by AIBN.

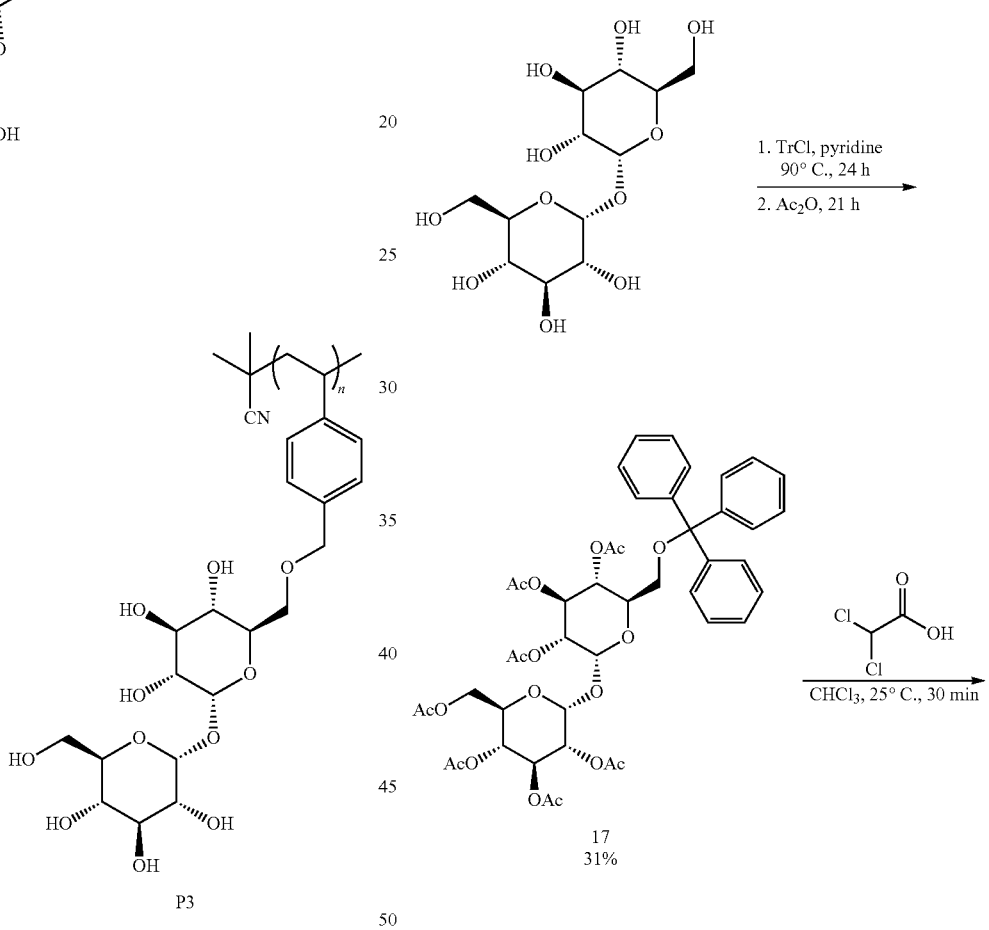

17
31%

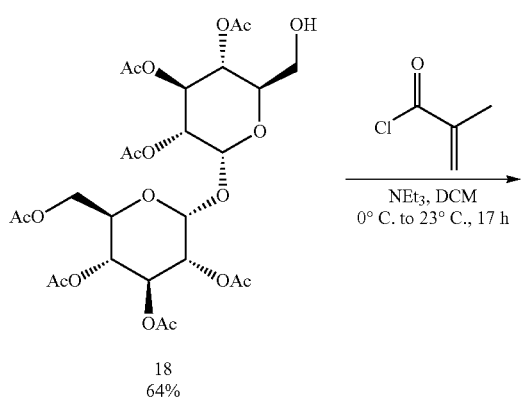

18
64%

Production of Glycopolymers P4

Figure 24:
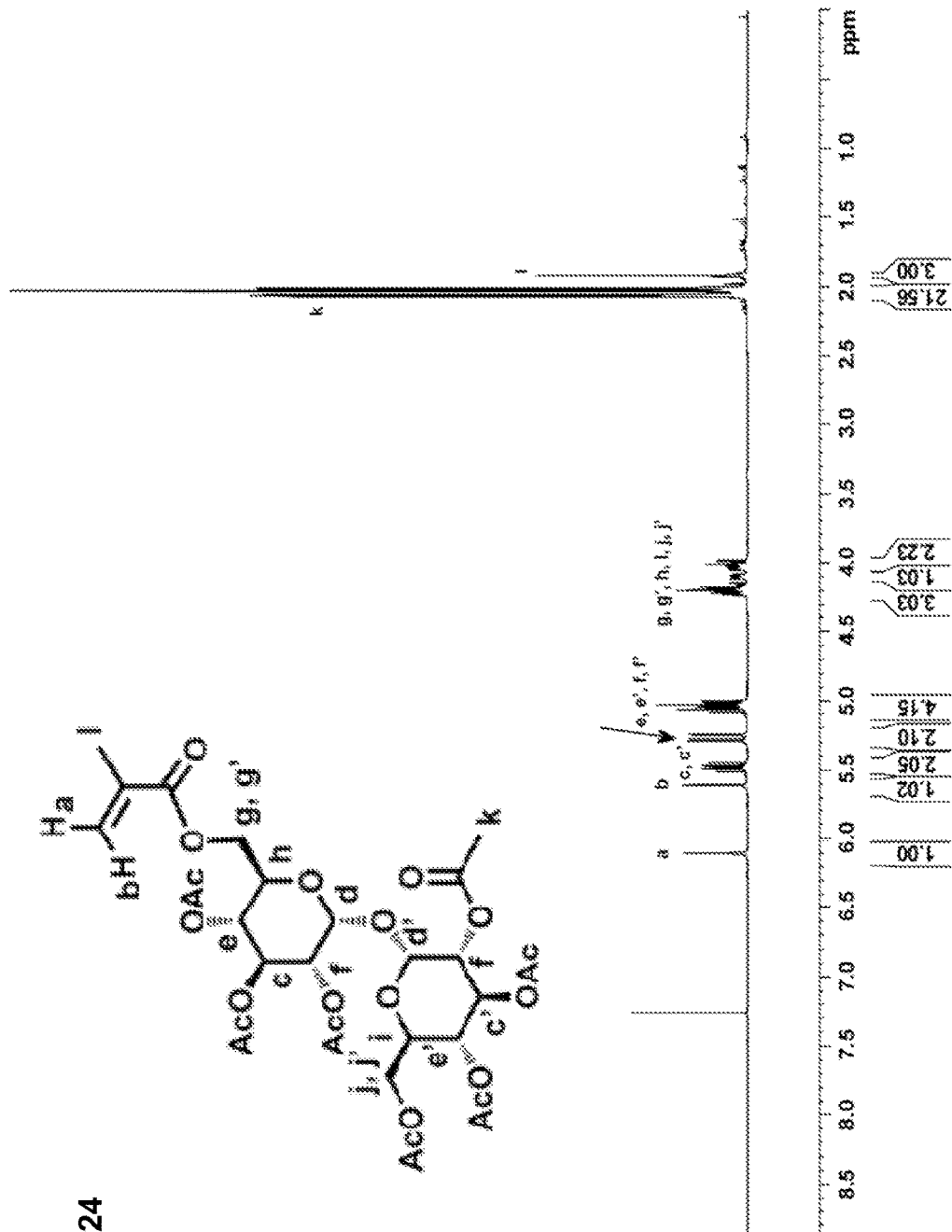
FIG. 24 is a graph showing $^1$H spectra of the monomer to form polymer P4' (in $CDCl_3$).
Figure 25:
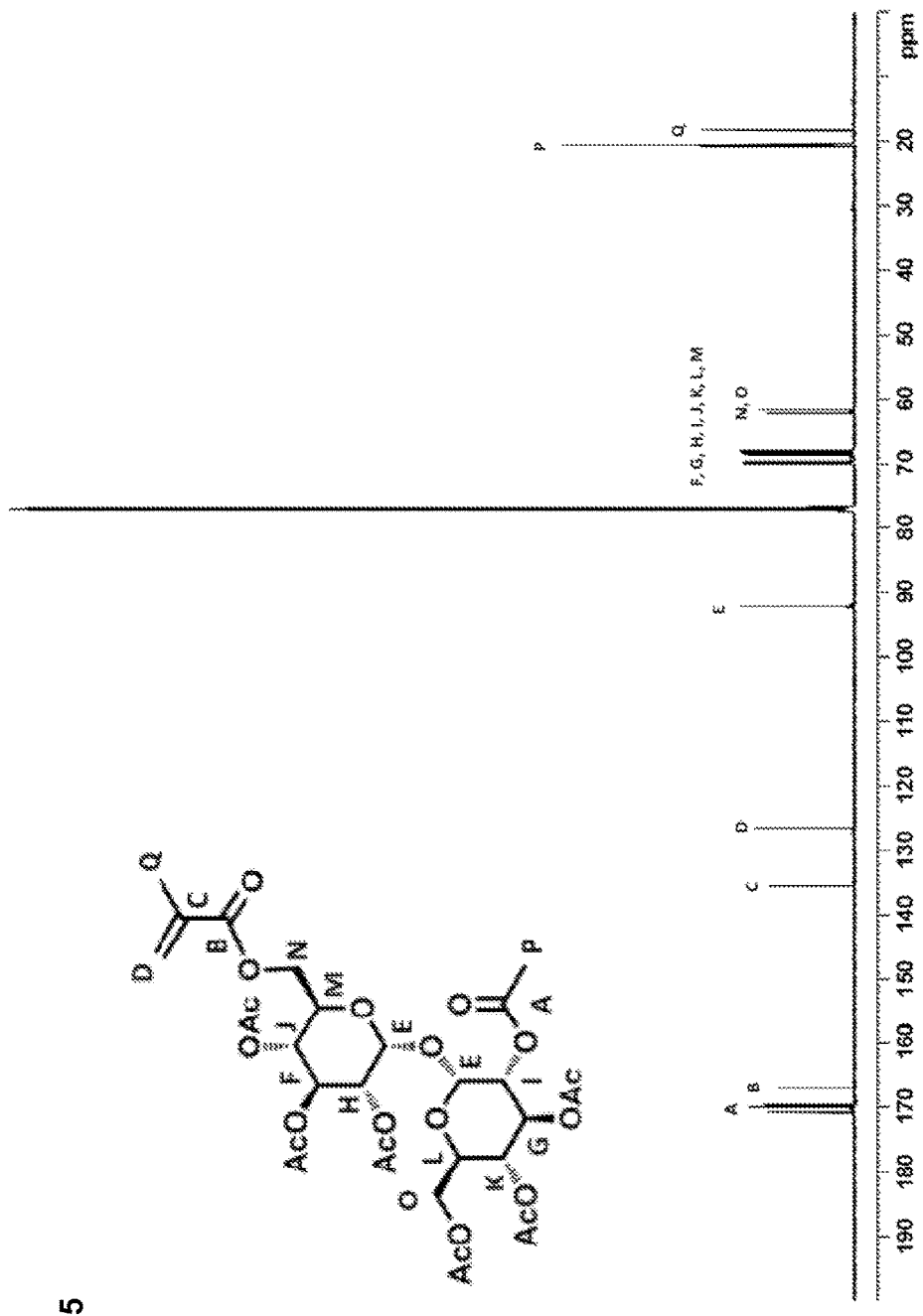
FIG. 25 is a graph showing $^{13}$C NMR spectra of the monomer to form polymer P4' (in $CDCl_3$).
Figure 26:
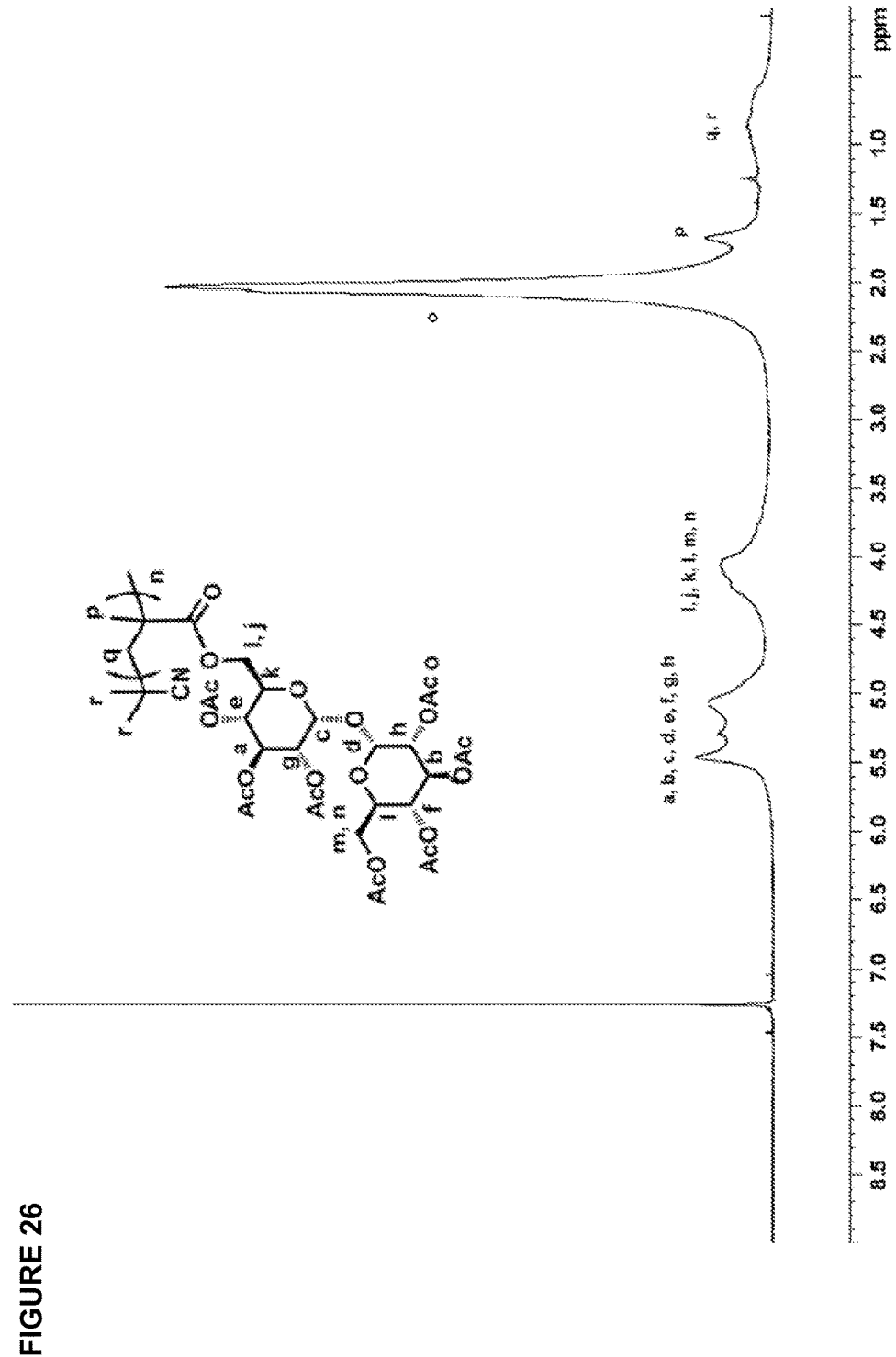
FIG. 26 is a graph showing $^1$H spectra of polymer P4' (in $CDCl_3$).

Another monomer was synthesized through specifically protecting one of the primary alcohols and adding a methacrylate moiety to that position (Scheme 14). 17 and 18 was synthesized by modifying a previous literature procedure (Kurita, Masuda, et al., 1994). The trityl group was used to discriminate the primary and secondary hydroxyl groups. Trehalose was first tritylated, then acetylated, and then the trityl group was removed to give 18 with only one free hydroxyl group at the 6th position. Compound 18 was then reacted with methacryoyl chloride to give the acetyl protected methacrylate glycomonomer 19 with 63.9% yield (FIG. 24 and FIG. 25). Monomer 19 was then polymerized with AIBN at 65° C. for 19 h. However, after purification by precipitation in diethyl ether (NMR provided as FIG. 26),

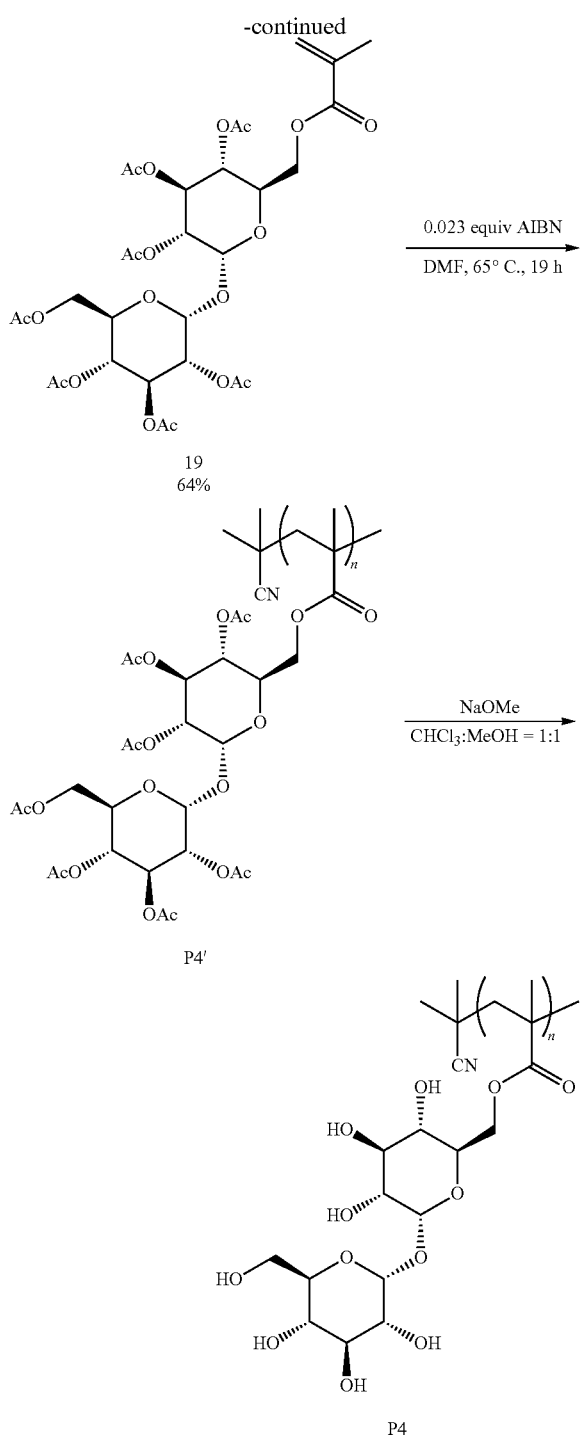

Stability Studies
Horseradish Peroxidase (HRP)

Figure 28:
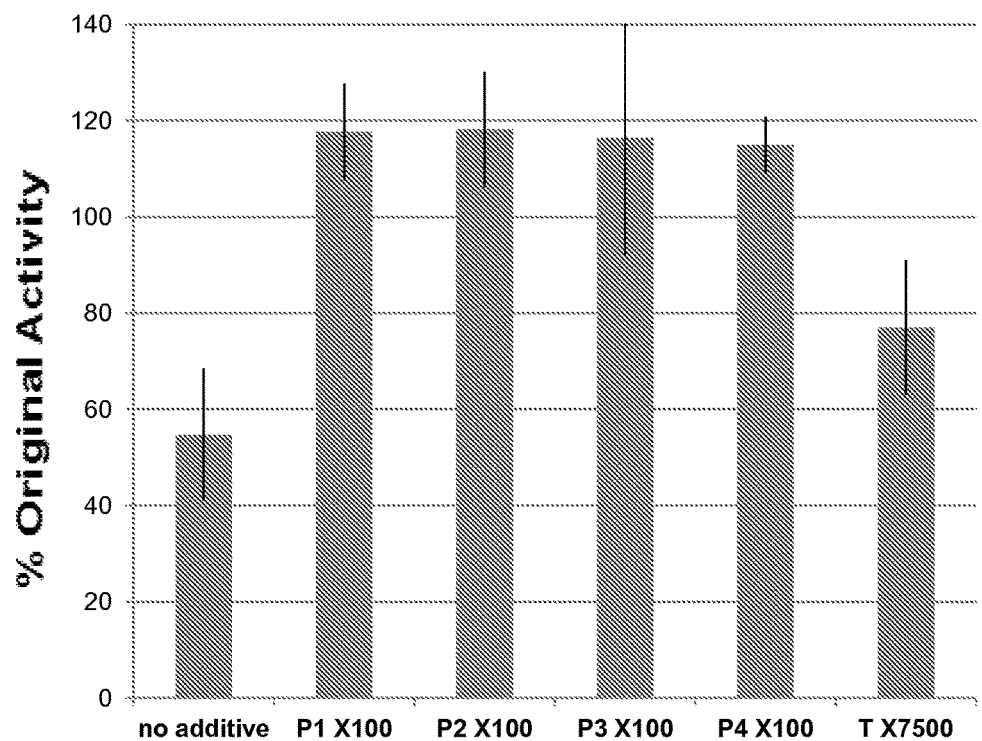
FIG. 28 is a graph showing activity of HRP (75 µg/mL) after 30 min heating under 70° C., with no additive, 100 equiv of P1, P2, P3, P4, and 7500 equiv of trehalose to the horseradish peroxidase (HRP).

The activity of horseradish peroxidase (HRP) after exposure to a temperature of 70° C. for 30 minutes was tested, and the results are provided in FIG. 28. The activity of HRP was tested through reaction with 3,3',5,5'-tetramethylbenzidine (TMB), which produces a blue by-product. HRP samples were prepared without any additive, with 100 equivalent of P1-P4, or 7500 equivalent of trehalose, which is equal to the trehalose in the P1 sample. Heated samples were then tested for HRP reactivity and the percent original activities were calculated using same concentration of HRP without heating and additive (FIG. 28). After heating, HRP in solution without any additive, only 46% of the original activity was observed. Yet, all of the glycopolymers (P1-P4) significantly stabilized the protein, and 100% of the original enzymatic activity remained. The same concentration of trehalose maintained only 80% of HRP activity. All samples were repeated six times and their p value compared with no additive were <0.001.

Glucose Oxidase (GOX)

Figure 29:
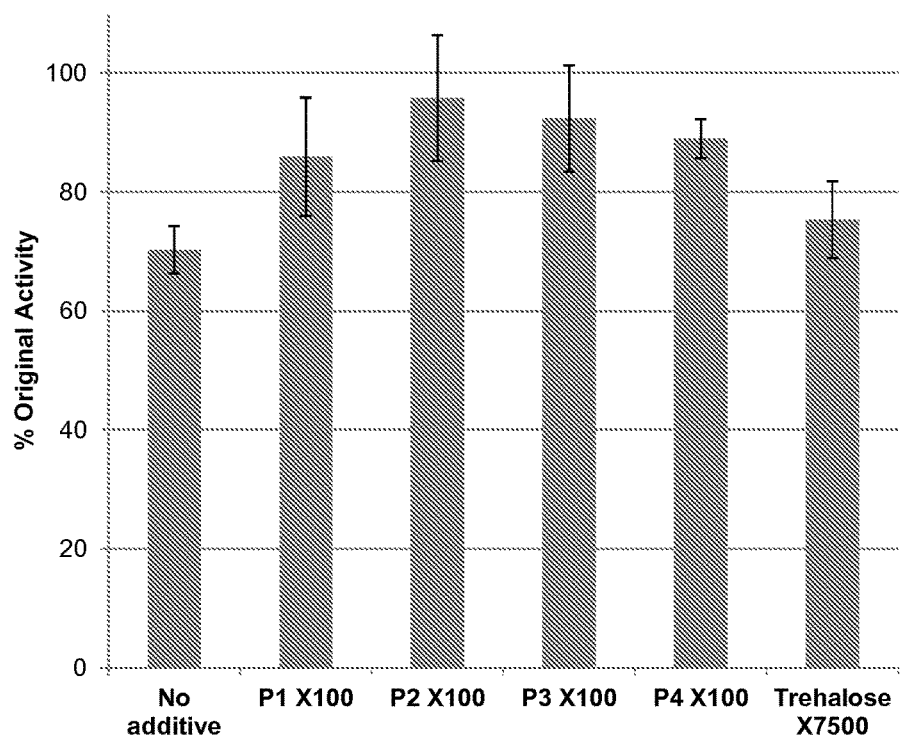
FIG. 29 is a graph showing activity of glucose oxidase (GOX; 100 µg/mL) after 30 min heating under 50° C., with no additive, 100 equiv of P1, P2, P3, P4, and 7500 equiv of trehalose to the GOX.

Trehalose glycopolymers P1 through P4 were also tested for glucose oxidase (GOX) stabilization against 50° C. heat for 30 min. The activity of GOX was evaluated using Amplex® Red Glucose/Glucose Oxidase Assay Kit (Invitrogen). GOX reacts with D-glucose to form $H_2O_2$, which can then react with the Amplex® in the presence of horseradish peroxidase (HRP) to generate resorufin and can be detected by fluorescence. GOX samples were prepared without any additive, with 100 equivalent of P1-P4, and 7500 equivalent of trehalose, which is equal to the number of repeating units in the P1. All samples were heated to 50° C. for 30 min and repeated six times. Heated samples were then tested for GOX reactivity and percent original activities were calculated using same concentration of GOX without heating and additive (FIG. 29). The result shows that trehalose glycopolymers, P1, P2, P3, and P4 all maintained the activity of GOX over 85% while GOX without additive had 68% of its activity with p<0.01, p<0.001, and p<0.001, respectively, showing statistical significance. Also, all polymers showed successful stabilization compared to only trehalose, which maintained 72% of the original activity p<0.05.

Insulin

Figure 30:
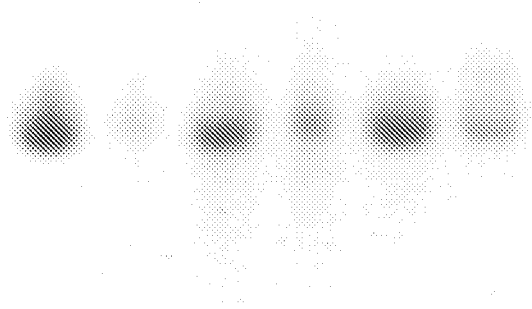
FIG. 30 is a graph showing a comparison between a native gel and insulin with polymers P1-P3 or trehalose (T).

Prepared P1, P2, P3, and the same concentration of trehalose as an additive were tested for stabilization of insulin against heating under 90° C. for 1 h. After heating all the samples were loaded on the native gel (FIG. 30). Insulin without any additive was denatured and the band was almost gone in native gel. The band of the insulin with trehalose added was greatly reduced. However, the insulin with P1 and P3 clearly showed that most of the insulin band remained, which indicated the protein structure was mostly unchanged. The band of insulin with P2 was weaker compare to P1 and P3, but it was stronger than without any additive or with trehalose. The MALDI-TOF data provides that insulin, originally 5.8 kDa, denatures into mainly two fragments after heating (data not shown). This is due to the breakage of two disulfide bridges liking α and β chain of insulin.

β-Galactosidase (β-Gal)

Figure 31:
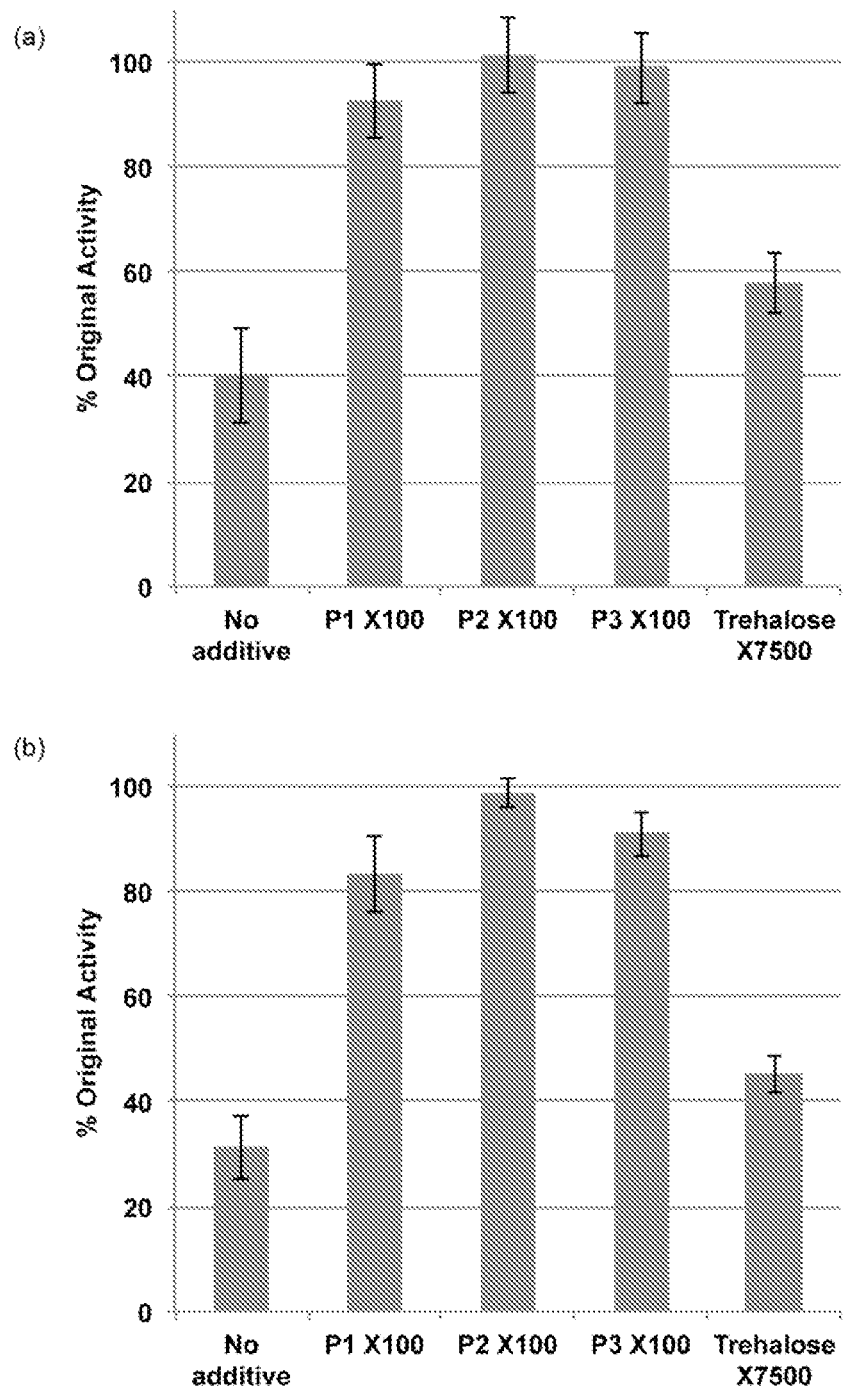
FIGS. 31a and b are a set of graphs showing activity of β-galactosidase (β-Gal; 100 µg/mL) after (a) 3rd, and (b) 4th cycles with no additive, 100 equiv of P1, P2, P3, and 7500 equiv of trehalose to the β-Gal.

The stabilization of β-galactosidase (β-Gal) was also tested after multiple lyophilization cycles. β-Gal is known to be easily denatured by lyophilization or freeze-thaw cycles (Pikal-Cleland and Capenter, 2001). Activity of β-Gal was measured by reacting with o-nitrophenyl-β-D-galactoside (ONPG), which releases o-nitrophenol, a yellow color product that absorbs light at 420 nm. The experiments were repeated six times and the results showed that trehalose glycopolymers are efficient excipients that can protect activity of β-Gal against lyophilization cycles. After 3 cycles of lyophilization, β-Gal had 40% of its original activity and only 30% activity more after the 4th cycle, while P1 through P3 maintained activity from 83 to 98%, depending on the polymer even after 4 cycles. The polymers outperformed trehalose, since the trehalose maintained only 45% of the original activity (FIG. 31).

The heating experiments for HRP, GOX, and insulin and lyophilization experiment for β-Gal all suggests that trehalose glycopolymers can be used as additives to stabilize various proteins against heat and lyophilization stresses. Each time, the polymers outperformed trehalose itself.

Examination of Cytotoxicity

Figure 32:
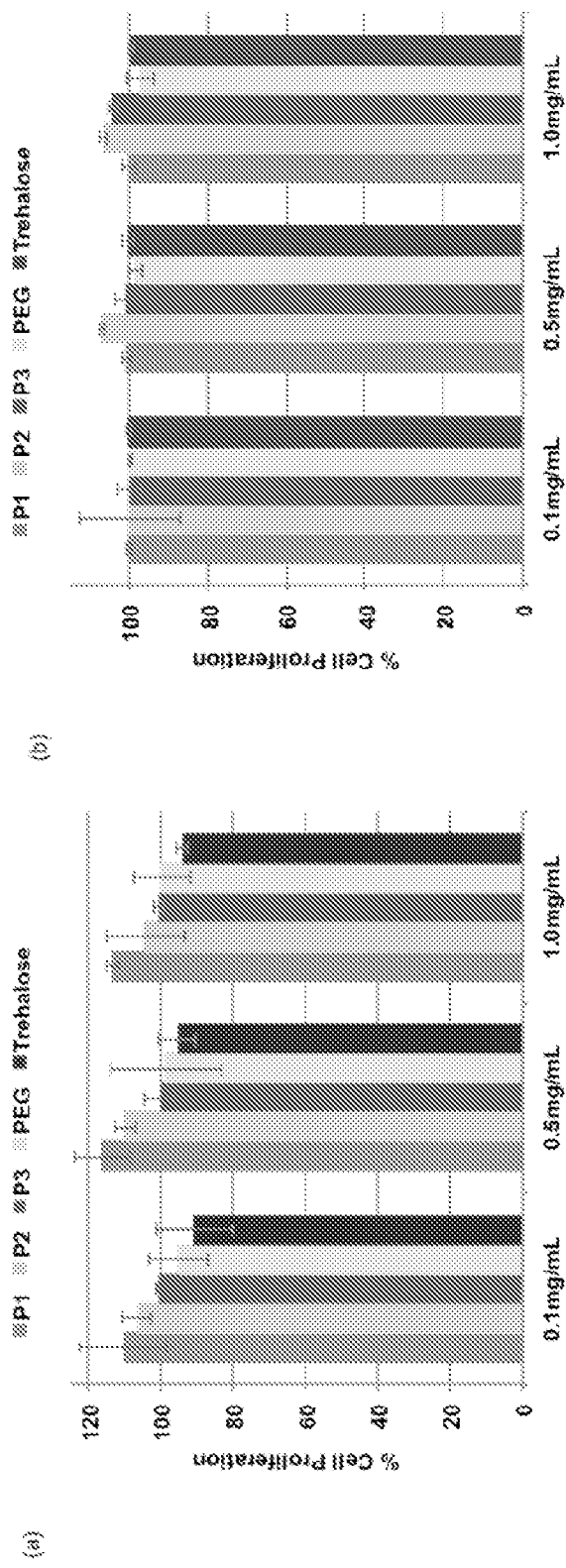
FIG. 32a, b, and c are a set of graphs showing cytotoxicity assay of P1-P3, 20 kDa PEG, and trehalose with (a) NIH 3T3, (b) RAW 264.7, (c) HDF, and (d) HUVEC cells.
Figure 32:
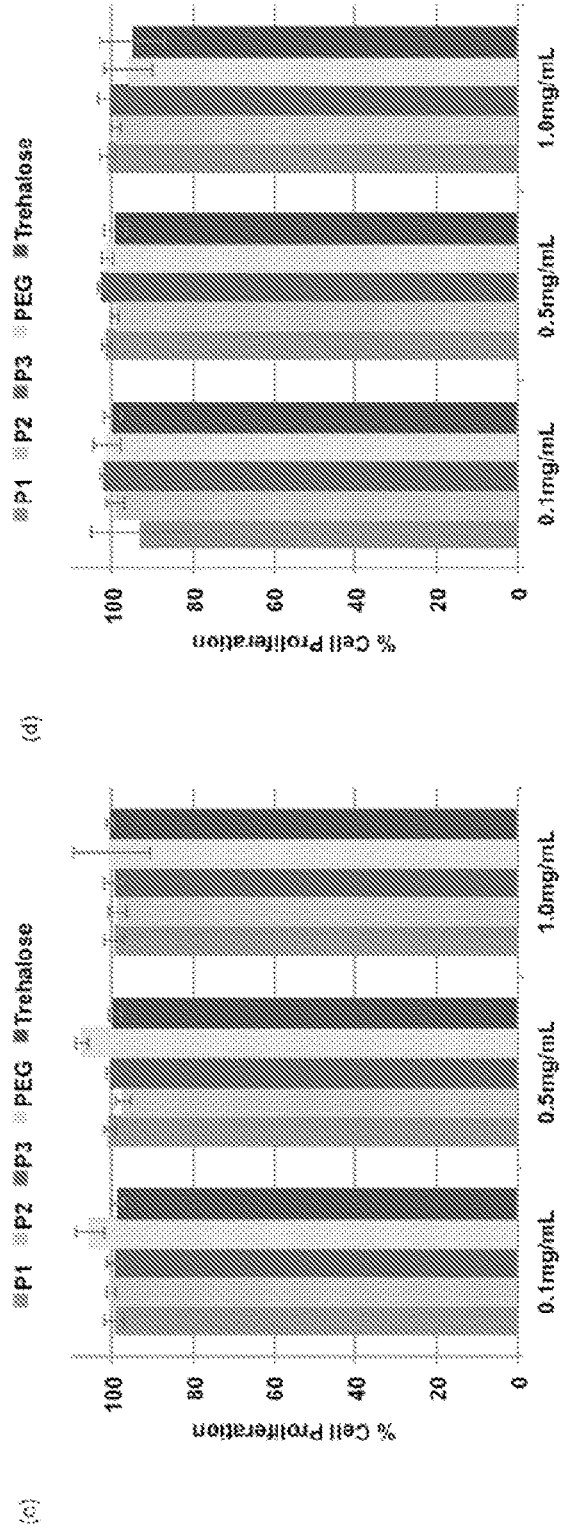

To examine the possibility of these trehalose glycopolymer in vivo, the cytotoxicities of P1, P2, and P3 along with 20 kDa PEG and trehalose as comparisons were tested. NIH 3T3 (mouse fibroblasts), RAW 264.7 (mouse leukemic monocyte macrophages), HDF (human dermal fibroblasts), and HUVEC (human umbilical vein endothelial cells) were separately cultured and were seeded in 48-well plates at a density of $5\times10^3$ cells per well. After 24 hours, culture media were replaced with the working medium containing each polymer or trehalose with concentrations of 0.1, 0.5, and 1 mg/mL After 48 h incubation, the cells were stained with the LIVE/DEAD reagent and fluorescent images were captured for each well. Live and dead cells were counted, and the percent cell viability was calculated by dividing the number of live cells by the total number of cells. All experiments were conducted with four repetitions and averaged, and results shown in FIG. 32. The data confirm that P1-P3 trehalose glycopolymers are non-cytotoxic to all the tested four cell lines tested. Also, compared to the 20 kDa PEG and trehalose, P1, P2, P3 did not exhibit any cytotoxicity, which is important for their applicability for use in vivo.

Method and Synthesis

Free Radical Polymerization of 1.

Glycomonomer 14 (391.8 mg, $8.58\times10^{-1}$ mmol) was dissolved in DMF (1.07 mL). AIBN (3.28 mg, $2.00\times10^{-2}$ mmol) was added to the solution. Five cycles of freeze-pump-thaw were repeated, and the reaction was initiated by immersion in an oil bath at 80° C. The polymerization was stopped by cooling with liquid nitrogen after 17 h with 100% monomer conversion by $^1$H NMR spectroscopy. The product was purified by dialysis against $H_2O$ for 3 days (MWCO 3,500 g/mol) and dried using a lyophilizer resulting P1. $M_n$ of the polymer was 34,300 g/mol and PDI was 1.96 by GPC. $^1$H NMR (500 MHz in $D_6$DMSO) δ: 7.11, 6.39, 5.45, 5.23, 4.96, 4.86, 4.41, 4.12, 3.97, 3.78, 3.70, 3.62, 3.48, 3.17, 1.60, 1.24, 0.86. IR: ν=3384, 2916, 1635, 1380, 1150, 1074, 983 $cm^{-1}$.

Synthesis of 15.

Trehalose (3.96 g, $1.16\times10^{-2}$ mol) was dissolved in 100° C. DMF (72 mL). p-TsOH (44 mg, $2.31\times10^1$ mmol) and hydroquinone (12.73 mg, $1.16\times10^{-1}$ mmol) were added into the solution. After stirring for 5 min, 14 (500 mg, 2.31 mmol) was added to the reaction slowly. After 3 h, the reaction was stopped and the solvent was removed in vacuo. The crude product was purified by HPLC (50% MeOH in $H_2O$) and lyophilized resulting white powder (403.6 mg) with 37% yield. $^1$H NMR (500 MHz in $D_6$DMSO) δ: 6.04 (s, 1H), 5.68-5.67 (t, J=1.59 Hz, 1H), 5.10-5.09 (d, J=5.31 Hz, 1H), 4.93-4.89 (m, 3H), 4.83-4.82 (d, J=3.50 Hz, 1H), 4.78-4.76 (m, 2H), 4.70-4.68 (t, J=5.00 Hz, 1H), 4.36-4.33 (t, J=5.95 Hz, 1H), 4.16-4.13 (m, 2H), 3.97-3.94 (m, 1H), 3.89-3.84 (m, 1H), 3.69-3.64 (m, 2H), 3.57-3.53 (m, 2H), 3.49-3.41 (m, 2H), 3.35 (1H), 3.26-3.22 (m, 1H), 3.17-3.12 (m, 2H), 2.01-1.88 (m, 5H). $^{13}$C NMR (500 MHz in $D_6$DMSO) δ: 166.9, 136.1, 126.2, 99.2, 94.5, 94.1, 81.4, 73.0, 73.0, 72.4, 71.8, 70.3, 69.8, 68.1, 62.7, 61.0, 60.6, 33.5, 18.3. IR: ν=3365, 2934, 1713, 1636, 1305, 1148, 979 $cm^{-1}$. ESI-MS (±1.0) observed (predicted): Na$^+$ 489.1577 (489.1584).

Free Radical Polymerization of 15.

15 (153 mg, $3.28\times10^{-1}$ mmol) was dissolved in DMF (1.64 mL) and AIBN (1.25 mg, $7.61\times10$-3 mmol) was added to the reaction flask. Freeze-pump-thaw cycles were repeated five times, and the reaction was initiated by immersion in an oil bath at 65° C. After 22 h, the monomer conversion was 100% by $^1$H NMR, and the polymerization was stopped by cooling in liquid nitrogen. The polymer was dialyzed against $H_2O$ (MWCO 3,500 g/mol) and lyophilized to result in P2 with $M_n$=30,100 g/mol and PDI=2.03. $^1$H NMR (500 MHz in $D_6$DMSO) δ: 5.15, 4.94, 4.85, 4.67, 4.38, 3.98, 3.88, 3.69, 3.57, 3.48, 3.17, 1.90, 1.23, 0.83. IR: ν=3374, 2932, 1716, 1638, 1384, 1273, 1146, 1047, 984 $cm^{-1}$.

Synthesis of 16.

16 was synthesized by modifying a literature procedure where the trehalose was substituted on multiple hydroxyl groups (Teramoto and Shibata, 2004). NaOH (4.44 g, $1.14\times10^{-1}$ mol) was added to DMSO (96 mL) and stirred for 5 min. Trehalose (4.86 g, $1.42\times10^{-2}$ mol) was then added to the reaction flask. After all the trehalose dissolved, 4-vinyl benzyl chloride (0.4 mL, 2.84×10'3) was slowly added and reaction solution changed to bright yellow. The reaction was stirred for 24 h at 25° C. and precipitated into 4 L of DCM under ice bath. Precipitates were dried in vacuo and purified by HPLC (50% MeOH in $H_2O$). After lyophilization the desired monosubstituted product (261.1 mg) was obtained as white powder with 20% yield. $^1$H NMR (500 MHz in $D_2O$) δ: 7.47-7.45 (m, 2H), 7.35-7.33 (m, 2H), 6.77-6.71 (m, 1H), 5.84-5.80 (d, J=17.69 Hz, 1H), 5.30-5.28 (d, J=11.42 Hz, 1H), 5.23-5.22 (d, J=3.68 Hz, 1H), 5.14-5.13 (d, J=4.05 Hz, 1H), 4.69-4.61 (m, 2H), 3.91-3.51 (m, 10H), 3.45-3.39 (m, 2H). $^{13}$C NMR (500 MHz in $D_2O$) δ: 137.5, 136.6, 136.2, 128.9, 126.4, 114.7, 93.5, 91.4, 78.7, 73.2, 72.4, 72.2, 72.0, 72.0, 71.0, 69.8, 69.2, 60.6, 60.1. IR: ν=3369, 2931, 1642, 1408, 1368, 1147, 1083, 1044, 989 $cm^{-1}$. ESI-MS (±1.0) observed (predicted): Na$^+$ 481.1692 (481.1686).

Free Radical Polymerization of 16.

16 (146.4 mg) and AIBN (1.22 mg) were dissolved in $H_2O$ (0.6 mL) and DMF (0.6 mL), respectively. Both solutions were added to reaction flask and after five cycles of freeze-pump-thaw, the polymerization was started by placing the reaction vessel in a 75° C. oil bath. After 24 h, the polymerization was stopped by cooling with liquid nitrogen. The resulting polymer was dialyzed against $H_2O$ (MWCO 3,500 g/mol) for 3 days for purification and lyophilized to obtain white powder. The resulting polymer did not dissolved in DMF, however the aqueous GPC trace showed a similar molecular weight compared to P1 and P2. $^1$H NMR (500 MHz in $D_2O$) δ: 7.04, 6.48, 5.04, 4.55, 3.82, 3.70, 3.60, 3.50, 3.35, 1.48, 1.14. IR: ν=3341, 2932, 1654, 1510, 1424, 1367, 1147, 1080, 1046, 987 cm-1.

Synthesis of 17.

17 was synthesized modifying a previous literature where the trehalose was substituted with a trityl group on multiple hydroxyl groups (Kurita, Masuda, et al., 1994). Trehalose (4.91 g, 14.35 mmol, 1.5 eq) was stirred in 20 mL pyridine for 30 min. Trityl chloride (TrCl, 2.67 g, 9.57 mmol, 1.0 eq) was then added, and the reaction mixture was stirred under Ar at 90° C. for 24 h. After cooling to room temperature, acetic anhydride (12 mL, 127.2 mmol, 13.3 eq) was added, and the reaction mixture was stirred under Ar at 23° C. for 21 h. Pyridine was removed under high vacuum. To the crude solid, $H_2O$ was added and extracted with $CHCl_3$, the organic layer was then sequentially washed with 0.1 N HCl, $H_2O$, sat. $NaHCO_3$, and brine. The organic layer was then dried with $MgSO_4$ and concentrated under reduced pressure. The crude was purified through silica gel flash chromatography with EtOAc/Hexane=3/4+1% $NEt_3$ ($R_f$~0.3) to obtain 2.62 g white solid with 31% yield. $^1$H NMR (500 MHz in $CDCl_3$) δ: 7.38-7.21 (m, 15H), 5.50-5.45 (m, 2H), 5.40-5.37

(dd, J=3.85, 7.85 Hz, 2H), 5.18-5.15 (dd, J=3.85, 10.2 Hz, 2H), 5.13-5.06 (m, 2H), 4.27-4.23 (m, 1H), 4.14-4.04 (m, 3H), 3.10-3.03 (m, 2H), 2.11-1.74 (s, 21H). $^{13}$C NMR (500 MHz in CDCl$_3$) δ: 170.81, 170.25, 170.12, 169.91, 169.72, 169.69, 169.30, 143.47, 128.71, 128.01, 127.24, 92.51, 92.48. 86.71, 70.43, 70.38, 70.27, 69.85, 69.61, 68.99, 68.67, 68.35, 61.94, 61.81, 20.88, 20.81, 20.79, 20.77, 20.67, 20.54. IR: ν=2956, 2941, 1746, 1449, 1367, 1239, 1213, 1072, 1030, 985, 962, 902, 805, 766, 749. ESI-MS (±1.0) observed (predicted): Na$^+$ 901.2892 (901.2895).

Synthesis of 18.

18 was synthesized modifying a previous literature where the trehalose was deprotected to reveal multiple hydroxyl groups (Kurita, Masuda, et al., 1994). 17 (1.69 g, 1.928 mmol) was dissolved in 8 mL CHCl$_3$, then 8 mL dichloroacetic acid was added and stirred at 23° C. for 30 min. The crude mixture was washed with H$_2$O once, and then with sat. NaHCO$_3$ three times. The organic layer was then dried with MgSO$_4$ and concentrated under reduced pressure. The crude was purified through silica gel flash chromatography with DCM+3% MeOH (R$_f$~0.25) to obtain 780 mg of a yellow solid in 64% yield. $^1$H NMR (500 MHz in CDCl$_3$) δ: 5.45-5.23 (m, 2H), 5.29-5.27 (t, J=3.85 Hz, 2H), 5.06-4.98 (m, 4H), 4.26-4.22 (dd, J=5.5, 12.2 Hz, 1H), 4.09-3.86 (m, 2H), 3.99-3.96 (dd, J=2.05, 12.2 Hz, 1H), 3.64-3.52 (m, 2H), 2.06-2.01 (s, 21H). $^{13}$C NMR (500 MHz in CDCl$_3$) δ: 170.61, 170.33, 169.97, 169.93, 169.88, 169.70, 169.60, 169.57, 92.97, 92.86, 70.83, 70.48, 70.06, 69.95, 69.93, 69.86, 69.75, 69.59, 68.79, 68.52, 68.46, 68.14, 61.77, 61.71, 60.95, 20.90, 20.71, 20.68, 20.67, 20.61, 20.58. IR: ν=3523, 2962, 2106, 1742, 1435, 1367, 1208, 1163, 1137, 1032, 986, 899, 802, 736 cm$^{-1}$. ESI-MS (+1.0) observed (predicted): Na$^+$ 659.1762 (659.1799).

Synthesis of 19.

18 (360 mg, 0.566 mmol, 1 eq) was dissolved in 1.9 mL dry DCM in an ice bath, then NEt$_3$ (1.18 mL, 8.48 mmol, 15 eq) was added. Methacryoyl chloride (0.55 mL, 5.66 mmol, 10 eq) was dissolved in 2 mL dry DCM, and the solution was added to the reaction mixture drop wise. The mixture was then stirred under Ar from 0° C. to 23° C. for 17 h. NEt$_3$Cl$^-$ salt was filtered off, and the solution was washed with 10% HCl, H$_2$O, sat. NaHCO$_3$, and then brine. The organic layer was then dried with MgSO$_4$ and concentrated under reduced pressure. The crude was purified through silica gel flash chromatography with EtOAc:Hexane=1:1 (R$_f$~0.4) to obtain 254.5 mg yellow oil in 64% yield. $^1$H NMR (500 MHz in CDCl$_3$) δ: 6.10 (s, 1H), 5.61 (s, 1H), 5.51-5.45 (m, 2H), 5.28-5.24 (dd, J=3.85, 17.75 Hz, 2H), 5.08-5.00 (m, 4H), 4.23-3.98 (m, 6H), 2.07-2.01 (s, 21H), 1.92 (s, 3H). $^{13}$C NMR (500 MHz in CDCl$_3$) δ: 170.60, 169.96, 169.95, 169.64, 169.55, 169.53, 169.50, 166.82, 135.52, 126.60, 92.28, 92.17, 70.08, 69.95, 69.87, 69.67, 68.69, 68.47, 68.19, 68.13, 62.09, 61.74, 20.68, 20.67, 20.62, 20.60, 20.58, 20.52, 18.21. IR: ν=2930, 1746, 1368, 1213, 1033, 897, 804 cm$^{-1}$. ESI-MS (±1.0). observed (predicted): Na$^+$ 727.2078 (727.2062).

Free Radical Polymerization of 19.

19 (221.9 mg, 0.315 mmol, 43 eq) and AIBN (1.2 mg, 0.0073 mmol, 1 eq) were weighed into a Schlenk tube and dissolved in 0.5 mL DMF. Freeze-pump-thaw cycles were repeated five times, and the reaction was initiated by immersion in an oil bath at 65° C. After 19 h, monomer conversion reached 83% by $^1$H NMR and the polymerization was stopped by cooling in liquid nitrogen. DMF was removed under high vacuum. The crude was redissolved in DCM and precipitated into cold diethyl ether three times. 160 mg of white solid P4' was collected with M$_n$=18,300 g/mol and PDI=2.40. $^1$H NMR (500 MHz in CDCl$_3$) δ: 5.46, 5.30, 5.28, 5.07, 4.20, 4.06, 2.07, 2.03, 1.68, 1.25, 0.85. IR: 2957, 1742, 1432, 1367, 1212, 1159, 1034, 896, 802, 746 cm$^{-1}$.

Deprotection of P4'.

P4' (100 mg, 0.142 mmol of monomer, 1 eq) was dissolved in 1 mL CHCl$_3$ and 1 mL MeOH, and stirred for 15 min to dissolve. 30% NaOMe in MeOH (5.26 uL, 0.0284 mmol, 0.2 eq) was added and stirred under Ar for 2 h. A white precipitate formed within 20 min. The precipitate was collected by centrifuge, and then redissolved in H$_2$O. The pH was neutralized with 0.1 N HCl, and the solution was dialyzed (MWCO 3,500 g/mol) against H$_2$O (1 L×2). The solution was then filtered with 0.2 μM syringe filter to remove any insoluble solids. The aqueous solution was lyophilized to obtain 44 mg of P4. $^1$H NMR (500 MHz in D$_2$O) δ: 5.16, 5.07, 4.26, 4.02, 3.95, 3.76, 3.67, 3.53, 3.36, 2.03, 1.86, 0.98, 0.81. IR: 3342, 2934, 1722, 1367, 1232, 1147, 1102, 1019, 802 cm$^{-1}$.

Horseradish Peroxidase Stabilized by P1-P4 at 70° C.

0.15 mg/mL HRP solution was prepared in pH 7.0 10 mM sodium phosphate buffer. Stock solutions of 100 equiv of P1, P2, P3 and P4 and 7500 equiv of trehalose were also prepared in the same buffer. 2 μL aliquots of HRP solution were mixed with 2 μL aliquots of each polymer and trehalose solution to give final concentration of 75 μg/mL HRP or with only buffer. Samples were heated under 70° C. for 30 min and control was stored in 4° C. until the activity assay was performed. The assay was repeated 6 times following the know procedure with tetramethylbenzemidine (TMB).

Glucose Oxidase Stabilized by P1-P4 at 50° C.

0.2 mg/mL GOX solution was prepared in pH 7.0 10 mM sodium phosphate buffer. Stock solution of 100 equiv of P1, P2, P3 and P4 and 7500 equiv of trehalose were also prepared in pH 7.0 10 mM sodium phosphate buffer. 2 μL aliquots of GOX solution were mixed with 2 μL aliquots of each polymer and trehalose solution or buffer only to give the final concentration of 0.1 mg/mL GOX. Samples were heated under 50° C. for 30 min and control was stored at 4° C. until the activity assay was performed. Activity was measured using Amplex® Red Glucose/Glucose Oxidase Assay kit following the product manual procedures.

Recombinant Human Insulin Stabilized by P1-P3 at 90° C.

Insulin was dissolved in pH 7.4 D-PBS buffer (1 mg/mL). The samples were prepared by adding 10 equiv of P1, P2, and P3 or 750 equiv of trehalose into the insulin solution. The control was stored in 4° C. until characterization with native gel. Other samples with polymers or trehalose were heated as 90° C. for 1 h and ran through the native gel.

Fi-Galactosidase Stabilized by P1-P3 to Lyophilization.

0.4 mg/mL P3-Gal solution was prepared in pH 7.0 10 mM sodium phosphate buffer. 50 μL aliquots of β-Gal solution were mixed with 150 μL of buffer or 150 μL of polymer (100 equiv) or trehalose (7500 equiv) in H$_2$O to result 0.1 mg/mL protein solution. Aliquots of each sample were frozen by immersion in liquid nitrogen before lyophilization. The samples were lyophilized for 12 h for one cycle under 1 mbar. After each cycle 200 μL of H$_2$O was added and the lyophilization repeated for 3 cycles and 4 cycles. The control was stored in 4° C. until the activity assay was performed. The assay includes 6 repeats by reacting with o-nitrophenyl-β-D-galactoside (ONPG).

Cytotoxicity Assay of P1-P3.

The cytotoxicity of the trehalose glycopolymers was evaluated using the LIVE/DEAD® viability/cytotoxicity assay (Invitrogen) with NIH 3T3, RAW 264.7, HDF, and HUVEC cells. NIH 3T3 and RAW 264.7 cells were cultured in DMEM (Gibco) supplemented with 10% fetal bovine serum (FBS) and 1% penicillin-streptomycin. HDF cells were cultured in fibroblast growth medium (Promocell) containing 2% fetal calf serum (FCS), 1 ng/mL basic fibroblast growth factor (bFGF), 5 µg/mL insulin, and 1% penicillin-streptomycin. HUVECs were cultured in endothelial cell growth medium (Promocell) containing 2% FCS with supplements recommended by the supplier. The cells were seeded in 48-well plates (BD Falcon) at a density of $5\times10^3$ cells per well. After 24 h, the culture media were replaced with 200 µL of the working medium containing known polymer concentrations of 0.1, 0.5, and 1 mg/mL. After incubation for 48 hours, the cells were gently washed twice with pre-warmed D-PBS, and stained with the LIVE/DEAD reagent (2 µM calcein AM and 4 µM ethidium homodimer-1). Fluorescent images of each well were captured on an Axiovert 200 microscope with an AxioCam MRm camera and FluoArc mercury lamp. The number of live and dead cells was counted, and percent cell viability was calculated by dividing the number of live cells by the total number of cells. All experiments were conducted with four repetitions and averaged. For all the assays in the report, statistics to determine significance were calculated based on an independent two samples Students t-test with non-equal variance.

Example 7: Trehalose Glycopolymers for Stabilization of siRNA

Figure 37:
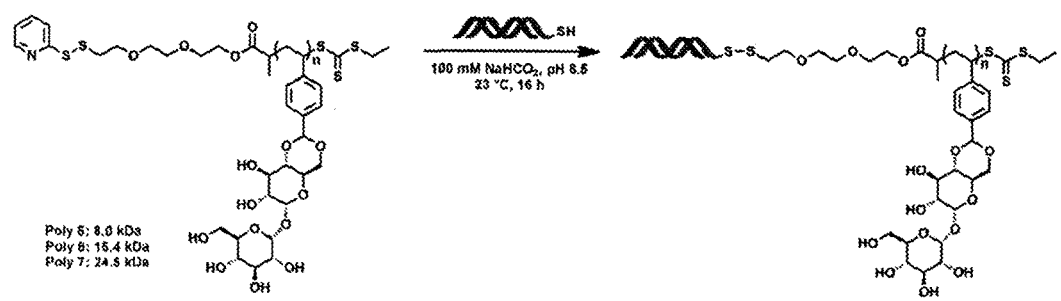
FIG. 37 shows Scheme 15. Conjugation of siRNA to Poly 5, Poly 6, and Poly 7.

Thiol modified ds-siRNA was deprotected with DTT to provide a free thiol on the 5' end of the sense strand. Three different sizes of pyridyl disulfide end-functionalized trehalose polymer were then conjugated to siRNA through disulfide exchange (FIG. 37 Scheme 15). The three polymers are Poly 5, Poly 6, and Poly 7. On a TBE PAGE gel, siRNA and the conjugates were analyzed under both reducing and non-reducing conditions (data not shown). Under reducing conditions, the disulfide linkages of the polymers were cleaved, so only the bands representing free siRNA was seen. However, under non-reducing conditions, the higher molecular weight smear of the conjugates was observed. The conjugation efficiencies of the polymers' reaction with siRNA to form conjugates A, B, and C were calculated as 85%, 76%, and 73%, respectively.

Figure 33:
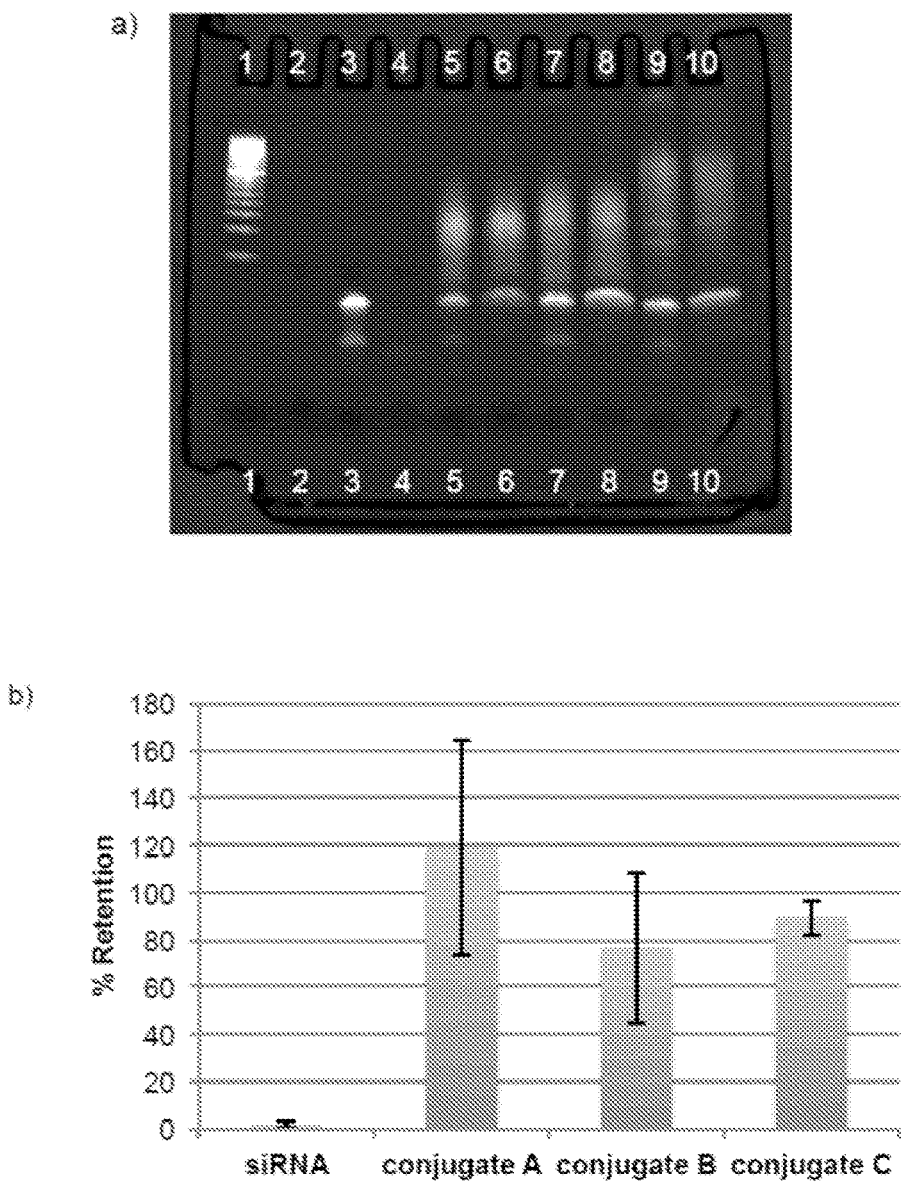
FIGS. 33a and b are a set of graphs showing the stability effect of trehalose polymer Poly 5, Poly 6, Poly 7 and Poly 8 to siRNA. a) PAGE of the effect of RNase ONE towards naked ds-siRNA and conjugate A, B, and C. Lane 1: DNA ladder; lane 2: RNase ONE; lane 3: ds-siRNA; lane 4: ds-siRNA with RNase ONE; lane 5: conjugate A (siRNA-Poly 5); lane 6: conjugate A (siRNA-Poly 5) with RNase ONE; lane 7: conjugate B (siRNA-Poly 6); lane 8: conjugate B (siRNA-Poly 6) with RNase ONE; lane 9: conjugate C (siRNA-Poly 7); lane 10: conjugate C (siRNA-Poly 8) with RNase ONE. b) Quantification of the retention conjugates after RNase ONE treatment. Data shown are repeated 3 times.

RNase ONE™ Ribonuclease degrades RNA readily and the stability of siRNA with trehalose polymer was tested to determine protection against nuclease degradation. After one hour of incubation with RNase ONE at 37° C., naked siRNA was nearly entirely degraded by gel (FIG. 33). However, conjugates A-C all showed high stability towards RNase ONE degradation. To confirm whether conjugation is essential to the stabilization effect, the effect of adding trehalose polymer Poly 5 or adding trehalose to naked siRNA were also compared (data not shown). From lane 8 and 10 of the gel, it is observed that polymer Poly 5 and trehalose do protect siRNA better than having no additives (lane 4). However, there was still degradation/cleavage observed. Conjugation of the polymer is superior to just adding it to the siRNA.

Figure 34:
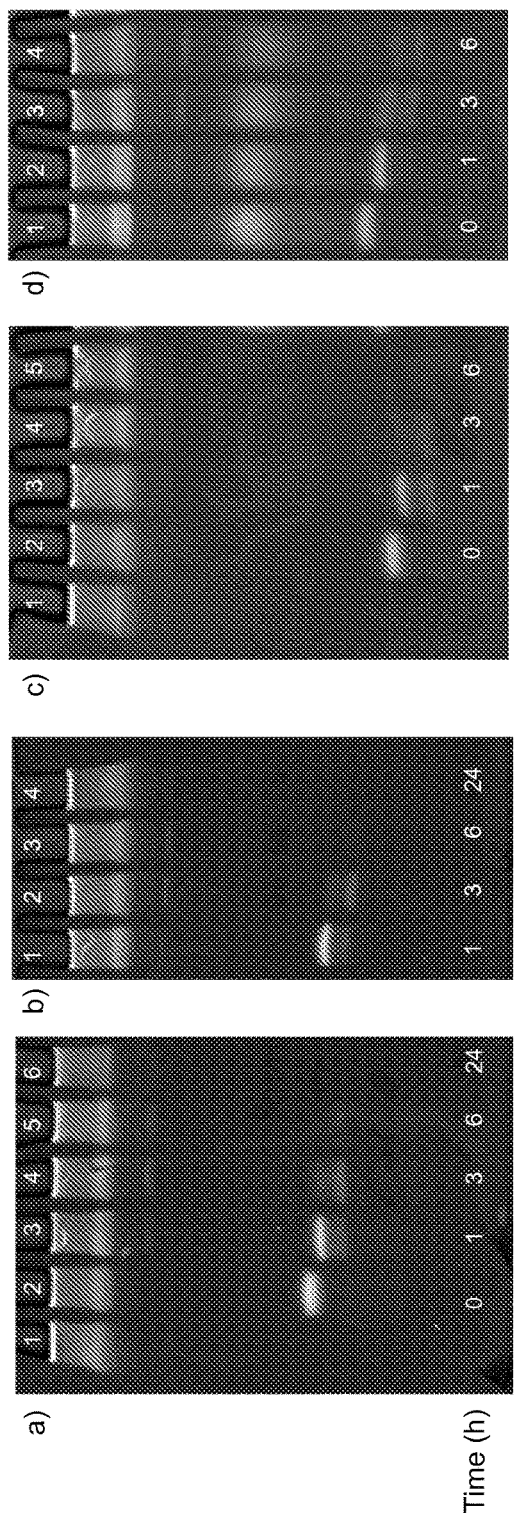
FIG. 34 is a set of graphs showing PAGE of the effect of 80% Calf Bovine Serum (CBS) towards: a) naked ds-siRNA. Lane 1: 80% CBS; lane 2: 0 h; lane 3: 1 h; lane 4: 3 h; lane 5: 6 h; lane 6: 24 h; b) ds-siRNA with addition of 825 eq of trehalose. Lane 1: 1 h; lane 2: 3 h; lane 3: 6 h; lane 4: 24 h; c) ds-siRNA with addition of 50 eq of trehalose polymer Poly 5. Lane 1: 80% CBS; lane 2: 0 h; lane 3: 1 h; lane 4: 3 h; lane 5: 6 h; d) Conjugate A. Lane 1: 0 h; lane 2: 1 h; lane 3: 3 h; lane 4: 6 h.

The stability of siRNA with no additive, trehalose as an additive, trehalose polymer Poly 5 as an additive, and conjugate A in 80% calf bovine serum (CBS) were tested. The degradation was observed by taking time points at 0, 1, 3, and 6 (and 24) hours (FIG. 34). From FIG. 34 a)-c), it was observed that the addition of trehalose or trehalose polymer Poly 5 did not show significant difference in the degradation of siRNA over 6 hours. On the other hand, after 6 hours of incubation in 80% CBS at 37° C., conjugate A was still clearly observable with ~63% retention. In conclusion, the conjugation of trehalose polymers to siRNA effectively increases its stability towards nucleases and serum conditions.

Material and Synthesis

Conjugation of siRNA to Pyridyl Disulfide End-Functionalized Trehalose Polymer Poly 5-7.

30 µl of a 0.0383 mM solution of double stranded (ds)-siRNA was mixed with 5 µl of 200 mM dithiothreitol (DTT) solution and kept for 3 h at 24° C. To remove unreacted DTT, ds-siRNA was precipitated using ethanol. The siRNA pellet was completely resuspended in 30 µL of Poly 5, 6, 7 solution (50 eq in 100 mM sodium bicarbonate buffer at pH 8.5). The reaction mixture was left at 23° C. for 20 h. The conjugates were also treated with DTT to confirm that the covalent conjugation of siRNA with polymers could be reversed under physiologically relevant conditions. Conjugate reaction mixtures (0.03 nmol siRNA, 5 µL) in water was incubated with DTT (10 nmol, 1 µL in water) for 1 h at 23° C. Reduced and non-reduced conjugates were then analyzed by 15% Tris Borate EDTA (TBE) polyacrylamide gel electrophoresis (PAGE) at a constant voltage of 200 V for 40 minutes using 1×TBE buffer (pH 8.0). ds-siRNA was stained by incubating the gel in 1×SYBR-Safe nucleic acid dye/TBE buffer. Conjugation efficiency was quantified using the Quanti-One program (BioRad).

RNase stability test. Samples (0.07 nmol siRNA, 4 µL) was mixed with nuclease-free water (or 50 eq Poly 5/825 eq trehalose in water, data not shown) to a final volume of 8 µL. RNase ONE ribonuclease (1 µL, 1 unit, in reaction buffer: 100 mM Tris HCl, pH7.5, 50 nM EDTA, 2 M sodium acetate) was added to each sample and the samples were incubated at 37° C. for up to 60 minutes. Nuclease reactions were terminated by the addition of SDS solution (1 µL from 1% solution in water). The samples were analyzed by PAGE using 15% TBE-Urea gel at a constant voltage of 200 V for 40 min using 1×TBE buffer (pH 8.0). The gel was stained by incubating in 1×SYBR-Safe nucleic acid dye/TBE buffer for 30 min. Percentage retention of siRNA or conjugates were determined by taking the proportion of the band intensity and were normalized to the siRNA or conjugate band intensity before RNase ONE treatment.

Serum Stability Test.

The stabilities of siRNA with no additive, trehalose as an additive, trehalose polymer Poly 5 as an additive, and conjugate A were individually tested in 80% Calf Bovine Serum (CBS). In a typical experiment, the samples (0.1 nmol siRNA, 5 µL) were incubated in 80 v/v % FBS with a total volume of 50 µL at 37° C. for up to 24 hours. During the incubation period, aliquots (10 µL) were taken at predetermined time points and immediately froze at −80° C. until further use. Then, all samples were analyzed together using gel electrophoresis with 15% TBE-Urea ready gel, at a constant voltage of 200 V for 45 minutes using 1×TBE running buffer (pH 8.0). Percent degradation at each time point were determined by taking the proportion of the siRNA band intensity at each time point to the siRNA band intensity at 0 hour.

It is envisioned that the disclosed method of stabilizing biomolecules may be combined with other current approaches used for stabilizing biomolecules, such as, for example, chemical modification, protein engineering (e.g. PEGylation, addition of polymeric sucrose and/or dextran, methoxypolyethlene glycol, poly-carboxybetaine, and/or poly-stryrene sulfonate, etc.), protein cross-linkage (e.g. production of cross-linked enzymes crystals or CLEC's, etc.), catalyst immobilization, engineered fusion-proteins and other chemical or biological methodologies. Combining stabilization techniques may enhance pharmacological properties and significantly increase biomolecule's stability to temperature, desiccation, light, storage, exposure to enzymes, endo- and exo-nucleases and pH variation.

REFERENCES

1. Abuchowski, A., Mccoy, J. R., Palczuk, N. C., Vanes, T. & Davis, F. F. Effect of Covalent Attachment of Polyethylene-Glycol on Immunogenicity and Circulating Life of Bovine Liver Catalase. Journal of Biological Chemistry 252, 3582-3586 (1977).
2. Aga, H.; Shibuya, T.; Fukuda, S.; Miyake, T. Reduction inhibitory agent for active-oxygen eliminating activity. U.S. Ser. No. 07/186,824, Mar. 6 2007.
3. Alconcel, S. N. S., Baas, A. S. & Maynard, H. D. FDA-approved poly(ethylene glycol)-protein conjugate drugs. Polymer Chemistry 2, 1442-1448 (2011).
4. Andya, J.; Cleland, J. L.; Hsu, C. C.; Lam, X. M.; Overcashier, D. E.; Shire, S. J.; Yang, J. Y.-F.; Wu, S. S.-Y. Protein formulation. U.S. Ser. No. 07/682,609, Mar. 23 2010.
5. Bachmann, F.; Lohmann, D.; Chabrecek, P. Unsaturated carbohydrate derivatives polymers thereof and their use. U.S. Pat. No. 5,693,768, Dec. 2, 1997.
6. Bays, E., Tao, L., Chang, C. W. & Maynard, H. D. Synthesis of Semitelechelic Maleimide Poly(PEGA) for Protein Conjugation by RAFT Polymerization. Biomacromolecules 10, 1777-1781 (2009).
7. Beattie, G. M.; Crowe, J. H.; Tablin, F.; Hayek, A. Cryopreservation of human adult and fetal pancreatic cells and human platelets. U.S. Pat. No. 5,827,741, Oct. 27, 1998.
8. Bollin, E. J.; Fletcher, M. G. TREHALOSE AS STABILIZER AND TABLETING EXCIPIENT U.S. Pat. No. 4,762,857. Aug. 9 1988. U.S. Pat. No. 4,762,857, 1988.
9. Brockbank, K. G. M.; Campbell, L. H.; Ratcliff, K. M.; Sarver, K. A. Method for treatment of cellular materials with sugars prior to preservation. U.S. Ser. No. 08/017, 311, Sep. 13 2011.
10. Carpenter, J. F.; Hand, S. C.; Crowe, J. H.; Crowe, L. M. CRYOGENIC PROTECTANT FOR PROTEINS U.S. Pat. No. 4,806,343. Feb. 21 1989. U.S. Pat. No. 4,806, 343, 1989.
11. Chaen, H.; Mitsuhashi, M.; Miyake, T. Method and composition for improving the aftertaste of sucrose. U.S. Pat. No. 6,432,470, Aug. 13, 2002.
12. Chaen, H.; Oku, K.; Miyake, T. Method for inhibiting trimethylamine formation. U.S. Pat. No. 6,576,281, Jun. 10, 2003.
13. Chaen, H.; Oku, K.; Uchida, Y.; Miyake, T. Method for inhibiting the formation of volatile aldehydes including their related compounds and/or the decomposition of fatty acids including their related compounds, and uses thereof. U.S. Pat. No. 6,268,353, Jul. 31, 2001.
14. Chi, E. Y., Krishnan, S., Randolph, T. W. & Carpenter, J. F. Physical stability of proteins in aqueous solution: Mechanism and driving forces in nonnative protein aggregation. Pharmaceutical Research 20, 1325-1336 (2003).
15. Chiefari, J.; Cong, Y. K.; Ercole, F.; Krstina, J.; J., J.; Le, T. P. T.; Mayadunne, R. T. A.; Meijs, G. F.; Moad, C. L.; Moad, G.; Rizzardo, E.; Thang, S. H., Macromolecules 1998, 31, 5559-5562.
16. Cleland, J. L.; Jones, A. J. S. Excipient stabilization of polypeptides treated with organic solvents. U.S. Pat. No. 5,804,557, Sep. 8, 1998.
17. Cohen, S.; Yoshioka, T.; Lucarelli, M.; Hwang, L. H.; Langer, R., Controlled Delivery Systems for Proteins Based on Poly(Lactic Glycolic Acid) Microspheres. Pharmaceutical Research 1991, 8, (6), 713-720.
18. Collis, M. P.; Szczepanik, S. H. Vehicle for delivery of particles to a sample. U.S. Pat. No. 5,840,878, Nov. 24, 1998.
19. Collis, Matthew P, Szczepanik, Stephen H., Vehicle for delivery of particles to a sample U.S. Pat. No. 5,962,310, Oct. 5, 1999.
20. Cooper, J. M.; Tian, W. Edible compositions containing trehalose. U.S. Pat. No. 6,620,791, Sep. 16, 2003.
21. Crowe, J. H.; Crowe, L. M.; Tablin, F.; Wolkers, W. F.; Tsvetkova, N. M.; Oliver, A. F. Erythrocytic cells and method for preserving cells. U.S. Pat. No. 6,770,478, Aug. 3, 2004.
22. Crowe, L. M., Reid, D. S. & Crowe, J. H. Is trehalose special for preserving dry biomaterials? Biophys. J. 71, 2087-2093 (1996).
23. DePablo, J.; Miller, D.; Conrad, P.; Corti, H. Preservation and storage medium for biological materials. U.S. Ser. No. 06/919,172, Jul. 19 2005.
24. DePablo, J.; Nie, Y.; Palecek, S. P. Lyophilization of human platelets. U.S. Ser. No. 07/169,606, Jan. 30 2007.
25. Fukuda, S.; Ario, T.; Miyake, T. Drugs against articular failure. U.S. Ser. No. 07/214,667, May 8 2007.
26. Fukuda, S.; Miyake, T. Agent for improving the blood circulation. U.S. Pat. No. 5,981,498, Nov. 9, 1999.
27. Gribbon, E. M.; Martyn, G. P.; Colaco, C. A. L. S. Tablet dosage form of clavulanic acid and amoxycillin comprising a trehalose excipient. U.S. Pat. No. 6,194,001, Feb. 27, 2001.
28. Grimshaw, M. N.; Barbieri, D. J.; Vizzini, L. M.; Marsh, S. F. Rapidly disintegrable tablets. U.S. Ser. No. 07/425, 341, Sep. 16, 2008.
29. Hand, S. C.; Menze, M. A. Preservation of eukaryotic cells using reversible pore formation. U.S. Ser. No. 07/314,755, Jan. 1, 2008.
30. Harris, J. M. & Chess, R. B. Effect of pegylation on pharmaceuticals. Nat Rev Drug Discov 2, 214-221 (2003).
31. Hengherr, S., Heyer, A. G., Kohler, H. R. & Schill, R. O. Trehalose and anhydrobiosis in tardigrades—evidence for divergence in responses to dehydration. Febs Journal 275, 281-288 (2008).
32. Jain, N. K. & Roy, I. Effect of trehalose on protein structure. Protein Science 18, 24-36 (2009).
33. Kajiyama, A.; Tamura, T.; Mizumoto, T.; Kawai, H.; Takahashi, T. Quick disintegrating tablet in buccal cavity and manufacturing method thereof. U.S. Ser. No. 07/074, 428, Jul. 11 2006.
34. Kampinga, J.; Colaco, C. A. L. S. Compositions for use in rehydration and nutrition during athletic exercise and methods of making same. U.S. Pat. No. 6,455,511, Sep. 24, 2002.
35. Kampinga, J.; Colaco, C., Compositions for use in rehydration and nutrition during athletic exercise and methods of making same, U.S. Pat. No. 6,596,702, Jul. 22, 2003.
36. Katagiri, N.; Iritani, S.; Miyake, T. Hard candy with a relatively-high moisture and hardness, and process of the same. U.S. Pat. No. 6,455,096, Sep. 24, 2002.
37. Kaushik, J. K. & Bhat, R. Why is trehalose an exceptional protein stabilizer? An analysis of the thermal sta- 37. bility of proteins in the presence of the compatible osmolyte trehalose. Journal of Biological Chemistry 278, 26458-26465 (2003).
38. Keefe, A. J.; Jiang, S., Poly(zwitterionic)protein conjugates offer increased stability without sacrificing binding affinity or bioactivity. Nature Chemistry 2012, 4, 59-63.
39. Kitagawa, M.; Chalermisrachai, P.; Fan, H.; Tokiwa, Y., Chemoenzymatic Synthesis of Biodegradable Polymers Containing Glucobiose Branches. Macromolecular Symposium 1999, 144, 247-256.
40. Kowata, T.; Sato, M.; Shimomura, T.; Yamashita, M. Inhibitory agent for protein denaturation, kneaded meat with suppressed freezing-denaturation, process thereof, and process of fish and meat paste products. U.S. Pat. No. 6,641,853, Nov. 4, 2003.
41. Kurita, K.; Hirakawa, N.; Morinaga, H.; Iwakura, Y., Synthetic-Polymers Containing Sugar Residues 0.6. Novel Polyurethanes by Direct Addition Polymerization of Alpha,Alpha-Trehalose with Diisocyanates. Makromolekulare Chemie-Macromolecular Chemistry and Physics 1979, 180, (11), 2769-2773.
42. Kurita, K.; Masuda, N.; Aibe, S.; Murakami, K.; Ishii, S.; Nishimura, S. I., SYNTHETIC CARBOHYDRATE POLYMERS CONTAINING TREHALOSE RESIDUES IN THE MAIN-CHAIN—PREPARATION AND CHARACTERISTIC PROPERTIES. Macromolecules 1994, 27, (26), 7544-7549.
43. Lam, X. M.; Oeswein, J. Q.; Ongpipattanakul, B.; Shahrokh, Z.; Wang, S. X.; Weissburg, R. P.; Wong, R. L. Antibody formulation. U.S. Ser. No. 06/991,790, Jan. 31 2006.
44. Le, T.; Moad, G.; Rizzardo, E.; Thang, S. H. 1998.
45. Levine, F. Vacuum-mediated desiccation protection of cells. U.S. Pat. No. 6,528,309, Mar. 4, 2003, 2003.
46. Lyczak, J. B.; Morrison, S. L., Biological and Pharmacokinetic Properties of a Novel Immunoglobulin-Cd4 Fusion Protein. Archives of Virology 1994, 139, (1-2), 189-196.
47. Maity, H., O'Dell, C., Srivastava, A. & Goldstein, J. Effects of Arginine on Photostability and Thermal Stability of IgG1 Monoclonal Antibodies. Curr. Pharm. Biotechnol. 10, 761-766 (2009).
48. Mandai, T.; Shibuya, T.; Sugimoto, T.; Miyake, T. Trehalose composition for prolonging product shelf life. U.S. Pat. No. 6,005,100, Dec. 21, 1999.
49. Mateczun, A. J.; Peruski, L. F., Jr. Viable dried bacteria produced by drying in the presence of trehalose and divalent cation. U.S. Pat. No. 6,610,531, Aug. 26, 2003.
50. Mateo, C. et al. Removal of amphipathic epitopes from genetically engineered antibodies: Production of modified immunoglobulins with reduced immunogenicity. Hybridoma 19, 463-471 (2000).
51. Matsuo, T.; Kurimoto, M.; Yamauchi, H. Pharmaceutical composition for ophthalmic use. U.S. Pat. No. 6,555,526, Apr. 29, 2003.
52. Mizumoto, T.; Masuda, Y.; Kajiyama, A.; Yanagisawa, M.; Nyshadham, J. R. Tablets quickly disintegrating in the oral cavity and process for producing the same. U.S. Pat. No. 6,589,554, Jul. 8, 2003.
53. Ohkouchi, K.; Koyama, H. Quickly disintegrating solid preparations. U.S. Pat. No. 6,740,339, May 25, 2004.
54. Ohtake, S. & Wang, Y. J. Trehalose: Current Use and Future Applications. Journal of Pharmaceutical Sciences 100, 2020-2053 (2011).
55. Okada, M.; Ikeda, Y.; Ono, K.; Kurazumi, T.; Kasai, S.; Imamori, K. Quickly soluble solid preparations. U.S. Pat. No. 6,455,053, Sep. 24, 2002.
56. Oku, K.; Kubota, M.; Fukuda, S.; Miyake, T. Composition for inhibiting body odor and uses thereof. U.S. Pat. No. 6,497,862, Dec. 24, 2002.
57. Oobatake, M. & Ooi, T. HYDRATION AND HEAT-STABILITY EFFECTS ON PROTEIN UNFOLDING. Prog. Biophys. Mol. Biol. 59, 237-284 (1993).
58. Park, O. J.; Kim, D. Y.; Dordick, J. S., Enzyme-catalyzed synthesis of sugar-containing monomers and linear polymers. Biotechnology and Bioengineering 2000, 70, (2), 208-216.
59. Roberts, M. J., Bentley, M. D. & Harris, J. M. Chemistry for peptide and protein PEGylation. Adv Drug Deliver Rev 54, 459-476 (2002).
60. Roser, B. J.; Blair, J. Rapidly soluble oral solid dosage forms, methods of making same, and compositions thereof. U.S. Pat. No. 5,762,961, Jun. 9, 1998.
61. Roser, B. J.; Blair, J.; Colaco, C.; Hatley, R. H. M. Oral solid dosage forms, methods of making same and compositions thereof. U.S. Pat. No. 5,958,455, Sep. 28, 1999.
62. Roser, B. J.; Kampinga, J.; Colaco, C.; Blair, J. Solid dose delivery vehicle and methods of making same. U.S. Ser. No. 07/785,631, Aug. 31, 2010.
63. Sakurai, M. Biological Functions of Trehalose as a Substitute for Water. Water and Biomolecules: PHYSICAL CHEMISTRY OF LIFE PHENOMENA, 219-240 (2009).
64. Seki, K. Method for preserving mammalian organs. U.S. Pat. No. 6,475,716, Nov. 5, 2002.
65. Shinoda, T.; Maeda, A.; Itou, N.; Mizumoto, T.; Yamazaki, S.; Takaishi, Y. Composition comprises sustained-release fine particles and manufacturing method thereof. U.S. Ser. No. 07/575,762, Aug. 18 2009.
66. Srinivasachari, S.; Liu, Y. M.; Prevette, L. E.; Reineke, T. M., Effects of trehalose click polymer length on pDNA complex stability and delivery efficacy. Biomaterials 2007, 28, (18), 2885-2898.
67. Srinivasachari, S.; Liu, Y. M.; Zhang, G. D.; Prevette, L.; Reineke, T. M., Trehalose click polymers inhibit nanoparticle aggregation and promote pDNA delivery in serum. Journal of the American Chemical Society 2006, 128, (25), 8176-8184.
68. Sundaramurthi, P., Shalaev, E. & Suryanarayanan, R. "pH Swing" in Frozen Solutions-Consequence of Sequential Crystallization of Buffer Components. Journal of Physical Chemistry Letters 1, 265-268 (2010).
69. Syed, S., Schuyler, P. D., Kulczycky, M. & Sheffield, W. P. Potent antithrombin activity and delayed clearance from the circulation characterize recombinant hirudin genetically fused to albumin. Blood 89, 3243-3252 (1997).
70. Syed, S.; Schuyler, P. D.; Kulczycky, M.; Sheffield, W. P., Potent antithrombin activity and delayed clearance from the circulation characterize recombinant hirudin genetically fused to albumin. Blood 1997, 89, (9), 3243-3252.
71. Takeuchi, Yasuo; Shibuya, Takashi, Miyake, Toshio, U.S. Pat. No. 6,254,912, Jul. 3, 2001.
72. Teramoto, N.; Arai, Y.; Shibasaki, Y.; Shibata, M., A facile synthesis of a novel polyacetal containing trehalose residue in the main chain. Carbohydrate Polymers 2004, 56, (1), 1-6.
73. Teramoto, N.; Arai, Y.; Shibata, M., Thermo-reversible Diels-Alder polymerization of difurfurylidene trehalose and bismaleimides. Carbohydrate Polymers 2006, 64, (1), 78-84.

74. Teramoto, N.; Shibata, M., Trehalose-based thermosetting resins. I. Synthesis and thermal properties of trehalose vinylbenzyl ether. Journal of Applied Polymer Science 2004, 91, (1), 46-51.
75. Oku, Kazuyuki; Kubota, Michio; Fukuda, Shigeharu; Miyake, Toshio; Radical reaction inhibitors, method for inhibition of radical reactions, and use thereof, U.S. 2005-0267067, Dec. 1, 2005.
76. Uchida, Y.; Iritani, S.; Miyake, T. Method for enhancing the salty-taste and/or delicious-taste of food products. U.S. Pat. No. 6,159,529, Dec. 12, 2000.
77. Wang, W. Lyophilization and development of solid protein pharmaceuticals. International Journal of Pharmaceutics 203, 1-60 (2000).
78. Wang, Y.-C. J.; Yang, B.; Jennings, R. N.; Protter, A. A. Controlled release delivery of peptide or protein. U.S. Pat. No. 6,187,330, Feb. 13, 2001.
79. Wang, Y.-C. J.; Yang, B.; Jennings, R. N.; Protter, A. A. Controlled release delivery of peptide or protein. U.S. Pat. No. 6,187,330, Feb. 13, 2001.
80. Westh, P. & Ramlov, H. Trehalose Accumulation in the Tardigrade Adorybiotus-Coronifer during Anhydrobiosis. Journal of Experimental Zoology 258, 303-311 (1991).
81. Wolfenden, R.; Yuan, Y., Rates of spontaneous cleavage of glucose, fructose, sucrose, and trehalose in water, and the catalytic proficiencies of invertase and trehalas. Journal of the American Chemical Society 2008, 130, (24), 7548-7549
82. Yanagisawa, M.; Mizumoto, T. Bitterness-reduced intrabuccally quick disintegrating tablets and method for reducing bitterness. U.S. Ser. No. 06/998,139, Feb. 14, 2006.
83. Yang, W.; Zhang, L.; Wang, S. L.; White, A. D.; Jiang, S. Y., Functionalizable and ultra stable nanoparticles coated with zwitterionic poly(carboxybetaine) in undiluted blood serum. Biomaterials 2009, 30, (29), 5617-5621.
84. Yoshizane, C.; Nishizaki, Y.; Arai, S.; Kurimoto, M. Agent for anti-osteoporosis. U.S. Pat. No. 6,440,446, Aug. 27, 2002.
85. Sakurai, M., Murata, M., Inoue, Y., Hino, A. & Kobayashi, S. Molecular-dynamics study of aqueous solution of trehalose and maltose: Implication for the biological function of trehalose. Bulletin of the Chemical Society of Japan 70, 847-858 (1997)
86. Ambrosi, M.; Batsanowv, A. S.; Cameron, N. R.; Davis, B. G.; Howard, J. A. K.; Hunter, R. Journal of the Chemical Society—Perkin Transactions 1 2002, 45.
87. Hermanson, G. T. Bioconjugate techniques. Academic Press, Inc., 1250 Sixth Ave., San Diego, Calif. 92101, USA; Academic Press Ltd., 14 Belgrave Square, 24-28 Oval Road, London NW1 7OX, England, U K, 1996
88. Li, R. C.; Boryer, R. M.; Maynard, H. D. Journal of Polymer Science Part a—Polymer Chemistry 2006., 44, 2004.
89. Perrier, S., Takolpuckdee, P. & Mars, C. A. Reversible addition-fragmentation chain transfer polymerization: End group modification for functionalized polymers and chain transfer agent recovery. Macromolecules 38, 2033-2036 (2005)
90. Pikal-Cleland, K. A.; Carpenter, J. F. Journal of Pharmaceutical Sciences 2001, 90, 1255.
91. Reisener, H. J., Perlin, A. S., Ledingham, G. A. & Goldschmid, H. R. FORMATION OF TREHALOSE AND POLYOLS BY WHEAT STEM RUST (*PUCCINIA GRAMINIS TRITICI*) UREDOSPORES. Canadian Journal of Biochemistry and Physiology 40, 1248-& (1962)
92. Steinem, C. et al. Valinomycin-mediated transport of alkali cations through solid supported membranes. Bioelectrochemistry and Bioenergetics 45, 17-26 (1998)
93. Sun, G. R., Cheng, C. & Wooley, K. L. Reversible addition fragmentation chain transfer polymerization of 4-vinylbenzaldehyde. Macromolecules 40, 793-795 (2007)
94. Vazquez-Dorbatt, V.; Maynard, H. D. Biomacromolecules 2006, 7, 2297.
95. Zabransky, J.; Houska, M.; Kalal, J. Makromolekulare Chemie—Macromolecular Chemistry and Physics 1985, 186, 223.
96 Nguyen, T. H.; Kim, S. H.; Wong, D. Y.; Decker, C. G.; Loo, J. A.; Maynard, H. D., "Heparin Mimicking Polymer Conjugate Stabilizes bFGF to Environmental Stressors," Nature Chemistry, 2013, DOI: 10.1038/NCHEM. 1573

We claim:

1. A monomer for use in making a homopolymer or a copolymer for stabilizing a biomolecule, the monomer having the general structure:

$R_1R_2C{=}CR_3R_4$, wherein $R_1$-$R_4$ are independently selected from hydrogen or a side chain comprising at least one carbon atom, and wherein at least one of $R_1$-$R_4$ is -L-trehalose, wherein L is a linking group that links trehalose to the monomer through at least one of the trehalose hydroxyl groups (—OH), wherein L is selected from group consisting of -aryl-$(CH_2)_{n1}$— ($_{n1}$=0-6), —(COO)—$(CH_2)_{n2}$— ($_{n2}$=1-6), —$(CH_2)_{n4}$— ($_{n4}$=0-6), -aryl-(CH)—, —(COO)—$(CH_2)_{n7}$—(CH)— ($_{n7}$=1-6) and —(CO)—, wherein both $R_1$ and $R_2$ are Hs.

2. A homopolymer or co-polymer made from one or more of the monomer of claim 1, the homopolymer or copolymer comprising the general structure:

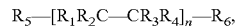

$R_5$—$[R_1R_2C$—$CR_3R_4]_n$—$R_6$, wherein n defines a number of repeat units sufficient to yield a molecular weight of said homopolymer or co-polymer from 4.200 g/mol to 19.000 g/mol, wherein $R_1$-$R_4$ are independently selected from hydrogen or a side chain comprising at least one carbon atom, and wherein at least one of $R_1$-$R_4$ is -L-trehalose, wherein L is a linking group that links trehalose to the monomer through at least one of the trehalose hydroxyl groups (—OH), wherein $R_5$ and $R_6$ are independently selected from the group consisting of -Alkyl, -Alkenyl, -Alkynyl, -aryl, —C(CN)(Alkyl)$_2$, —S$_2$C—S-Alkyl, —C(CO)(Alkyl)-(OCH$_2$CH$_2$)$_{n5}$—COO—CH$_2$CH$_2$—CO-Alkyl ($_{n5}$=1-10), and biomolecules, and wherein L is selected from group consisting of -aryl-$(CH_2)_{n1}$— ($_{n1}$=0-6), —(COO)—$(CH_2)_{n6}$— ($_{n2}$=0-6), —(CONH)—$(CH_2)_{n3}$— ($_{n3}$—0-5), —$(CH_2)_{n4}$— ($_{n4}$=0-6), -aryl-(CH)—, —(COO)—$(CH_2)_{n7}$—(CH)— ($_{n7}$=1-6) and —(CO)—.

3. The homopolymer or copolymer of claim 2, wherein the biomolecule is selected from the group consisting of proteins, enzymes, antibodies, DNAs, RNAs, and siRNAs.

4. The homopolymer or copolymer of claim 2, wherein the side chain -L-trehalose has a structure selected from the group consisting of:

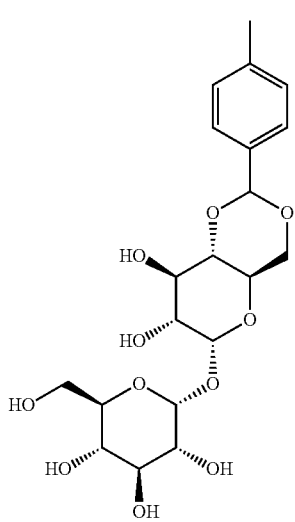

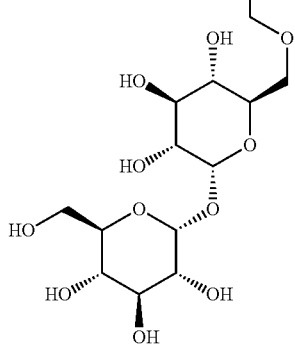

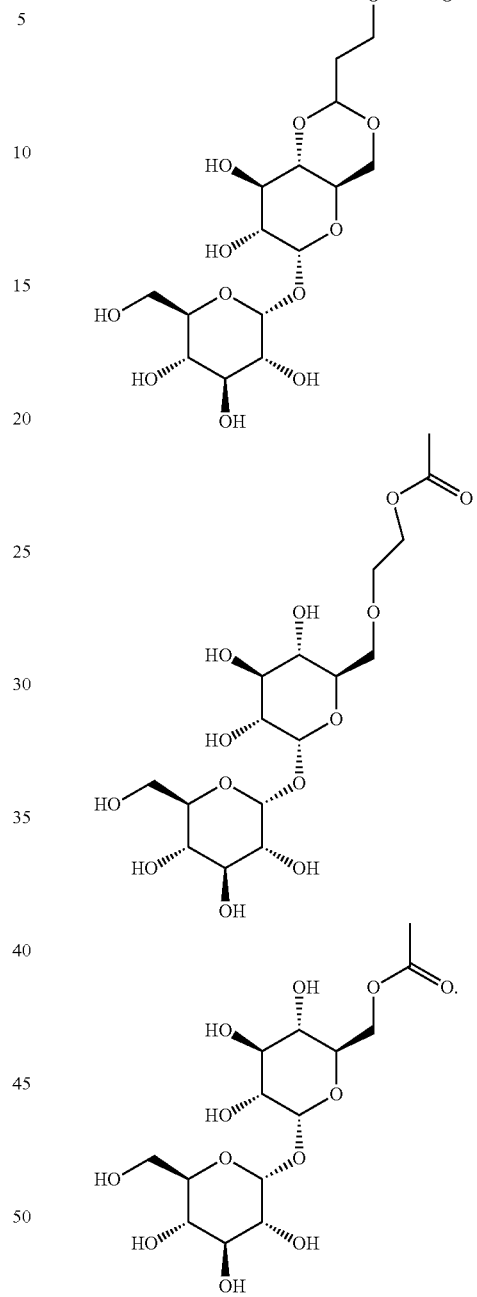

5. The homopolymer or co-polymer of claim 2, wherein any of $R_1$-$R_4$ that is not -L-trehalose is either hydrogen or an alkyl group.

6. The homopolymer or copolymer of claim 5, wherein the alkyl group is a methyl group.

7. The homopolymer or copolymer of claim 2, wherein one of $R_1$-$R_4$ is an alkyl group and two of $R_1$-$R_4$ are hydrogens.

8. The homopolymer or copolymer of claim 7, wherein the alkyl group is a methyl group.

9. The homopolymer or co-polymer of claim 8, having the structure:

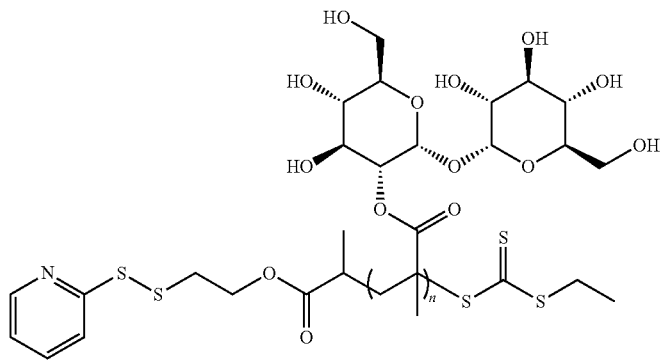
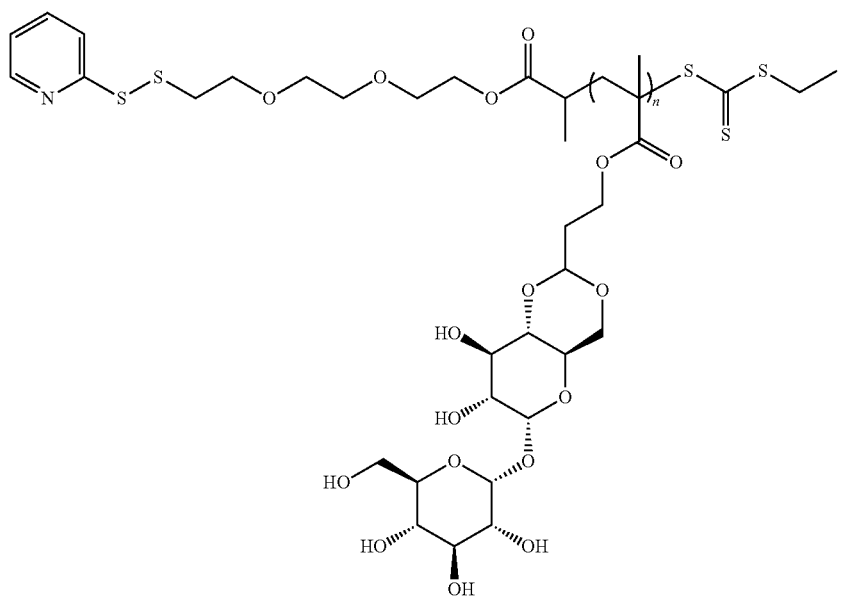
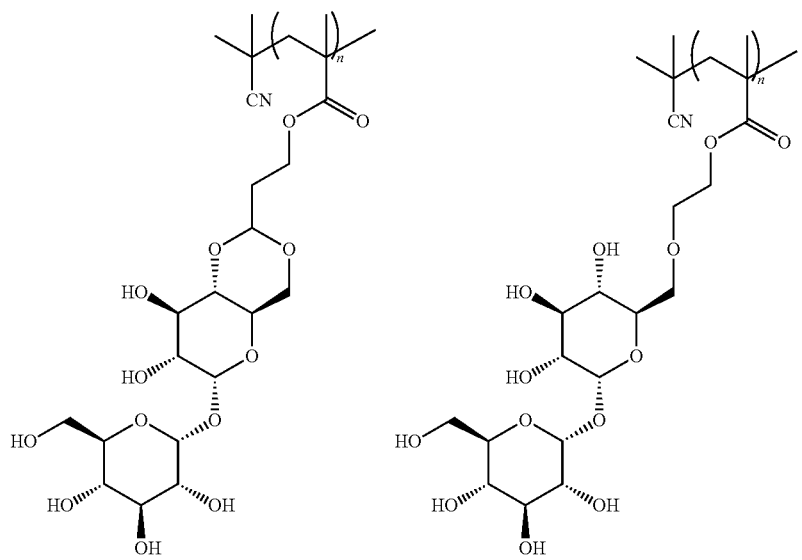

-continued
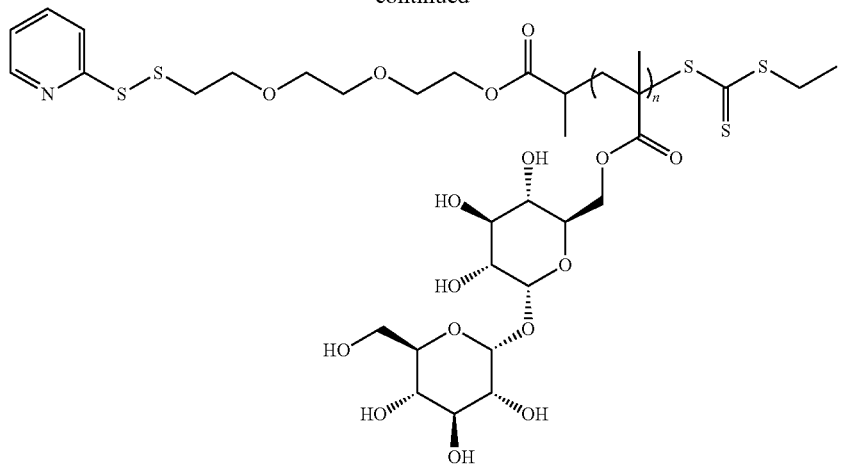
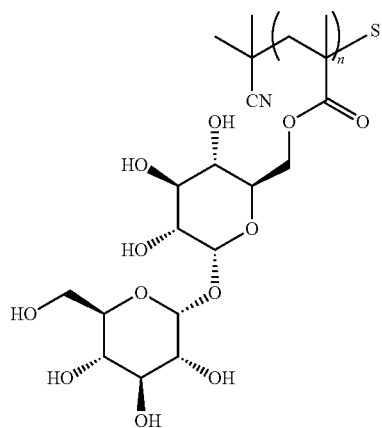
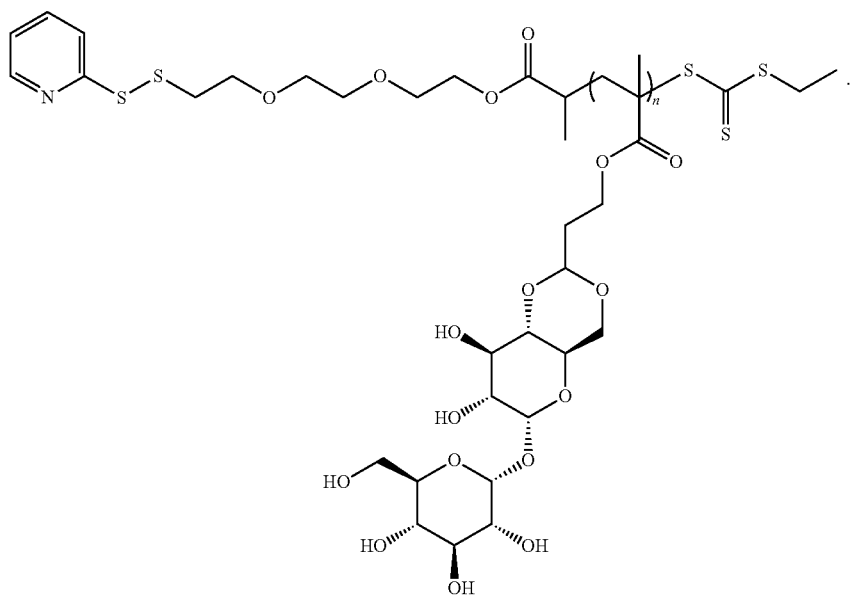
10. The homopolymer or copolymer of claim 2, wherein three of $R_1$-$R_4$ are hydrogens.
11. The homopolymer or co-polymer of claim 10, having the structure selected from the group consisting of:

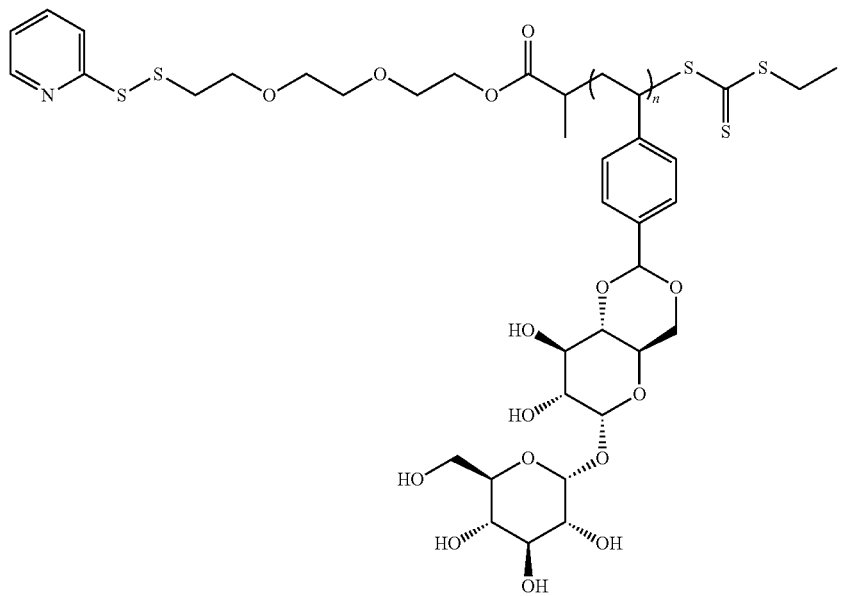
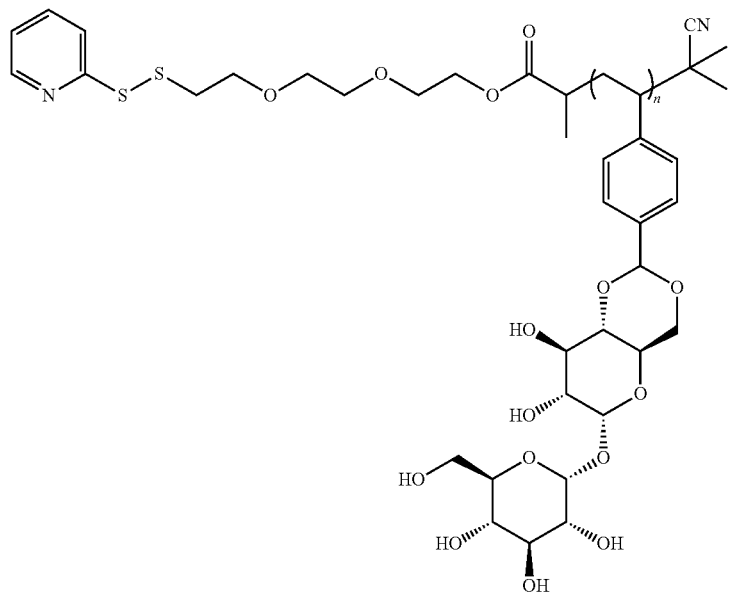

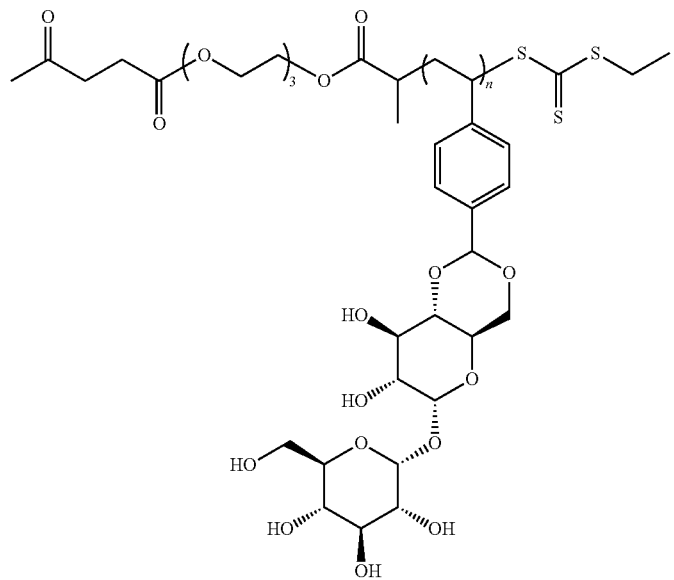
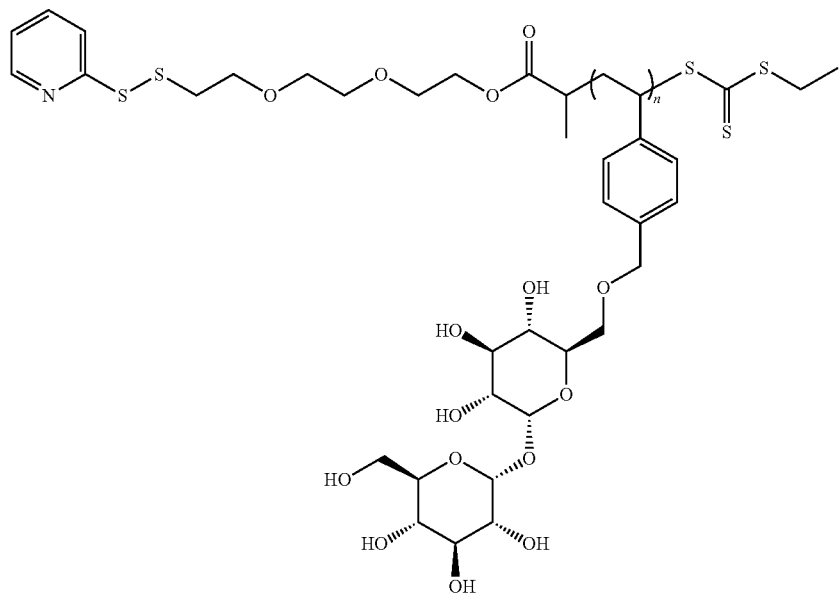

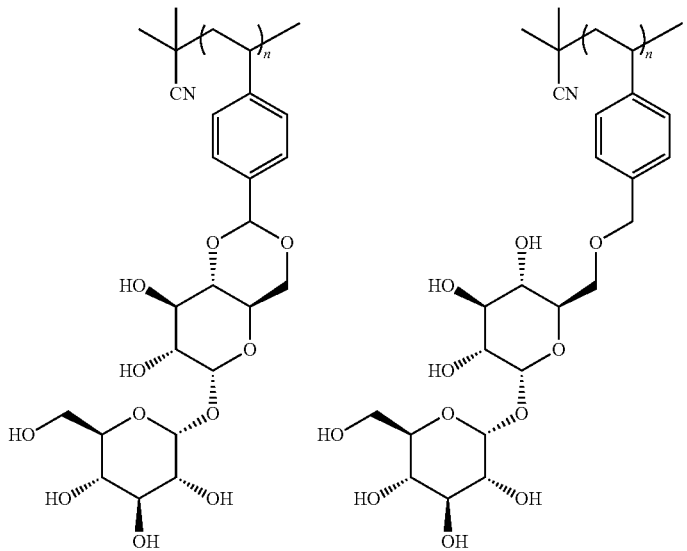

12. A method of synthesizing a homopolymer or copolymer for stabilizing a biomolecule, the method comprising the steps of:
(a) incorporating a side chain comprising a trehalose molecule into a polymerizable monomer, wherein said trehalose molecule optionally comprises protecting groups;
(b) polymerizing the resulting monomer to obtain a polymer: and
(c) optionally deprotecting said trehalose molecule in said polymer, to obtain a homopolymer or co-polymer according to claim 2.

13. The method of claim 12, wherein the homopolymer or copolymer is generated through chemical synthesis.

14. The method of claim 13, wherein the polymerizable monomer is selected from the group consisting of a styrene monomer, an acrylate monomer, a methacrylate monomer, an acrylamide monomer, a methacrylamide monomer, a vinyl monomer, a norborenyl monomer, and a strained cycle alkene monomer.

15. The method of claim 12, wherein the step of polymerizing the resulting monomer to obtain a homopolymer or copolymer is performed by any one of, but not limited to the following techniques; reversible addition-fragmentation (RAFT) polymerization, atom transfer radical polymerization (ATRP), nitroxide mediated polymerization (NMP), cyanoxyl-mediated free radical polymerization, conventional radical polymerization, or ring opening polymerization (ROMP).

16. The method of claim 13, wherein one or more of the hydroxyl groups of the trehalose are protected by the formation of an acetal or an ether.

17. A method of stabilizing a biomolecule comprising the step of conjugating the biomolecule with a homopolymer or copolymer according to claim 2.

18. The method of claim 17, wherein the biomolecule is covalently conjugated to the homopolymer or copolymer backbone.

19. The method of claim 18, wherein the biomolecule is conjugated to the homopolymer or copolymer backbone through a biomolecule reactive group attached to one or both termini of the homopolymer or copolymer backbone.

20. The method of claim 19, wherein the biomolecule reactive group is a thiol reactive group.

21. The method of claim 17, wherein the biomolecule is selected from the group consisting of proteins, enzymes, antibodies, DNAs, RNAs and siRNAs.

22. A composition comprising a biomolecule conjugated to a homopolymer or copolymer comprising the general structure:

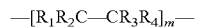

wherein m defines a number of repeat units sufficient to yield a molecular weight of said homopolymer or co-polymer from 4,200 g/mol to 19,000 g/mol, wherein $R_1$-$R_4$ are independently selected from hydrogen or a side chain comprising at least one carbon atom, and wherein at least one of $R_1$-$R_4$ is -L-trehalose, wherein L is a linking group that links trehalose to the monomer through at least one of the trehalose hydroxyl groups (—OH), wherein the homopolymer or copolymer further comprises a biomolecule reactive chain transfer agent attached to one or both termini of the homopolymer or copolymer backbone, and wherein L is selected from group consisting of -aryl-$(CH_2)_{n1}$— ($_{n1}$=0-6), —(COO)—$(CH_2)_{n6}$— ($_{n2}$=0-6), —(CONH)—$(CH_2)_{n3}$— ($_{n3}$—0-5), —$(CH_2)_{n4}$— ($_{n4}$=0-6), -aryl-(CH)—, —(COO)—$(CH_2)_{n7}$—(CH)— ($_{n7}$=1-6) and —(CO)—.

23. The composition of claim 22, wherein the biomolecule is selected from the group consisting of a protein, an enzyme, an antibody, a DNA, a RNA and an siRNA.

24. The homopolymer having the structure of:
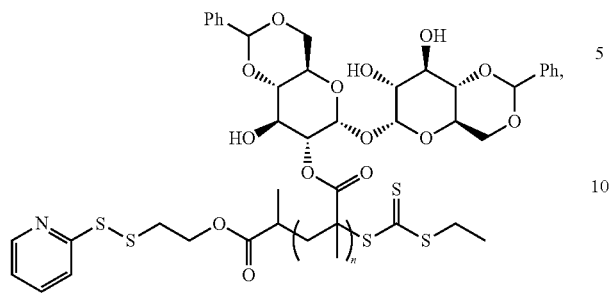
wherein n defines a number of repeat units sufficient to yield a molecular weight of said homopolymer from 4,200 g/mol to 19,000 g/mol.
25. A composition comprising a biomolecule conjugated to the homopolymer of claim 24.
* * * * *

UNITED STATES PATENT AND TRADEMARK OFFICE
CERTIFICATE OF CORRECTION

PATENT NO. : 9,901,648 B2  
APPLICATION NO. : 14/374388  
DATED : February 27, 2018  
INVENTOR(S) : Heather D Maynard et al.

Page 1 of 1

It is certified that error appears in the above-identified patent and that said Letters Patent is hereby corrected as shown below:

In the Specification

Column 1, Lines 21-22, "dation, and of Grant No. EB136774, awarded by the National Institutes of Health. The" should be --dation. The--.

Column 6, Line 24, "chromatography" should be --choromatography--.

Column 24, Line 51, "carbamoylation" should be --carbamylation--.

Column 28, Line 17, "F(ab')$_2$" should be --F(ab')2--.

Column 28, Line 21, "F(ab')$_2$" should be --F(ab')2--.

Column 28, Line 22, "F(ab')$_2$" should be --F(ab')2--.

Column 28, Line 25, "F(ab')$_2$" should be --F(ab')2--.

Column 38, Line 41, "(8=12.76)" should be --($\varepsilon$=12.76)--.

Column 45, Line 17, "argon" should be --agron--.

Column 60, Line 50, "Fi-Galactosidase" should be --β-Galactosidase--.

Signed and Sealed this  
Nineteenth Day of March, 2019

Andrei Iancu  
*Director of the United States Patent and Trademark Office*